(12) United States Patent
Kohn

(10) Patent No.: US 9,376,692 B2
(45) Date of Patent: Jun. 28, 2016

(54) PROCESS FOR RAPID ANAEROBIC DIGESTION OF BIOMASS USING MICROBES AND THE PRODUCTION OF BIOFUELS THEREFROM

(75) Inventor: Richard Allen Kohn, College Park, MD (US)

(73) Assignee: UNIVERSITY OF MARYLAND, College Park, MD (US)

( * ) Notice: Subject to any disclaimer, the term of this patent is extended or adjusted under 35 U.S.C. 154(b) by 669 days.

(21) Appl. No.: 12/320,333

(22) Filed: Jan. 23, 2009

(65) Prior Publication Data

US 2009/0137016 A1     May 28, 2009

Related U.S. Application Data

(63) Continuation of application No. 12/000,856, filed on Dec. 18, 2007, now Pat. No. 9,121,040.

(60) Provisional application No. 60/870,441, filed on Dec. 18, 2006.

(51) Int. Cl.
| | |
|---|---|
| *C12P 7/06* | (2006.01) |
| *C12P 5/02* | (2006.01) |
| *C01B 3/50* | (2006.01) |
| *C10L 3/08* | (2006.01) |
| *C12P 3/00* | (2006.01) |
| *C12P 7/04* | (2006.01) |
| *C12P 7/10* | (2006.01) |
| *C12P 7/14* | (2006.01) |
| *C12P 7/16* | (2006.01) |
| *C12P 39/00* | (2006.01) |

(52) U.S. Cl.
CPC ............... *C12P 5/023* (2013.01); *C01B 3/501* (2013.01); *C10L 3/08* (2013.01); *C12P 3/00* (2013.01); *C12P 7/04* (2013.01); *C12P 7/065* (2013.01); *C12P 7/10* (2013.01); *C12P 7/14* (2013.01); *C12P 7/16* (2013.01); *C12P 39/00* (2013.01); *C01B 2203/0405* (2013.01); *C01B 2203/048* (2013.01); *Y02E 50/10* (2013.01); *Y02E 50/16* (2013.01); *Y02E 50/17* (2013.01); *Y02E 50/30* (2013.01); *Y02E 50/343* (2013.01)

(58) Field of Classification Search
None
See application file for complete search history.

(56) References Cited

U.S. PATENT DOCUMENTS

| | | | | |
|---|---|---|---|---|
| 3,711,392 | A | * | 1/1973 | Metzger .................. 210/603 |
| 5,620,877 | A | | 4/1997 | Farone et al. |
| 6,509,180 | B1 | * | 1/2003 | Verser et al. ............ 435/161 |
| 7,682,811 | B2 | * | 3/2010 | Leschine et al. ........ 435/161 |
| 2003/0077771 | A1 | | 4/2003 | Verser et al. |
| 2003/0203454 | A1 | | 10/2003 | Chotani et al. |
| 2004/0157301 | A1 | | 8/2004 | Chotani et al. |
| 2005/0100996 | A1 | | 5/2005 | Lantero et al. |
| 2006/0011491 | A1 | | 1/2006 | Logan et al. |
| 2006/0024801 | A1 | | 2/2006 | Holtzapple et al. |
| 2006/0084156 | A1 | | 4/2006 | Lantero et al. |
| 2007/0178569 | A1 | | 8/2007 | Leschine et al. |
| 2007/0275438 | A1 | | 11/2007 | David |
| 2008/0187975 | A1 | | 8/2008 | Kohn |
| 2008/0193989 | A1 | | 8/2008 | Verser et al. |
| 2009/0017513 | A1 | | 1/2009 | Bell et al. |
| 2009/0023192 | A1 | | 1/2009 | Verser et al. |
| 2009/0035848 | A1 | | 2/2009 | Hickey |
| 2009/0068714 | A1 | | 3/2009 | Leschine et al. |

FOREIGN PATENT DOCUMENTS

| | | |
|---|---|---|
| WO | WO 2006/119052 | 11/2006 |
| WO | WO 2007130984 | 11/2007 |

OTHER PUBLICATIONS

Pavlostathis et al. "Fermentation of insoluble cellulose by continuous cultures of Ruminococcus albus". Applied and Environmental Microbiology. 1988, vol. 54, No. 11, pp. 2655-2659.*
Desvaux et al. Applied and Environmental Microbiology. 2000, vol. 66, No. 6, pp. 2461-2470.*
Lamed et al. Applied and Environmental Microbiology. 1988, vol. 54, No. 5, pp. 1216-1221.*
Freier et al. Applied and Environmental Microbiology. 1988, vol. 54, No. 1, pp. 204-211.*
Russell et al. Journal of Animal Science. 1988, 66:552-558.*
K. Sudra Rani et al. "High Ethanol Tolerance of New Isolates of Clostridium thermocellum strains SS21 and SS22". World Journal of Microbiology & Biotechnology, vol. 15, No. 2, Apr. 1, 1999, pp. 173-178, XP05508101.
Jorge Rodriguez et al. "Modeling Product Formation in Anaerobic Mixed Culture Fermentations", Biotechnology and Bioengineering, vol. 93, No. 3, Feb. 20, 2006, pp. 592-606, XP055079831, ISSN: 0006-3592.
Cord-Ruwisch, R., Seitz, HJ, and Conrad, R. The Capacity of Hydrogenotrophic Anaerobic Bacteria to Compete for Traces of Hydrogen Depends on the Redox Potential of the Terminal Acceptor. Arch. Microbiol. 1988; 149:350-357.
Finney, C.D. and Evans, R.S. II. 1975 Anaerobic Digestion: The Rate Limiting Process and the Nature of Inhibition, Science, New Series, vol. 190, No. 4219, Dec. 12, 1975, pp. 1088-1089.
Finney, C.D., Evans, R.S. and Finney, K.A. 1977. Fast Production of Methane by Anaerobic Digestion. Annual Report. U.S. Department of Energy Division of Buildings and Community Systems. Contact No. EY-76-C-02-2900.
Hannson, G. 1982. Methane Production from Glucose and Fatty Acids at 55-85 F. Biotechnology Letters vol. 4 (12) 789-794.

(Continued)

Primary Examiner — Vera Afremova
(74) Attorney, Agent, or Firm — William Beaumont Juneau & Mitchell

(57) ABSTRACT

A process for effecting anaerobic digestion of plant biomass, which entails the step of anaerobically digesting plant biomass with at least one species of rumen microorganisms.

21 Claims, 24 Drawing Sheets

(56) References Cited

OTHER PUBLICATIONS

Hashimoto, A.G. 1982. Effect of Mixing Duration and Vacuum on Methane Production Rate from Beef Cattle Waste. Biotechnology and Bioengineering 24:9-23.

Hannson and Molin. 1981. Eur. J. Appl. Microbiol. Biotechnol. 13:242-247.

Hannson and Molin. 1981. Eur. J. Appl. Microbiol. Biotechnol. 13:236-241.

Hannson (1979) Eur. J. Appl. Microbiol Biotechnol. 6:351-359.

Kasal, GB; Senior. E.; and Watson-Craik, Irene A. (1990) Refuse Acidogenesis and Methanogenesis: Effects of Fermentation Gases (H2, CO2, CH4) Letters in Appiied Microbiol v11 n2 (199008):65-68.

Morvan, B., Bonnemoy, F., Fonty, G. and Gouet, P. Quantitative Determination of H2-Utilizing Acetogenesis and Sulfate-Reducing Bacteria and Methanogenic Archaea from Digestive Tract of Different Mammals. Current Microbiology 1996; 32; 129-133.

Sterling, et al. 2001. Bioresource Technology 77:9-18.

Strayer, R.F. and Tiedje, J.M. (1978) Kinetic Parameters of the Conversion of Methane Precursors to Methane in Hypereutrophic Lake Sediment. Appl. Environ. Microbiol. 36:330-340.

Thauer, R.K., Jungermann, K. and Decker, K. (1977) "Energy Conservation in Chemotrophic Anaerobic Bacteria". Bacteria Rev. vol. 41 No. 1 pp. 100-108.

Fantozzi, F. and Buratti, C. 2009. Biogas Production from Different Substrates in an Experimental CSTR Anaerobic Digester. Bioresource Technol. 100(23):5783.

\* cited by examiner

PROCESS FOR RAPID ANAEROBIC DIGESTION OF BIOMASS USING MICROBES AND THE PRODUCTION OF BIOFUELS THEREFROM

This application is a continuation application of U.S. patent application Ser. No. 12/000,856, filed Dec. 18, 2007. PCT/US2007/025788, filed Dec. 18, 2007. Provisional application U.S. Ser. No. 60/870,441, filed Dec. 18, 2006.)

BACKGROUND OF THE INVENTION

1. Field of the Invention

The present invention is directed to a process for rapid anaerobic digestion of biomass using microorganisms and the production of biofuels therefrom.

2. Description of the Background

In 2005, the United States consumed more than $715 billion in oil, with imported oil contributing to 35% of oil consumption, with that figure likely to rise to as much as 70% of consumption over the next 20 years. In an effort to alleviate this dependency, 1% of the U.S. corn crop was used to provide 1.7% of fuel demand as corn ethanol in 2004. Unfortunately, even if all corn grain now grown in the United States were converted to ethanol, only about 15% of current transportation needs would be satisfied. Thus, corn-derived ethanol cannot provide a significant alternative to imported oil as a source of fuel.

The U.S. government has set a goal of replacing 30% of the nation's gasoline consumption with ethanol by 2030, which has been estimated to require 60 billion gallons of ethanol per year and an annual supply of a billion metric tons of dry biomass. The U.S. Departments of Agriculture and Energy have both found it feasible to produce this amount of biomass provided that plant fiber in wood and grasses is included. Thus, an economical method of biomass conversion of plant fiber of wood and grass to fuel is required to meet the goal set by the U.S. government.

Most agricultural biomass is in the form of structural carbohydrates (cellulose and hemicellulose) bound to the polyphenolic polymer, lignin. One bottleneck for biomass conversion to biofuels and other utilizable products is the degradation of biomass to fermentable carbohydrates. A second bottleneck is the conversion of these carbohydrates to fuels like ethanol. Glucose, is fermented by yeast to ethanol, but five-carbon sugars, which make up about half of plant cell wall carbohydrate, are not rapidly metabolized to ethanol by known microorganisms. Fermentation products of cell wall degradation include volatile fatty acids, but these have not been shown to be converted to ethanol with existing technology.

Although industrial bioconversions have been conducted with pure microorganism cultures, such conventional bioconversions have not been used successfully in converting fibers in woods and grasses to ethanol.

Thus, a need exists for a means by which fibers in woods and grasses could be converted to biofuels, such as ethanol.

SUMMARY OF THE INVENTION

Accordingly, it is an object of the present invention to provide a process for rapid anaerobic digestion of biomass, such as plant fibers, to hydrogen, methane or ethanol using a mixed population of microorganisms.

It is also an object of the present invention to provide a process for the production of biofuel with minimal loss of heat energy, and at low temperatures.

It is, furthermore, an object of the present invention to provide an anaerobic process for digestion of biomass which is at least twice as fast as conventional anaerobic digestion processes for biomass.

It is, additionally, an object of the present invention to provide a mixed culture of microorganisms which may be used to inoculate biomass fermentations.

The above objects and others are provided, in part, by a process for anaerobic digestion of biomass, which entails digesting the biomass with at least rumen microbes.

BRIEF DESCRIPTION OF THE DRAWINGS

FIG. 23 illustrates ratio of carbon dioxide to methane over time with digestion and fermentation with rumen microbes under 0.25 atmospheres total pressure (Vacuum), removal of gas every two hours and replacement with dimolecular nitrogen (Nitrogen), and maintained under 1 atmosphere produced gases: carbon dioxide and methane (Control). Average of 4 replicates per treatment: ANOVA indicated differences among treatments (P<0.01) for all time points beyond initial (2, 4, 6, 8 h); SE was 1.4 at T=0, and ranged from 0.1 to 0.24 depending on time point beyond that.

DETAILED DESCRIPTION OF THE PREFERRED EMBODIMENTS

Figure 1:
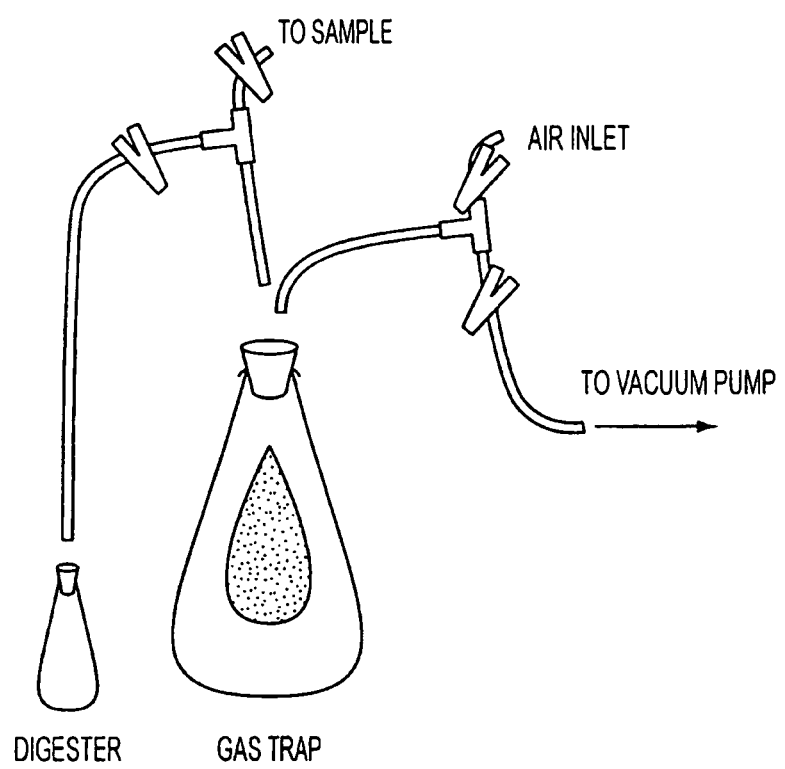
FIG. 1 illustrates a vacuum gas collector, including digester and gas trap, used to trap and collect gas while under a partial vacuum.

The present invention is based, at least in part, upon the discovery that rumen microorganisms and mixtures thereof effectively promote anaerobic digestion of biomass in a manner which is faster than conventional methodologies for anaerobic degradation of biomass. This discovery is advantageous as microbes harvested from the rumen of ruminant animals, such as cattle, sheep, goats, horses or even giraffes, are adapted to digest fiber and starch. Products resulting from such rumen digestion include methane, ethanol, hydrogen as well as alcohol precursors.

The present invention is also based, in part, upon the discovery that incubations and digestions can be conducted to specifically select the type of products produced.

Furthermore, the anaerobic digestion of the present invention is effected advantageously at low temperatures, such as at about 50° C. or less, and preferably at about 45° C. or less. However, it is even more preferable to use a temperature of about 40° C. or less. For example, temperatures from about 20° C. to about 40° C. may be used. These low temperatures allow for the anaerobic digestion of biomass without having to use expensive heating equipment which would be required for conventional anaerobic degradation.

Additionally, the present anaerobic digestion process may be conducted at a faster rate than conventional anaerobic digestion processes using enzymes or conventional microbes used for anaerobic digestion.

The present invention also provides a method of producing methane or hydrogen using at least rumen microbes.

Additionally, the present invention provides a method for enhanced production of hydrogen.

Furthermore, the present invention provides a flexible and adaptable means by which methane, hydrogen, ethanol or electric power can each be selectively produced depending upon conditions used, and as demand for each changes.

Moreover, the present invention also provides methods for enhanced production of butyrate and valerate, which as volatile fatty acids, are precursors to fuels.

Definitions of Terms Used Herein

As used throughout the present specification, the following definitions apply.

a) "low temperature" means a temperature of about 50° C. or less, and preferably about 45° C. or less, and even more preferably about 40° C. or less. Temperatures of as low as 20° C. are specifically contemplated.

b) "faster" means that the rate of the present anaerobic digestion is at least about twice (2x) as fast as a conventional anaerobic microbial digestion, and preferably about five times (5x) as fast. However, the present anaerobic digestion may be as much as ten (10x) to fifteen (15x) times as fast as a conventional anaerobic digestion.

c) "rumen microorganisms" means any or all of the microorganisms that are found in the rumen of ruminant animals. This includes a diverse array of archea, bacteria, protozoa and fungi which digest fibrous plant materials and ferment starches and sugars, for example.

This term also includes such microorganisms that are found elsewhere in the digestive tract of animals, feces, silage, sludge or in soil, among other places.

An exemplary list of rumen microorganisms that may be found either in the rumen or in the soil are:

Genus *Prevotella* (*P. ruminicola* and *P. bryantii*)
*Ruminobacter amylophilus*
*Fibrobacter succinogenes*
*Selenomonas ruminantium*
*Anaerovibrio lipolytica*
*Succinivibrio dextrinisolvens*
*Succinomonas amylolytica*
*Treponema bryantii*
*Ruminocaccus albus*
*R. flavefaciens*
*R. bromii*
*Streptococcus bovis*
*Megasphaera elsdenii*
*Butyrivibrio fibrisolvens*
*Lachnospira multipara*
*Lactobacillus ruminis*
*L. vitulinus*

*Eubacterium ruminantium*
*Clostridium polysaccharoliticum*
*Succiniclasticum ruminis*
*Wolinella succinogenes*
*Veilonella parvula*
*Methanobrevibacter ruminantium*
*Methanobacterium* formicicum
*Methanosarcina barkeri*
*Methanosarcina mazei*
*Methanomicrobium mobile*
  genus *Neocallimastix* (*N. frontalis* and *N. patriciarum*)
  genus *Piromyces* d) "rumen" means an enlarged digestive compartment found in ruminants, such as cattle, sheep, goats, deer, horses and giraffes, for example, for the pre-gastric fermentation of foodstuffs by rumen microorganisms.

e) an "anaerobic digestion" means a process for anaerobically digesting plant biomass.

f) a "slight vacuum" is defined herein to mean from about 0.75 to 0.05 atm, preferably 0.50 to 0.15 atm, and most preferably from 0.40 to 0.20 atm.

g) "rumen" and "gut" are used interchangeably in this application.

h) "short chain" as used herein for short chain fatty acids means $C_2$-$C_6$, preferably $C_1$-$C_4$, fatty acids; and "lower alkyl" as used herein for lower alkyl alcohols means $C_2$-$C_6$, and preferably $C_2$-$C_4$, alkyl alcohols.

i) "non-rumen microorganisms" means any microorganisms, other than those obtained from a rumen, that are known to be useful in digesting biomass. Such microorganisms may be found in feces or may even have marine origin, such as Microbulbifers degradans 2-40.

Ruminants have co-evolved with microorganisms to rapidly convert plant biomass to energy for the host animal. The rumen ecosystem, and the ways in which the host has evolved, have been studied for several decades with the aim of understanding ways to increase digestion rate and efficiency of energy capture. For example, animal nutritionists have sought to decrease methane production rates from animals, since methane released to the atmosphere acts as a potent greenhouse gas. In addition, the release of methane is an undesirable energy loss for production ruminants. It is generally understood that methane is produced from $CO_2$ and $H_2$ in the rumen, but also from degradation of volatile fatty acids in methane digesters. Although previous research has established that methane is produced in the rumen and in artificial cultures, these organisms to date, have not been removed from the rumen to produce methane from biomass in bioreactors.

Hydrogen gas is produced by rumen microorganisms during digestion of plant fiber. Most of this hydrogen is transferred to methanogens to produce methane. Yet, when hydrogen gas is released from rumen fermentation, only a small percentage of the total fermentation gas is released as hydrogen. Yet, to date, the inhibition of $CH_4$ formation to produce $H_2$ as a fuel has not been reported.

As noted above, utilization of grasses, trees and fibrous by-products from crops and industry would greatly increase land productivity of ethanol. The greatest hurdle to the use of fibrous materials for ethanol production is the digestion of recalcitrant cell walls. Some previously proposed methodologies have suggested improving cell wall digestion are pre-treatment of feeds at high temperature (450 to 650° C.) with acids, and the use of enzymes to release glucose for fermentation. However, such high temperatures are energetically expensive and, thus, impractical for wide-scale practical use.

There is currently a great deal of interest in engineering bacteria to convert cellulose to ethanol or precursors of ethanol. Organisms with these desired traits were discovered decades ago to exist in the rumen of cattle. Previous research treated ethanol as an undesirable fermentation product that accumulates only occasionally and which the animal is not well adapted to utilize. Thus, a principal objective has actually been to prevent ethanol accumulation in the rumen. Thus, the use of rumen organisms to produce fuel or beverage alcohol has not been disclosed, and, in fact, appears counterintuitive based on conventional wisdom.

Acetate, the main fatty acid produced in the rumen, is a two-carbon acid that differs from ethanol by being more oxidized. Bacteria are known which can reduce acetate to ethanol in pure culture. However, the use of such bacteria for the practical production of alcohol has not been disclosed. Moreover, ethanol production from acetate or other volatile fatty acids has not been demonstrated in mixed cultures.

A bacterium from the rumen, *Ruminococcus albus*, has been shown in pure culture to produce ethanol from the two-glucose unit of cellulose called cellobiose. Ethanol was also shown to be a product of two rumen fungi that digest fiber, *Neocallimastix* sp. NC71 and *Piromyces* sp. PC12. Rumen spirochetes have been shown to make ethanol from five-carbon sugars. Ethanol production and accumulation were observed in vitro when digesting alfalfa hay using a mixed culture of rumen microorganisms and methane inhibitors. Ethanol production in the rumen has been shown to cause sickness in sheep fed diets high in readily fermentable starch. Normally, although ethanol might be produced in the rumen in small concentrations, it is not observed before it is converted to a more thermodynamically stable end product. In one important aspect of the present invention, conditions have been discovered that shift the equilibrium toward ethanol production to lead to its accumulation. Moreover, these conditions can be used for enrichment of microbial species that produce ethanol.

Notably, the present invention provides chemical redox agents/conditions which shift chemical equilibrium to enhance production of ethanol. For example, the inclusion of sulfite compounds in the digestion mixture can increase production of ethanol by up to 10 times.

In another aspect, rumen, microbes are used to produce electricity in microbial fuel cells. Further, the effect of electricity production on removal of hydrogen equivalent and subsequent production of other biofuels is disclosed herein. The combination of electricity production in a microbial fuel cell while other fuels are also produced is further disclosed herein. The use of conditions such as gas perfusion as a means to increase electricity production is also disclosed herein. Although molecular hydrogen ($H_2$) is known to be produced by rumen microbes, only very low concentrations (e.g. 0.05% of total gas volume) are typically observed in the ruminant gut. It has been calculated that the key reactions utilizing hydrogen are close to equilibrium in the rumen based on thermodynamic ($\Delta G$) data. These reactions are shown below:

Methanogenesis:

$$CO_2 + 4H_2 \leftarrow\rightarrow CH_4$$

Volatile Fatty Acid Interconversions:

$$CH_3COOH \text{ (Acetate)} + 3H_2 + CO_2 \leftarrow\rightarrow CH_3CH_2COOH \text{ (Propionate)} + 2H_2O$$

$$2CH_3COOH \text{ (Acetate)} + 2H_2 \leftarrow\rightarrow CH_3CH_2CH_2COOH \text{ (Butyrate)} + 2H_2O$$

Reductive Acetogenesis:

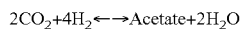

$$2CO_2 + 4H_2 \leftrightarrow Acetate + 2H_2O$$

Ethanol is known to be produced in the rumen in very low concentrations under some conditions. The present inventor has determined that acetate and propionate are more thermodynamically favorable than ethanol under normal conditions in the rumen, but it is hypothesized that ethanol production can be made thermodynamically favorable in vitro. One means to make ethanol more favorable would be to increase $H_2$ concentration by inhibiting methanogenesis or propionate synthesis. Including methanogens in cultures of ethanol-producing fungi decreased production of ethanol presumably because methanogens consumed $H_2$, and including methane inhibitors increased ethanol accumulation in vitro.

Because all of these reactions are close to equilibrium, it is postulated that removing end products desired or providing additional substrates will shift the ratio of other products and reactants toward reestablishing equilibrium. It is disclosed herein that several methodologies can be used in accordance with the present invention to shift the profile of products and reactants toward desired biofuels. This approach is applicable not only to microbial cultures from the rumen, but also to other microbial fermentations.

Sampling of Rumen Microorganisms

Procedures are well-known for rumen microorganism sampling. One such known example may be noted here for fungal *rhizobia*.

Approximately 250 ml rumen fluid is harvested by suction per fistula from a non-lactating Holstein dairy cow receiving a high forage diet. The fluid is strained twice through four layers of cheesecloth and transported to the laboratory in an insulated container to avoid cold shock. The fibrous residue remaining after straining is likewise taken to the laboratory and is examined for fungal *rhizobia*.

Half of the fluid is gassed with carbon dioxide and incubated at 39 degrees for later examination. The remainder is diluted with 50% formalin and separate aliquots are stained with methylene blue, brilliant green, or iodine to emphasize structural components and aid in identification see (Dehority, 1993. Laboratory Manual for Classification and Morphology of Rumen Ciliate Protozoa. CRC Press, Inc., Boca Raton, Fla.).

Use of Rumen Microbes to Inoculate Digesters for Biomass Degradation and/or Energy Production Microorganisms may be harvested from the rumen of cattle, sheep, goats, or other ruminant animal to inoculate digesters of plant biomass for the production of biofuels. The organisms in the rumen have evolved to rapidly digest plant biomass, and survive high dilution rates. These microbes have been shown to make methane and ethanol directly from fiber, or indirectly from intermediates of biomass digestion. The organisms can be taken directly from surgically altered animals that have fistulae inserted into their sides directly to the rumen.

Anaerobic digestion can be used to digest plant biomass and waste to yield alkanes, like methane, and alcohols like ethanol, propanol, and butanol. These products can be made directly from biomass or from products of a primary reaction. Biomass degradation is used to treat waste and produce energy in the form of methane. We propose also using rumen fluid to produce alcohols for commercial energy use. Rumen organisms may also be used for electricity generation from biomass.

Contents removed from the rumen of cows can be incubated in reactor vessels under conditions to accelerate digestion rate and shift fermentation pathways toward desired products. The following experiments show that rumen microbes can be used to produce methane, or organic acids like acetate, and hydrogen. Acetate and hydrogen are precursors for ethanol production.

A Process for Rapid Anaerobic Digestion of Biomass

Another aspect of the present invention entails the removal of hydrogen equivalent to accelerate microbial degradation of substrate in an anaerobic environmental, shift fermentation products, and/or capture hydrogen equivalent for subsequent reactions. An anaerobic digester may typically be used for biomass degradation and fermentation. Generally, the following is required: 1) plant biomass substrate, 2) incubation media, and 3) microbial inocula harvested from rumen of cattle, or environment with organisms selected for digestion of the material used as a substrate.

In more detail, as a biomass substrate, one may use whole plant materials, such as grasses, and particularly switch grass, or wood and leaves. Further, it is acceptable to use grains, such as corn or wheat; residential waste, food waste or even human and/or animal manure.

As incubation media, it is acceptable to use conventional media, which typically contain water, salts, and phosphate buffers in a manner that mimics or simulates conditions where the microorganisms being used were harvested.

The digester accelerates microbial degradation of these substrates without loss of energy through oxidation by removing and capturing electrons through one of the following means: 1) provision of slight vacuum, such as 0.25 atm., for example, to remove gases including hydrogen and methane, 2) perfusion with non-reactive (inert) gases (e.g. $N_2$, He) which maintain total atmospheric pressure to prevent equipment leaks or caving, but which decrease partial pressures of reduced compounds, 3) addition of oxidizing chemical compounds which can later be removed and used for biofuel (e.g. methane, ethanol) synthesis or polymerization reactions, 4) production of electricity using electrodes linked to oxidized reactions, or 5) a combination of methods listed. Chemical oxidizing compounds include sulfate (aqueous), which is reduced to sulfide and removed in gaseous phase, and $Fe^{+4}$, which is reduced to $Fe^{+3}$, which can be passed through to a second state reactor.

In addition to greatly accelerating anaerobic reactions, the process provides greater control of fermentation by shifting fermentation away from reducing pathways and enabling use of reduced compounds in a different reactor. It also enables microbes to thrive that would otherwise be limited by ability to remove hydrogen.

The present invention is readily distinguishable from other biomass digestions by the 1) active and controlled removal of hydrogen equivalents or electrons, 2) acceleration of the digestion process, 3) control of which products are formed, and 4) capture of hydrogen or reduced compounds for use in subsequent reactions.

Anaerobic digestion and fermentation reactions are used in a variety of industrial applications including food microbiology (cheese, pickles), animal feeds (silage, high moisture corn grain), beverages (beer, wine, spirits), bio fuels (methane, ethanol), and waste processing (wood byproducts, food waste, animal manure). Anaerobic digestion also occurs in the fore gut of ruminants and hind gut of many animals including humans. The proposed technique may have applications in all of these processes. One aspect of the present invention thus pertains to the biodegradation of plant biomass to organic acids and hydrogen, and the subsequent conversion of organic acids to alcohols for fuels. Another aspect pertains to biodegradation of biomass for methane production. Yet another aspect pertains to the development of feed additives to enhance degradation in ruminants or non-ruminants.

Having described the present invention, reference will now be made to certain examples which are provided solely to illustrate and not limit the same.

The following experiments show that removing hydrogen gas via vacuum, or by supplying nitrogen to substitute for fermentation gasses, greatly accelerates digestion by rumen microbes in vitro, shifts fermentation away from methane, and enables the capture of hydrogen gas for subsequent use.

EXAMPLES

All experiments were conducted at the University of Maryland in College Park according to the following general procedures except where indicated otherwise. Use of two ruminally cannulated cows was approved by the University Animal Care and Use Committee.

Initial in vitro experiments used timothy grass hay as substrate. For each digestion experiment, we obtained one-half liter of rumen contents from each of two ruminally-cannulated cows two to four hours after morning feeding. The digesta were mixed and ground in a Waring blender for 1 minute while being maintained under $CO_2$ gas. Fluid was strained through four layers of cheese cloth followed by glass wool to remove large particles. Rumen fluid was added to a bicarbonate or 0.1 M sodium phosphate buffer with mineral salts.

Gas samples were collected continuously in mylar balloons, and gas volumes recorded at various time points. Glass tubing coated with epoxy was pushed into the opening on the mylar balloons. The tubing was connected to luer-lock connectors via nylon tubing. Samples were taken using glass syringes attached to the luer-lock connectors. Samples were stored in gas-tight vials for analysis of composition by GC with thermal conductivity detector. Rates of gas production were determined by fitting an inverted exponential equation.

Gas samples were collected under vacuum using the following apparatus (FIG. 1). Two pieces of glass tubing were pushed through a rubber stopper, and that stopper fitted into a 2-L filtering flask. Inside the flask, one piece of glass tubing was pushed into the opening of a mylar balloon, affixed with epoxy, and tested for air leaks. Outside the flask, each piece of glass tubing was connected to a three-way valve. The first valve leading to the tubing with the balloon attached inside the flask was connected to the in vitro digester flask at one opening, and a luer-lock connector for sample collection from the balloon at the other opening. The second valve was connected to a vacuum line or left open to the air. In order to apply vacuum, the first valve was opened to the in vitro and the second valve opened to the vacuum line. In order to take a gas sample, the first valve was closed and the second valve opened to the atmosphere to relieve the vacuum pressure in the collector. Then, a gas sample was measured under atmospheric pressure and taken using a glass syringe connected to the first valve.

The pH and reducing potential were determined using standard glass or platinum electrodes respectively, while maintaining the gas composition by keeping the flasks closed to the atmosphere with putty fitted around the electrodes. Liquid samples were collected at designated time points and analyzed by gas chromatography (GC) for alcohols (methanol, ethanol, propanol, butanol) volatile fatty acids (acetate, propionate, butyrate, etc). Rates of alcohol or VFA production were determined by fitting an inverted exponential equation.

Digesta residues were used to determine microbial protein production and digestibility of organic matter, crude protein and neutral detergent fiber (cell wall fraction). Incubations for microbial protein production were enriched with 2% $^{15}N$. After incubation, these samples were centrifuged at 400×g for 10 minutes to remove undigested feed particles, and microorganisms attached to them. The supernatant was centrifuged at 15,000×g for 30 minutes to remove free microorganisms. Both pellets were dried at 50° C. and analyzed for dry mass, $^{15}N:^{14}N$ ratio and total N. Attached microbial protein was calculated as 6.25 times $^{15}N:^{14}N$ in pure microbial pellet times $^{15}N$ in the first pellet. Total microbial protein was calculated as attached microbial protein+free microbial protein. True digestibility was calculated by subtracting the microbial portion from the residue.

True fiber digestibility was determined directly on the residue of digestion by refluxing in pH-neutral detergent solution for one hour, drying at 100° C. overnight and weighing.

All results were analyzed using the statistical software, JMP (SAS Inst., 2005) and significance was accepted at $P<0.05$.

Example 1

Effect of Vacuum or $N_2$ Perfusion on Fermentation Balance

In one treatment, partial pressures of all fermentation gases were reduced simultaneously by applying vacuum (0.07 atm), and in another treatment, partial pressures were reduced by perfusing inert $N_2$ gas through the system. A typical in vitro rumen fermentation batch culture with gases collected in attached mylar balloons served as the control. Fourteen 250-ml flasks with media and inocula from the rumen were incubated for each of the three treatments, with two flasks removed at each time point. Samples were incubated for 0, 1, 2, 4, 6, 12, or 24 h. The experiment was replicated with three runs, but some results varied by run and are therefore described separately.

The control treatment used sodium bicarbonate buffer under $CO_2$ and reduction with $Na_2S$ and cysteine as recommended for in vitro fermentation. Measured 1-g samples of timothy hay (previously ground through a 1-mm screen of a Wiley mill) were incubated in 250-ml flasks with 80 ml of buffered media and 20 ml of rumen inocula. Gases were allowed to accumulate in mylar balloons attached to each flask.

The vacuum and perfusion treatments replaced the bicarbonate buffer with 0.1 M phosphate (final concentration of media before adding rumen fluid) prepared with a sodium phosphate salt adjusted to pH 6.8. Vacuum was applied continuously to 0.07 atm and gases collected as needed to maintain the low pressure. For $N_2$ perfusion treatment, three-way valves were fitted between the digester flask and collection balloon. The gas headspace volume was increased from 160 ml to 260 ml by drawing out gas with a glass syringe connected to the digester flask. The gas removed to the syringe was pushed into the collection balloon, and $N_2$ (61 ml at 1 atm.) from a balloon under atmospheric pressure was allowed into the digester flask. Perfusions were performed on all remaining samples after 2, 4, 6, or 12 h.

The volume and concentration of gases in each flask and balloon were determined at the end of the length of incubation. Digester fluid was analyzed for volatile fatty acids, and residue was dried at 50° C. in a forced air oven. The residue was split for determination of NDF, dry matter, ash, organic matter and microbial and feed protein.

The first run used paired centrifuge tubes in place of the single flask. However, many samples for the vacuum treatment boiled over and spilled into each other in this run. The combined low pressure and incubation temperature (39° C.) is near the boiling point for water. For this reason, the residues could not be analyzed reliably. Results are only shown for the second and third runs unless otherwise indicated.

The subsequent runs used 250-ml flasks for all treatments, and added a distillation apparatus to the flasks applying vacuum. A 50-ml volumetric pipette was fitted inside a large stiff piece of polyvinyl tubing. The bottom of the tubing was closed with a 1-hole rubber stopper allowing the pipette to exit and be attached to the in vitro flask. Ice water was delivered to the top of each distillation unit by gravity and removed with a peristaltic pump. The apparatus was suspended with a rack attached to the water bath. After leaving the top of the pipette, gas samples were pulled through a 125-ml flask in a cooler with dry ice to remove any volatile liquids before removing the gases to the mylar balloon in the vacuum collector. Use of this apparatus prevented samples from boiling over, but resulted in greater leakage as measured and accounted for as $N_2$ in the gas samples.

Results

Hydrogen is produced during digestion of feed in the rumen, but is rapidly used to reduce $CO_2$ to $CH_4$ and pyruvate to propionate. In this experiment, decreasing the partial pressures of $H_2$ and $CO_2$ resulted in several shifts in the fermentation as well as greater $H_2$ production.

Due to the combination of low pressure and incubation temperature, samples boiled over and into the tubing for the vacuum treatment in the first run. The use of condensers in the second and third runs eliminated the loss of sample into the tubing and balloons during vacuum fermentation. There was negligible liquid condensed in the flasks in dry ice. However, there was more leaking in the vacuum treatment in the second and third runs as evidenced by greater $N_2$ percentage in gas samples. Most leaking occurred in short time periods (when gas accumulation was visually rapid), but air was thus added to the collected gas sample. This leaking was accounted for by measurement of $N_2$ in gas samples.

Concentrations of $H_2$ and $CH_4$ for the second and third runs are shown in Table 1. The $H_2$ concentration was slightly greater (P<0.05) in the vacuum treatment (0.065%), and less in the perfusion treatment (0.033%) compared to the control (0.057). In the first run, with less leaking of air, $H_2$ concentration averaged three times greater (P<0.01) for the vacuum treatment (0.14%) than for the control (0.054%), demonstrating that vacuum treatment can be used to concentrate $H_2$ during fermentation.

TABLE 1

Concentration of molecular hydrogen ($H_2$) and methane ($CH_4$) in fermentation gases.

| Item | Treatment[1] | | | SE[2] | P<[3] |
| --- | --- | --- | --- | --- | --- |
| | Vacuum | $N_2$ | $CO_2$ | | |
| $H_2$ (% of all gases) | 0.065 | 0.033 | 0.057 | 0.008 | 0.03 |
| $H_2$ (% of fermentation gases)[4] | 0.23 | 0.24 | 0.061 | 0.29 | 0.0001 |
| $CH_4$ (% of all gases) | 0.72 | 1.13 | 2.25 | 0.25 | 0.0001 |
| $CH_4$ (% of fermentation gases) | 3.0 | 6.4 | 2.4 | 0.62 | 0.0001 |
| $CH_4$:$H_2$ (molar ratio) | 14.0 | 69.6 | 46.4 | 13.0 | 0.01 |

[1]Treatments were fermentation under vacuum pressure (0.07 atm), nitrogen perfusion, or with $CO_2$ and fermentation gases not removed (control).
[2]Standard error of the mean, n = 3 per treatment.
[3]Significance of treatment effect
[4]Molar percentage among fermentation gases, excluding $N_2$.

When expressed as a percentage of fermentation gases (excluding $N_2$), all runs were similar with about a four times greater concentration of $H_2$ in the vacuum (0.23%) or perfusion treatments (0.24%) compared to the control (0.06%). There was no effect (P>0.1) of length of incubation on $H_2$ concentration over time for any treatments suggesting that the changes occurred very quickly (within the hour between measurements) and the fermentation stabilized to a new equilibrium.

Methane concentration was greater as a percentage of all gases for the control treatments, but $CH_4$ concentration as a percentage of fermentation gases was greater for the $N_2$ perfusion treatment. The control ($CO_2$) treatment would dilute the fermentation gases with $CO_2$ from initial perfusion and bicarbonate in solution. The decreased $CH_4$ concentration for the vacuum treatment compared to the $N_2$ perfusion reflects the decreased methanogenesis relative to gas concentrations due to the removal of $H_2$.

The thermodynamics of methanogenesis from reduction of $CO_2$ suggest that methanogenesis should be decreased relative to $H_2$ and $CO_2$ when decreasing partial pressures of all gases because five moles of gas (1 $CO_2$+4$H_2$) react to produce 1 mole of product gas ($CH_4$). The empirical results regarding $H_2$ were consistent with the theoretical expectations. As methanogenesis from $CO_2$ and $H_2$ decreased, more $H_2$ was released rather than used to reduce carbon dioxide.

The ratio of $CH_4$ to $H_2$ (mol/mol) differed by treatment with vacuum treatment less than control and $N_2$ perfusion. There was also an effect of time (P<0.01) and an interaction of time with treatment (P<0.0001) with $CO_2$ (control) and $N_2$ treatments increasing with time, and vacuum decreasing with time. The increasing ratio of $CH_4$ to $H_2$ over time suggests methanogenesis ramped up over time for control treatments, but not for vacuum treatment, which was limited by thermodynamics.

Figure 2:
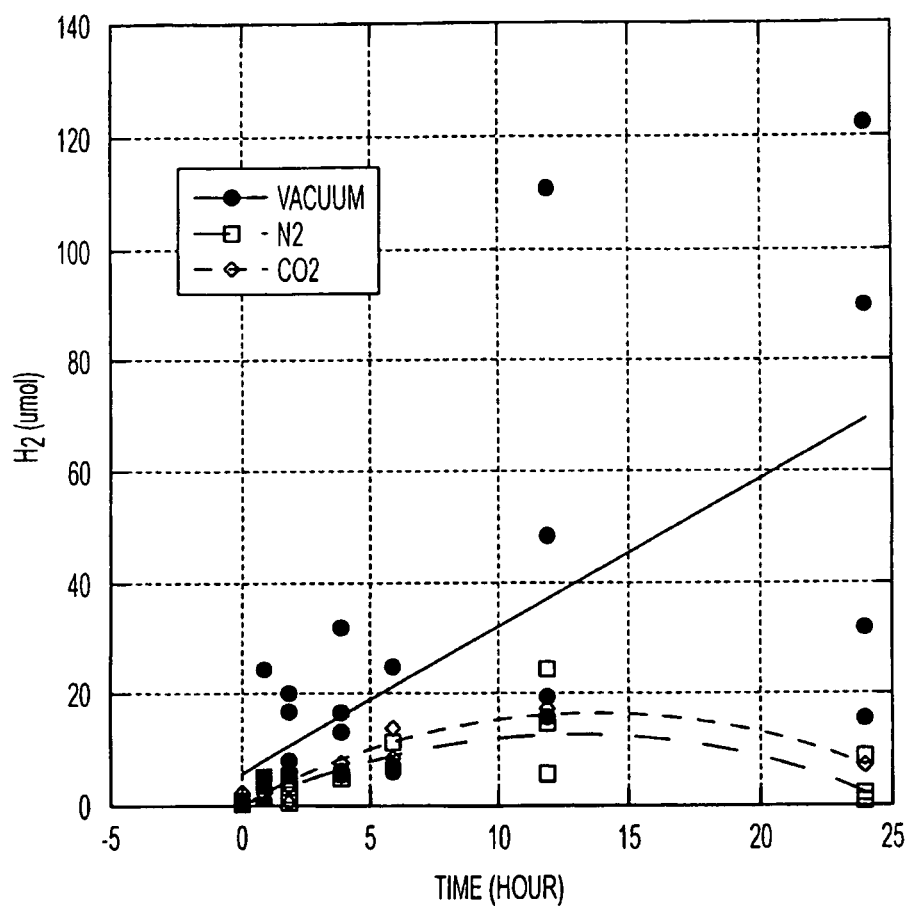
FIG. 2 illustrates the effect of vacuum, $N_2$ perfusion or incubation with $CO_2$ on hydrogen release from fermentation flasks.
Figure 3:
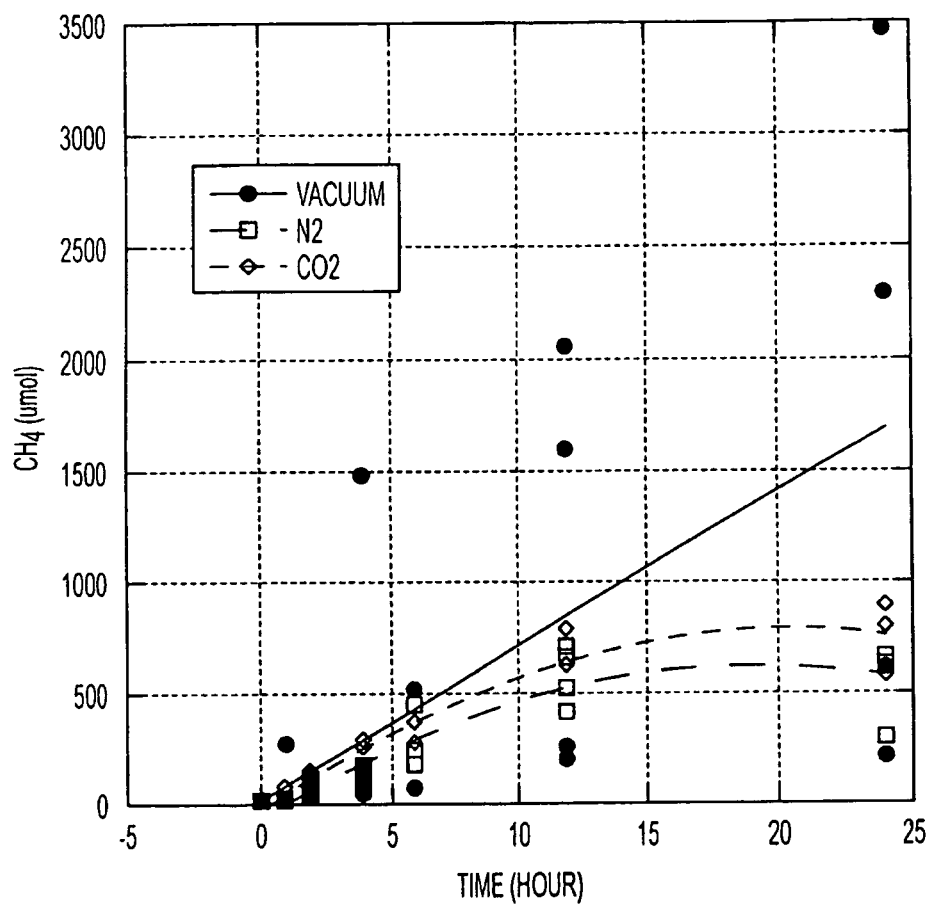
FIG. 3 illustrates the effect of vacuum, $N_2$ perfusion or incubation with $CO_2$ on methane production from fermentation flasks.

Although highly variable, $H_2$ production (µmol) was much greater (P<0.0001) for the vacuum treatment than for control or $N_2$ perfusion. This effect was consistent across all three runs, but only the second two runs are shown in FIG. 2. Production of $CH_4$ was also greater (P<0.0001) and increased faster (P<0.0001) for the vacuum treatment, especially in the first and second runs. Results from the second and third runs are shown in FIG. 3. In the third run, three out of four of the later time points were low in fermentation gases, and some laboratory workers suggested that they may have allowed air to leak into the sample before measuring it. These samples had more $N_2$ than calculated based on the perfusion rates. Nonetheless, the few abnormal samples were left in the statistical analysis and they did not change the overall trends.

For the vacuum treatment, the $H_2$ was spared from being used to reduce $CO_2$ to make $CH_4$ as evidenced by the lower $CH_4$:$H_2$ ratio. However, it was surprising to find initially that production (µmol) of $CH_4$ was actually higher for the vacuum treatment than the control. In addition, the $CO_2$ production also exceeded that of the control treatment, which started with $CO_2$, and bicarbonate in the media. For the vacuum and $N_2$ perfusion treatments, the media used phosphate buffers in place of bicarbonate.

These results led the present inventor to investigate the source of this additional $H_2$, $CH_4$ and $CO_2$. One possibility is that the feed insoluble organic matter degraded faster and to a greater extent with the vacuum treatment. Another possibility is that the degradation proceeds to a greater extent converting volatile fatty acids into $CH_4$, $CO_2$ and $H_2$.

Figure 4:
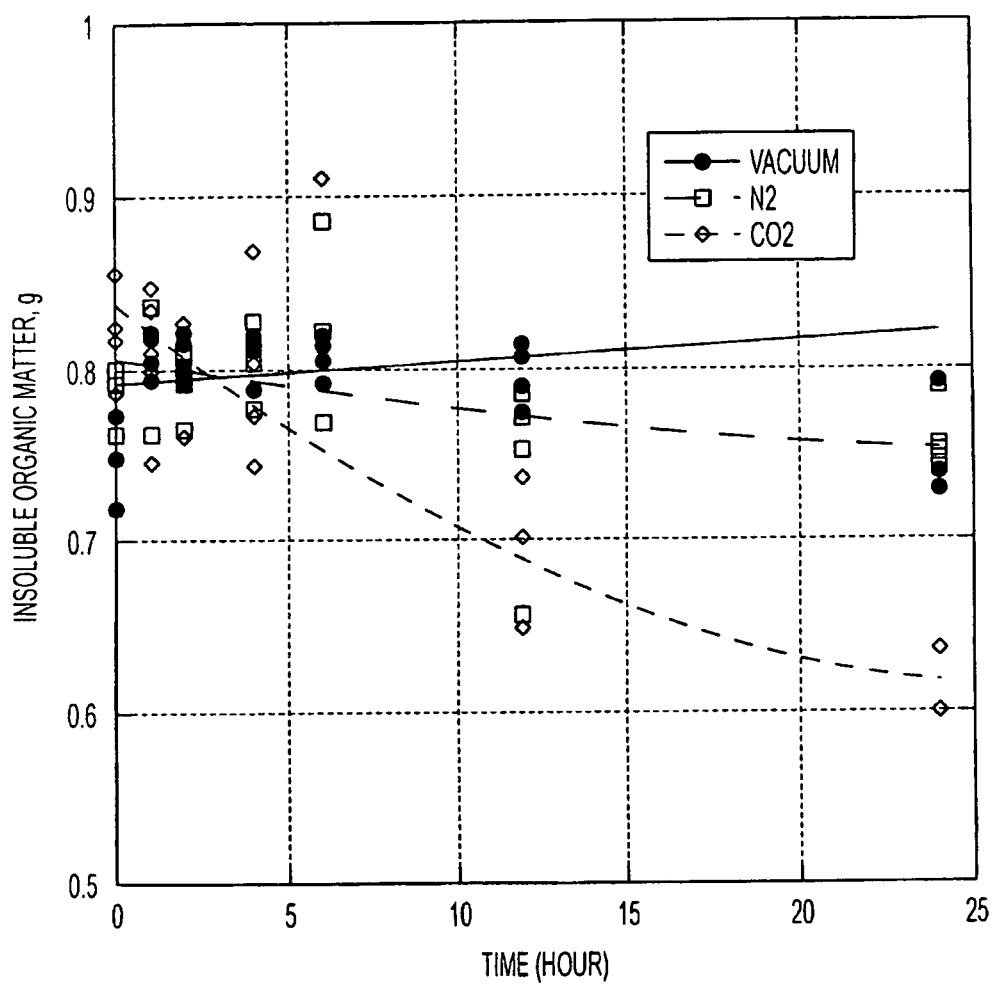
FIG. 4 illustrates the effect of vacuum, $N_2$ perfusion or incubation with $CO_2$ on insoluble organic matter remaining in fermentation flasks.
Figure 5:
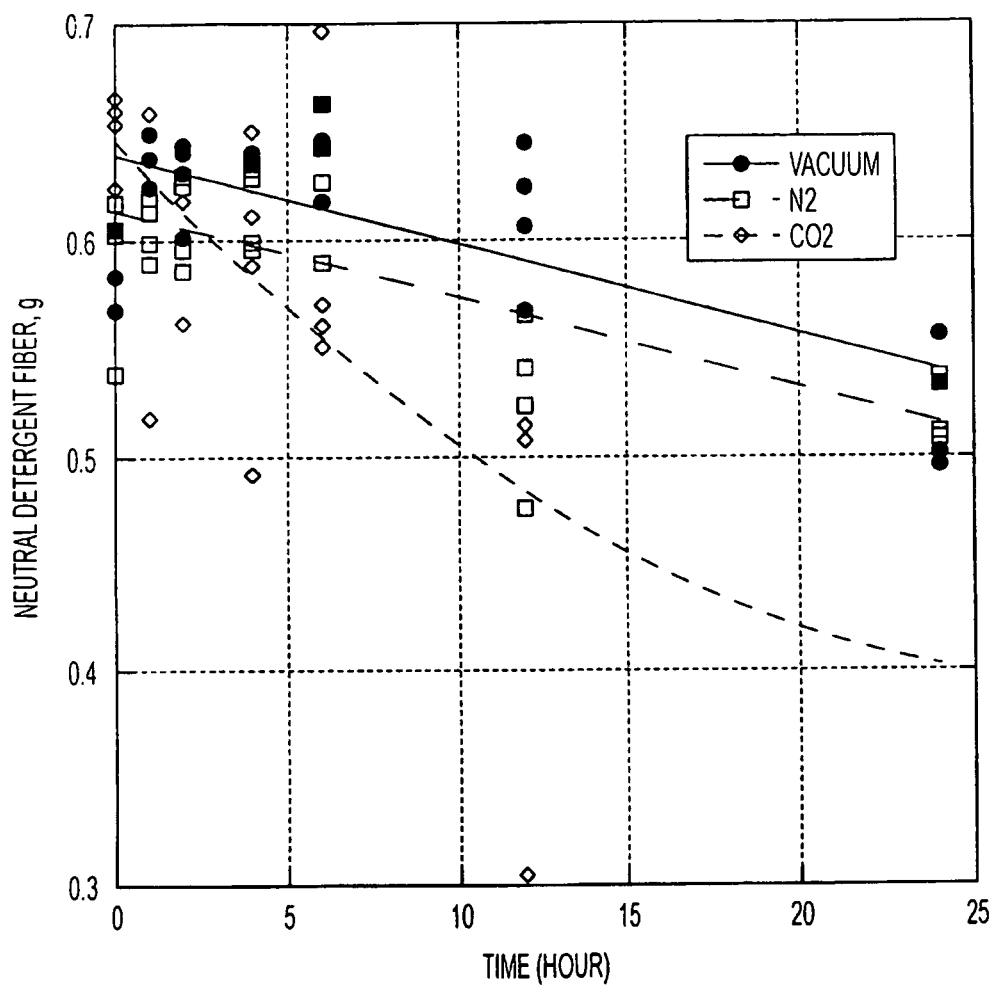
FIG. 5 illustrates the effect of vacuum, $N_2$ perfusion or incubation with $CO_2$ on neutral detergent fiber, i.e., cellulose, hemicellulose and lignin remaining in fermentation tanks.

If the vacuum treatment increased the rate of feed insoluble organic matter degradation to account for the greater $H_2$ and $CH_4$ production, one would expect faster disappearance of insoluble organic matter over time, and greater appearance of volatile fatty acids in that treatment. The opposite occurred. Insoluble organic matter disappeared fastest (P<0.0001) for the control ($CO_2$) treatment and did not change with time for the vacuum treatment (FIG. 4). One possibility is that while digestion proceeded faster, greater microbial growth counterbalanced the insoluble organic matter disappearance for the vacuum treatments. The neutral detergent fiber (cellulose, hemicellulose and lignin), which does not form part of microbial biomass, decreased for all treatments over time, but decreased more slowly for the vacuum (P<0.0001) and $N_2$ perfusion (P<0.05) treatments compared to the control (FIG. 5), suggesting that digestion was actually inhibited by vacuum. The microbial protein could not be measured reliably in the early time points because the $^{15}N$ enrichment of the insoluble protein was not high enough. After 12 or 24 hours incubation, microbial protein was not different (P>0.1) for any treatment or time point (15 mg microbial N; SE=3.4 mg). It is clear that faster degradation of insoluble feed carbohydrates cannot and, thus, does not account for the increase in $H_2$ or $CH_4$ production.

Figure 6:
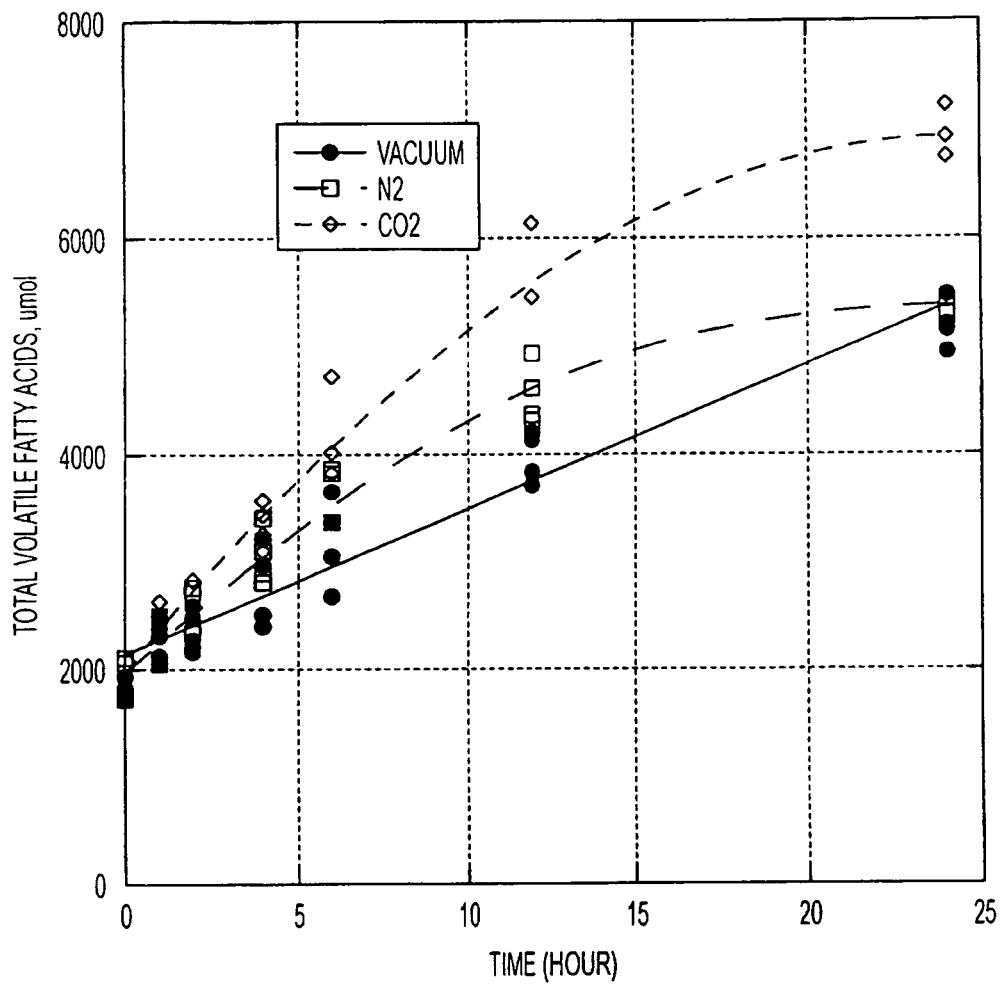
FIG. 6 illustrates the effect of vacuum, $N_2$ perfusion with $CO_2$ on volatile fatty acid production in fermentation flasks.

Given the standard assumption that fermentation gases from the rumen are produced exclusively as a co-product of sugar fermentation to volatile fatty acids (VFA), the treatment with the greatest $H_2$, and $CH_4$ production (vacuum) should have the highest volatile fatty acid production. Again the opposite was the case as shown in FIG. 6. The most rapid production of VFA was produced with the control treatment (P<0.001) with the least production from vacuum, and the $N_2$, perfusion was intermediate.

Figure 7:
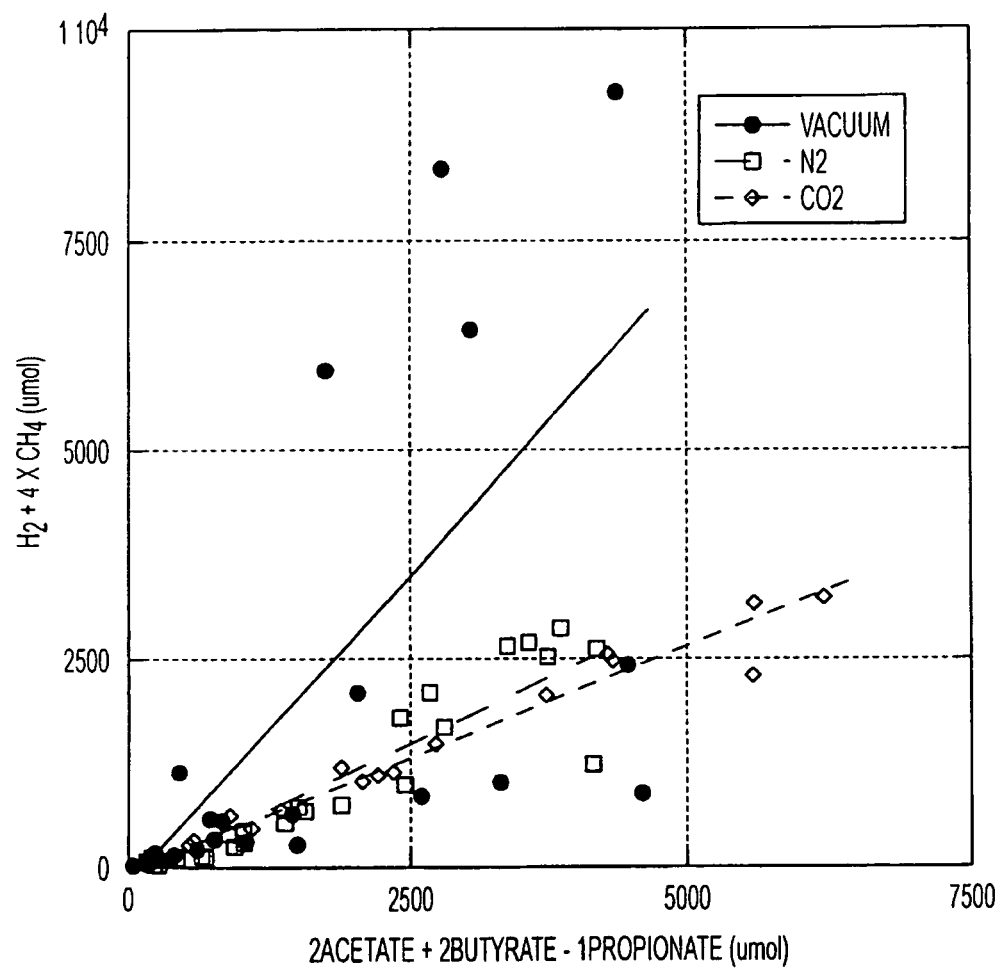
FIG. 7 illustrates the relationship between $H_2$ production and expected $H_2$ production based on volatile fatty acid accumulation.
Figure 8:
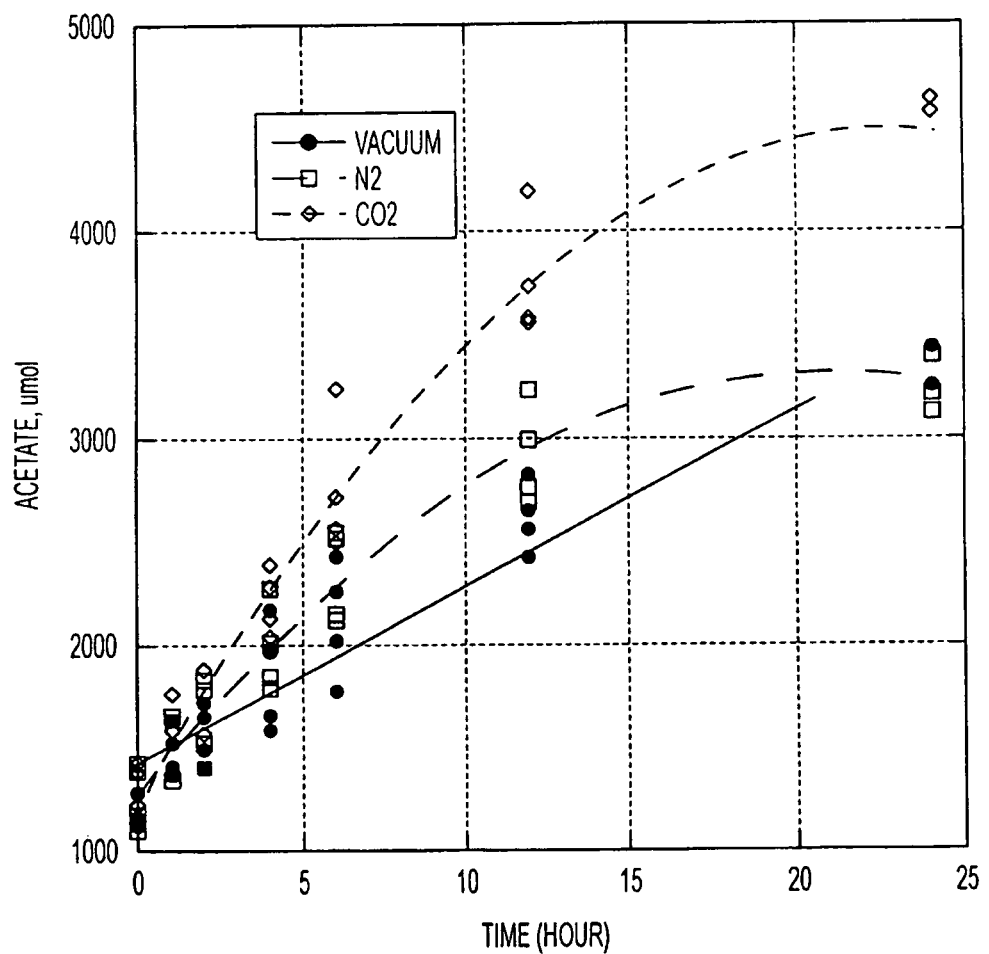
FIG. 8 illustrates the effect of vacuum, $N_2$ perfusion or incubation with $CO_2$ on acetate production in fermentation flasks.
Figure 9:
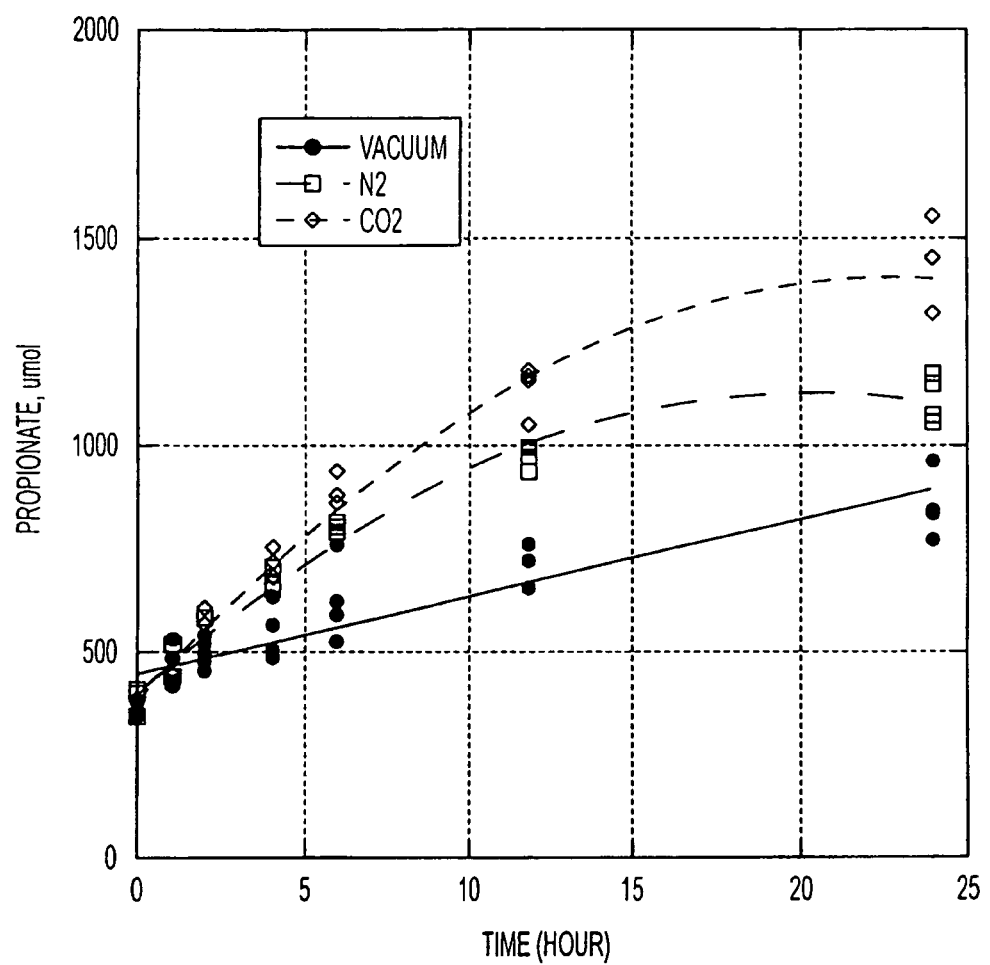
FIG. 9 illustrates the effect of vacuum, $N_2$ perfusion or incubation with $CO_2$ on propionate production in fermentation flasks.

The stoichiometry of gas production from fermentation of sugar to volatile fatty acids provides the final proof that the increased $H_2$ and $CH_4$ production observed in the vacuum treatment does not arise solely from fermentation to acids. Each mole of glucose fermented to 2 moles of acetate would stoichiometrically yield 4 moles of $H_2$; each mole of glucose fermented to butyrate would yield 2 moles of $H_2$; and each mole of glucose fermented to 2 moles of propionate would consume two moles of $H_2$. Therefore, if fermentation of sugars to volatile fatty acids is the predominant source of $H_2$ produced, the moles of $H_2$ produced would equal: 2×acetate+ 2×butyrate−1×propionate. The $H_2$ could be released or converted to $CH_4$ with four moles of $H_2$ consumed per mole of $CH_4$ produced. Therefore, $H_2+4\times CH_4=2\times acetate+2\times butyrate-1\times propionate$. For the control treatment, which was intended to be similar to ruminal conditions, only half as much $H_2$ was apparently recovered in 1-12 and $CH_4$ as was predicted from VFA (FIG. 7). When regressing $H_2$ equivalent against what would be predicted from volatile fatty acids as calculated above, the slope of the regression line was 0.54 (SE=0.02) for the control treatment. For the vacuum treatment, the production of $H_2$ equivalent was greater than predicted from VFA. The slope of the regression line for vacuum treatment was 1.5 (SE=0.33).

Figure 10:
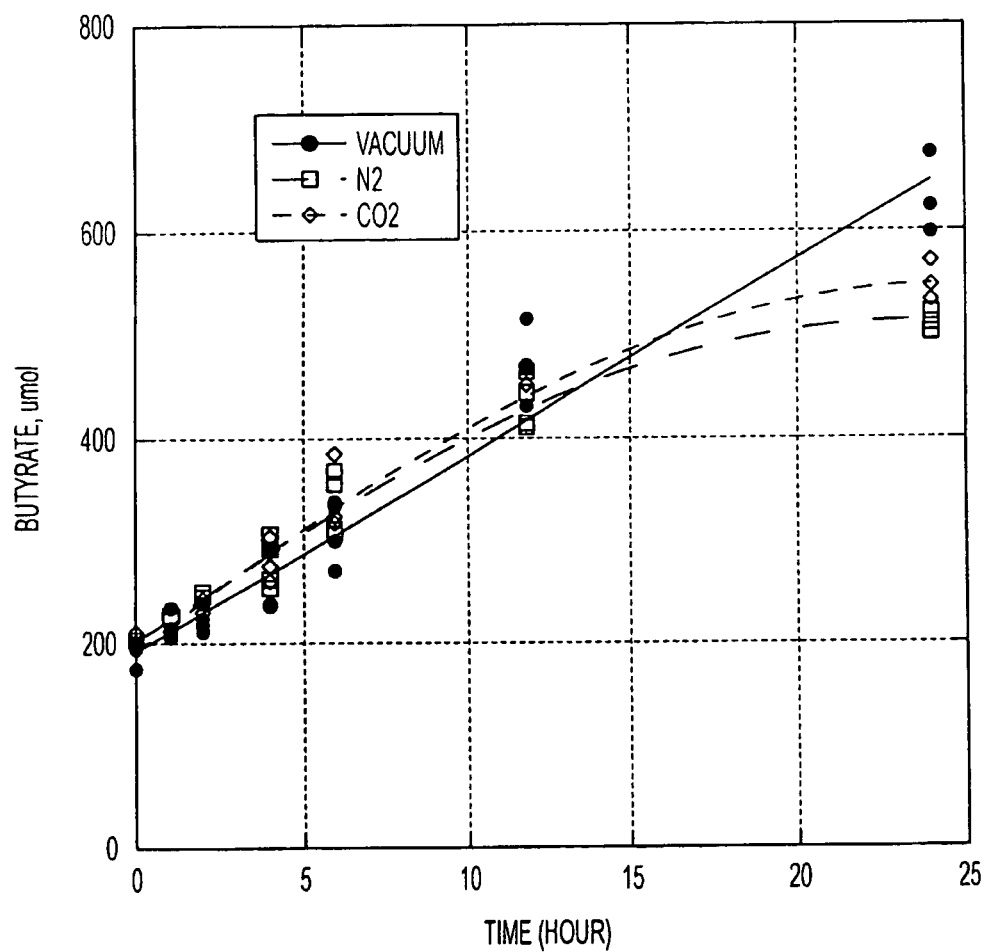
FIG. 10 illustrates the effect of vacuum, $N_2$ perfusion or incubation with $CO_2$ on butyrate production in fermentation flasks.
Figure 11:
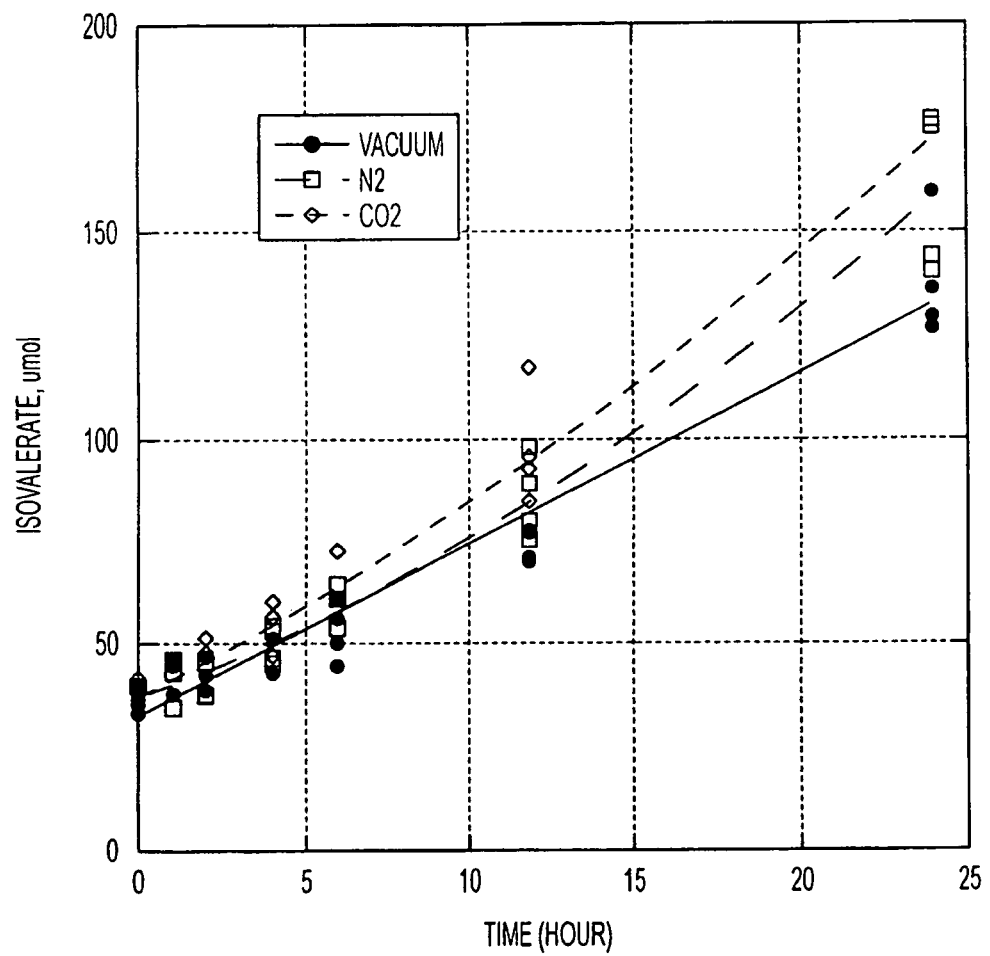
FIG. 11 illustrates the effect of vacuum, $N_2$ perfusion or incubation with $CO_2$ on isovalerate production in fermentation flasks.
Figure 12:
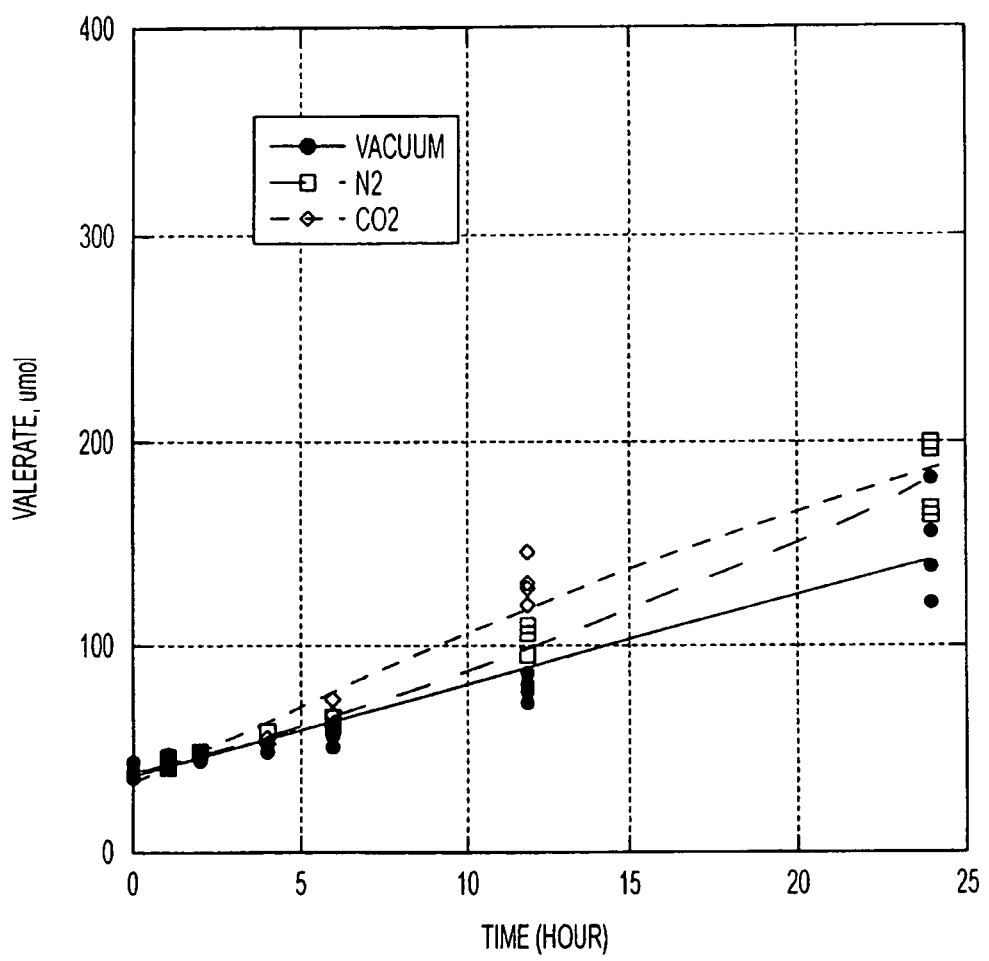
FIG. 12 illustrates the effect of vacuum, $N_2$ perfusion or incubation with $CO_2$ on valerate production in fermentation flasks.
Figure 13:
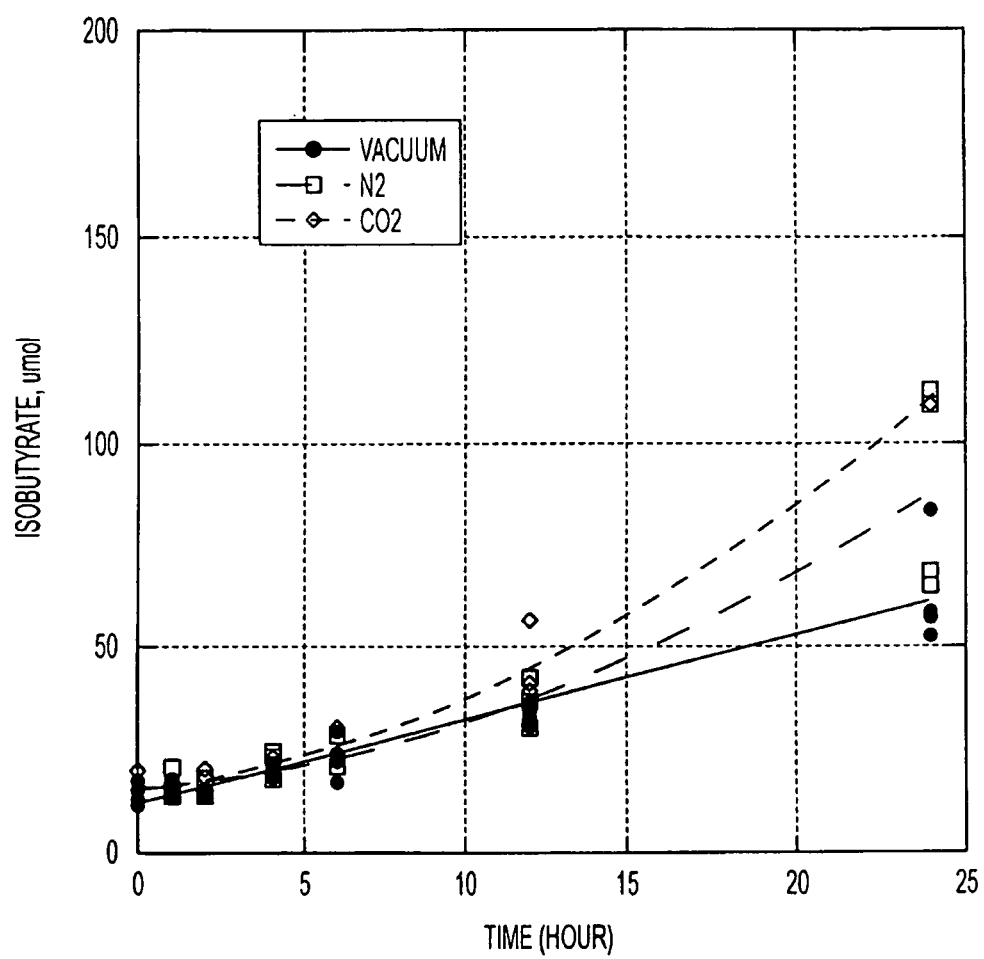
FIG. 13 illustrates the effect of vacuum, $N_2$ perfusion or incubation with $CO_2$ on isobutyrate production in fermentation flasks.
Figure 14:
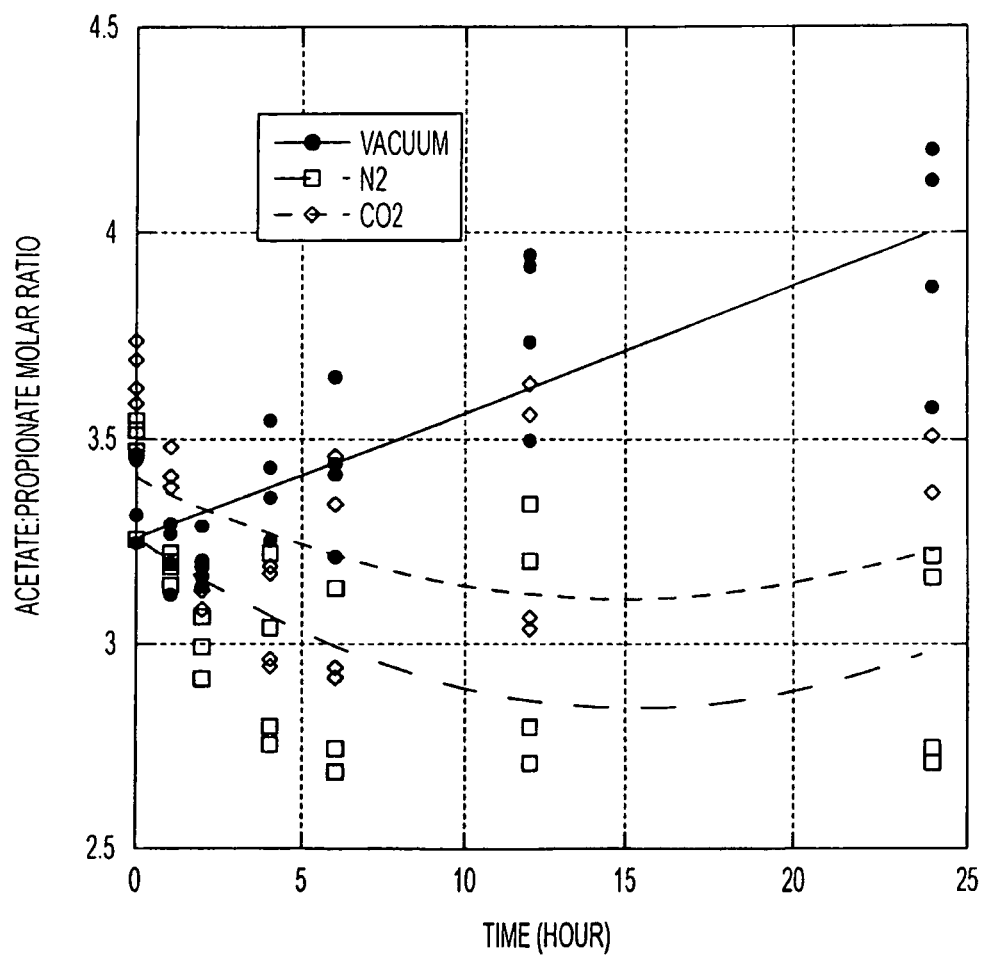
FIG. 14 illustrates the effect of vacuum, $N_2$ perfusion or incubation with $CO_2$ on acetate to propionate molar ratio.
Figure 15:
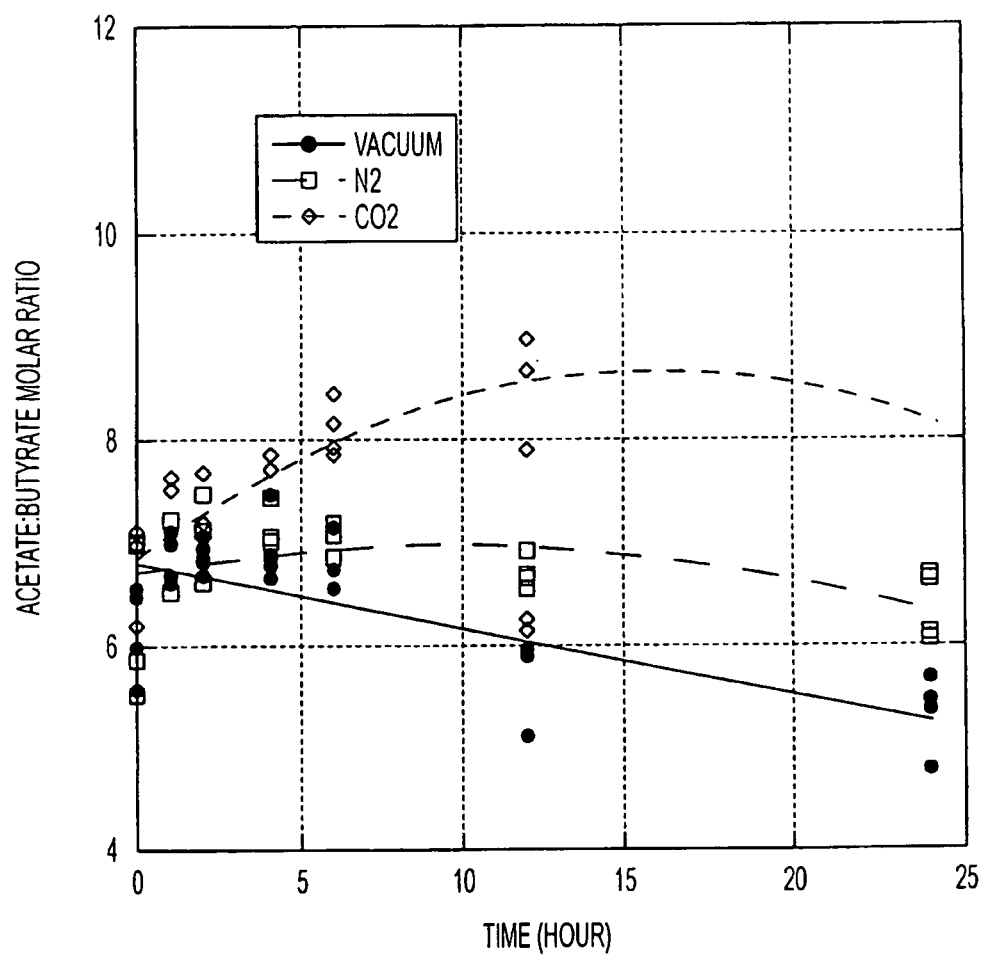
FIG. 15 illustrates the effect of vacuum, $N_2$ perfusion or incubation with $CO_2$ on acetate to butyrate molar ratio in fermentation flasks.

When the profile of volatile fatty acids is considered, further evidence is noted of thermodynamics shifting fermentation. Because of changes in the system's thermodynamics, low $CO_2$ shifts fermentation toward acetate, which spares $H_2$ and $CO_2$ from propionate just as it did from methane. The sparing effect of low $CO_2$ on $H_2$ actually results in the vacuum and $N_2$, perfusion treatments having greater partial pressure of $H_2$. Thus, the additional $H_2$, is used to reduce two acetate molecules to one butyrate, which does not require $CO_2$. The production and profile of fatty acids conform to these theoretical expectations (FIGS. 8-13). Vacuum treatment readily increased butyrate production to a greater concentration than observed for the control treatment (FIG. 10). The acetate to propionate ratio was greatest for the vacuum treatment and least for the control treatment, with the $N_2$ perfusion intermediary between the two (FIG. 14). The opposite was true for the acetate to butyrate ratio (FIG. 15); even as acetate was increased and propionate was inhibited, butyrate increased to use the $H_2$ spared from propionate synthesis.

One of the adaptations of ruminants is to maintain high $CO_2$ pressures by secreting bicarbonate into the rumen; this mechanism keeps the profile of fermentation products stable. By not including bicarbonate in the buffer and removing $CO_2$ as it was produced, fermentation was shifted toward volatile fatty acids whose production releases $CO_2$—acetate and butyrate—and away from propionate, which does not.

Part of the decrease in volatile fatty acid production would have resulted from the lower insoluble organic matter degradation. Part of the decrease was due to the degradation of volatile fatty acids to $CO_2$, $CH_4$ and $H_2$. Methanogenesis from volatile fatty acids is known to occur slowly in methane digesters, but was thought not to occur in the rumen because these slowgrowing organisms would wash out of the rumen.

These results are similar to those from a preliminary experiment that was described earlier in a provisional patent application, i.e. U.S. Ser. No. 60/870,441. The much greater production of $H_2$, $CH_4$ and $CO_2$ with the vacuum, and in that case $N_2$ perfusion, was associated with a decrease in volatile fatty acid accumulation, and the volatile fatty acid amount measured at six hours was actually less than was measured at four hours. The subsequent experiment described here, and other experiments in this report, confirm that volatile fatty acids can be degraded to $H_2$, $CH_4$ and $CO_2$, using rumen microbes if the conditions of fermentation are altered to make that degradation thermodynamically feasible.

Methane has been considered to be made exclusively from reduction of $CO_2$ in the rumen, and the H, for this reduction was thought to be generated with glucose fermentation to volatile fatty acids. The results of this experiment demonstrate the truth of these assumptions for rumen fluid incubated in conditions similar to the rumen (control). The type of microbial activity in the rumen was thought to prevent degradation of volatile fatty acids to $H_2$ and $CH_4$. The present inventor has demonstrated that thermodynamics is the limiting factor, not microbial activity. This experiment shows that the microbial activity of the rumen is readily able to produce $H_2$ and $CH_4$ from other products (including volatile fatty acids) when thermodynamics is altered by changing partial pressures of fermentation gases with vacuum or $N_2$ perfusion.

The implications for this discovery extend beyond rumen fermentation. Degradation of volatile fatty acids can be accelerated by removal of fermentation gases to produce $H_2$, and $CH_4$. This method is likely to be as effective with manure digesters as it was with our digesters inoculated with rumen fluid. Thus, application of vacuum or perfusion gases can increase the concentration of $H_2$ produced, increase $CH_4$ production rates, and accelerate degradation of volatile fatty acids. In practice, $H_2$ could be removed from fermentation gases in digesters based on its reactivity as a reducing agent or its small molecular size. In either case, removing $H_2$ would shift fermentation and result in greater $H_2$ release. Other methods to increase $CH_4$ and $H_2$ production and further accelerate gas production will be described based on the results of other experiments.

Example 2

Effect of Gas Pressure on Digestion and Gas Production

An experiment was conducted to compare the level of vacuum pressure on production of fermentation gases, volatile fatty acids, alcohols, and the degradation of substrate. Four levels of total gas pressure were compared: 0.07 atm (as for previous experiment), 0.25 atm, 1 atm, or greater than 1 atm. The moderate pressure was controlled by attaching a solenoid valve to the vacuum line. This valve was wired to a vacuum switch that was set to open the line to the vacuum when the pressure exceeded 0.33 atm and close when it fell to 0.25 atm. The 1-atm treatment was achieved by connecting a mylar balloon to the flask. The >1-atm treatment was achieved by incubating the samples in 125-ml Wheaton bottles closed with a crimp to allow gas pressure to build up.

In most other respects, this experiment was similar to the previous one except half as much timothy grass hay (0.5 g) was incubated in 125-ml flasks with 40 ml phosphate-buffered media with 10 ml rumen fluid for 24 h. Total gas production was measured, mixed, sampled, and analyzed for $N_2$, $CO_2$, $CH_4$ and $H_2$. The liquid was sampled at the end of the 24-h incubation period and analyzed for volatile fatty acids and alcohols. The entire residue after-incubation was analyzed for neutral detergent fiber (NDF).

Results

In this experiment, leakage into the vacuum system was better controlled than in the previous experiment so the $H_2$ and $CH_4$ were concentrated as a percentage of all gases in the flask by the end of the incubation in the high vacuum treatment (data not shown in tables). However, when these sampled gases were diluted with the $N_2$ that was initially removed from the system, the overall concentrations were lower as shown in Table 2. Both $H_2$ and $CH_4$ production were lower for the vacuum treatments than for the treatments under 1 atmosphere or more of pressure. These results demonstrate that although methane and hydrogen concentration can be increased during fermentation by applying vacuum, the increased production rates seen for the vacuum treatment in the previous experiment compared to the control cannot be explained by the low pressure.

The gas production rates were lower, although treatment effects were more evident, for incubation of volatile fatty acid mixtures (Table 2) compared to the incubation of timothy hay (Table 3). With such low amounts of gases produced, it is not clear that the gases were produced from volatile fatty acids or from substrate in the rumen inocula.

Redox potential ($E_h$) was more negative for the vacuum treatments with incubation of both volatile fatty acids and hay (Tables 4 and 5), which relates to the greater $H_2$ equivalent under-vacuum. Hydrogen is a function of pH and redox potential. As $H_2$ and $CO_2$ are removed from the headspace by applying vacuum, the $H_2$ concentration increases to compensate for the decrease in $CO_2$ and to move the system back toward equilibrium. Because the concentration is low for the $H_2$, the concentration of $H_2$ changes a much greater percentage than for the other gases.

The orchestrated interconversion of volatile fatty acids shown in the previous experiment was repeated again in the present experiment as shown in Tables 4 and 5. Application of vacuum shifted fermentation away from propionate and toward acetate and butyrate. The effects were greatly diminished for the incubations with volatile fatty acid solutions. This suggests that interconversion is a process that occurs in conjunction with feed fermentation of sugar and may not occur as much when other substrate is limited.

The $H_2$ equivalent produced ($H_2+4 \times CH_4$) was least for the vacuum treatments (Table 2 and 3) and the stoichiometric expectation of $H_2$ production from fermentation of hexose to volatile fatty acid (2×acetate+2×butyrate−1×propionate) was also least for the vacuum treatments (Tables 4 and 5). Thus, the ratio of the first to the second was similar for the vacuum treatments when fermenting timothy hay.

This experiment shows that the application of vacuum causes shifts in volatile fatty acid profiles seen previously, but not the increase in $H_2$ or $CH_4$ observed then. The increase in $H_2$ or $CH_4$ for vacuum in the first experiment may have resulted from the use of $N_2$ to replace $CO_2$.

One additional piece of information from this experiment relates to the neutral detergent fiber (NDF) digestion. Application of high vacuum inhibited fiber digestion in the previous experiment as in this experiment (Table 5). However, moderate vacuum only slightly inhibited fiber degradation while many of the desired effects were still observed. Therefore, application of slight vacuum (e.g. 0.25 atm) is a means to shift fermentation without having much impact on fiber digestion In addition to the greater production of $H_2$ and $CH_4$ and the shift in fermentation acid profiles and amount, we also observed production of ethanol in the vacuum treatments (Table 6). There was additional ethanol recovered in the distillate for the vacuum treatment, demonstrating the practice of vacuum distillation during fermentation. Ethanol is not normally observed in the rumen and can be fatal to the animal when it is produced in high amounts. In the animal, carbon dioxide is available and is secreted into the rumen as bicarbonate; it is used for methanogenesis and shifts volatile fatty acid production toward propionate. These processes consume hydrogen. With less carbon dioxide, such as with the $N_2$ perfused treatment, and especially with vacuum, the $H_2$ cannot be used in these pathways and instead builds up until it can be used to reduce acetate to ethanol. It may also convert propionate to ethanol and produce $CO_2$. Regardless of the pathway, in the normal rumen, ethanol is not thermodynamically feasible and the pathways to produce it cannot compete with those for methane or volatile fatty acids. We were able to produce ethanol by changing these conditions. We also observed small concentrations of 1-propanol.

TABLE 2

Concentration and production of molecular hydrogen ($H_2$), methane ($CH_4$) and carbon dioxide ($CO_2$) after incubating volatile fatty acid solutions with ruminal microorganisms for 24 h in $N_2$ at different pressures.

| | Pressure (atm.)[1] | | | | | |
| --- | --- | --- | --- | --- | --- | --- |
| | 0.07 | 0.25 | 1.0 | >1.0 | SE[2] | P<[3] |
| $H_2$ (% of all gases)[4] | 0.003 | 0.000 | 0.003 | 0.002 | 0.0012 | 0.4 |
| $H_2$ (% of fermentation gas)[5] | 0.032 | 0.000 | 0.035 | 0.018 | 0.0128 | 0.3 |
| $CH_4$ (% of all gases) | 0.094 | 0.030 | 0.232 | 0.554 | 0.032 | 0.0001 |
| $CH_4$ (% of fermentation gas) | 0.98 | 2.34 | 2.51 | 7.14 | 0.473 | 0.0001 |
| $CO_2$ (% of all gases) | 3.84 | 2.54 | 9.21 | 7.40 | 0.739 | 0.0008 |
| $CO_2$ (% of fermentation gas) | 97.6 | 99.0 | 97.4 | 92.8 | 0.471 | 0.0001 |
| $CH_4$:$H_2$ (molar ratio) | 72 | — | 49 | 127 | 10.1 | 0.08 |

TABLE 2-continued

Concentration and production of molecular hydrogen ($H_2$), methane ($CH_4$) and carbon dioxide ($CO_2$) after incubating volatile fatty acid solutions with ruminal microorganisms for 24 h in $N_2$ at different pressures.

| | Pressure (atm.)[1] | | | | | |
|---|---|---|---|---|---|---|
| | 0.07 | 0.25 | 1.0 | >1.0 | SE[2] | P<[3] |
| $CH_4:CO_2$ (molar ratio) | 0.0024 | 0.010 | 0.026 | 0.077 | 0.0051 | 0.0001 |
| $H_2$ production (µmol) | 0.00 | 0.05 | 0.11 | 0.19 | 0.39 | 0.05 |
| $CH_4$ production (µmol) | 3.5 | 7.4 | 14.1 | 17.7 | 1.56 | 0.001 |
| $CO_2$ production (µmol) | 588 | 291 | 278 | 237 | 47 | 0.003 |
| $H_2$ equivalent ($H_2 + 4\,CH_4$) | 14.1 | 29.6 | 56.6 | 70.9 | 6.15 | 0.001 |
| Efficiency ($H_2$ eqiv/($CO_2 + CH_4$)) | 0.39 | 0.94 | 0.10 | 0.29 | 0.019 | 0.0001 |

[1]Treatments were fermentation under vacuum pressure (0.07 atm), moderate vacuum pressure, or with $N_2$ and gases allowed to expand to a mylar balloon, or maintained under ressure in a wheaton bottle.
[2]Standard error of the mean, n = 3 per treatment.
[3]Significance of treatment effect
[4]Molar percentage among all gases including initial $N_2$ removed by vacuum.
[5]Molar percentage among fermentation gases including perfused $CO_2$, excluding $N_2$.

TABLE 3

Concentration and production of molecular hydrogen ($H_2$), methane ($CH_4$) and carbon dioxide ($CO_2$) after incubating timothy hay with ruminal microorganisms for 24 h in $N_2$ at different pressures.

| | Pressure (atm.)[1] | | | | | |
|---|---|---|---|---|---|---|
| | 0.07 | 0.25 | 1.0 | >1.0 | SE[2] | P<[3] |
| $H_2$ (% of all gases)[4] | 0.024 | 0.063 | 0.175 | 0.125 | 0.023 | 0.02 |
| $H_2$ (% of fermentation gases)[5] | 0.288 | 0.332 | 0.612 | 0.392 | 0.061 | 0.03 |
| $CH_4$ (% of all gases) | 0.84 | 0.86 | 4.71 | 6.52 | 0.153 | 0.001 |
| $CH_4$ (% of fermentation gas) | 8.6 | 10.5 | 16.3 | 20.4 | 1.31 | 0.001 |
| $CO_2$ (% of all gases) | 7.0 | 11.4 | 24.0 | 23.3 | 2.63 | 0.003 |
| $CO_2$ (% of fermentation gas) | 91.1 | 88.7 | 83.1 | 79.2 | 1.42 | 0.002 |
| $CH_4:H_2$ (molar ratio) | 21.9 | 27.6 | 28.8 | 56.0 | 7.444 | 0.05 |
| $CH_4:CO_2$ (molar ratio) | 0.095 | 0.12 | 0.19 | 0.26 | 0.016 | 0.004 |
| $H_2$ production (µmol) | 5.1 | 9.9 | 7.4 | 5.0 | 2.48 | 0.5 |
| $CH_4$ production (µmol) | 140 | 148 | 200 | 259 | 13.6 | 0.001 |
| $CO_2$ production (µmol) | 1856 | 1256 | 1022 | 1006 | 375 | 0.4 |
| $H_2$ equivalent ($H_2 + 4\,CH_4$) | 566 | 615 | 807 | 1041 | 58 | 0.003 |
| Efficiency ($H_2$ eqiv/($CO_2 + CH_4$)) | 0.35 | 0.40 | 0.66 | 0.82 | 0.054 | 0.002 |

[1]Treatments were fermentation under vacuum pressure (0.07 atm), moderate vacuum pressure, or with $N_2$ and gases allowed to expand to a mylar balloon, or maintained under pressure in a Wheaton bottle.
[2]Standard error of the mean, n = 3 per treatment.
[3]Significance of treatment effect
[4]Molar percentage among all gases including initial $N_2$ removed by vacuum.
[5]Molar percentage among fermentation gases including perfused $CO_2$, excluding $N_2$.

TABLE 4

Volatile fatty acids (VFA) per flask after incubation of VFA solutions with ruminal microorganisms at different gas pressures for 24 h.

| | T = 0[2] | Pressure (atm.)[1] | | | | SE[3] | Time P<[4] | Trt P<[5] |
|---|---|---|---|---|---|---|---|---|
| | | 0.07 | 0.25 | 1.0 | >1.0 | | | |
| pH | 6.7 | 6.8 | 6.8 | 6.7 | 6.6 | 0.0 | 0.63 | 0.0001 |
| Eh, mV | −108 | −166 | −211 | −175 | −154 | 11.7 | 0.01 | 0.04 |
| Total VFA, µmol | 7661 | 7869 | 7795 | 7945 | 8227 | 122 | 0.05 | 0.23 |
| Acetate, µmol | 5080 | 5211 | 5147 | 5265 | 5459 | 85 | 0.06 | 0.22 |
| Propionate, µmol | 1456 | 1485 | 1477 | 1499 | 1553 | 22 | 0.08 | 0.20 |
| Butyrate, µmol | 784 | 808 | 805 | 813 | 838 | 11 | 0.02 | 0.30 |
| Isovalerate, µmol | 137 | 145 | 147 | 146 | 149 | 1.8 | 0.001 | 0.37 |
| Valerate, µmol | 148 | 155 | 153 | 157 | 162 | 1.9 | 0.006 | 0.1 |
| Isobutyrate, µmol | 56.3 | 64.3 | 66.0 | 65.3 | 65.3 | 2.0 | 0.0003 | 0.97 |
| Acetate:Propion, mole ratio | 3.48 | 3.50 | 3.48 | 3.51 | 3.51 | 0.10 | 0.12 | 0.60 |

TABLE 4-continued

Volatile fatty acids (VFA) per flask after incubation of VFA solutions with ruminal microorganisms at different gas pressures for 24 h.

| | | Pressure (atm.)[1] | | | | | Time | Trt |
|---|---|---|---|---|---|---|---|---|
| | T = 0[2] | 0.07 | 0.25 | 1.0 | >1.0 | SE[3] | P<[4] | P<[5] |
| Acetate:Butyrate, mole ratio | 6.48 | 6.84 | 6.39 | 6.48 | 6.51 | 0.34 | 0.79 | 0.38 |
| 2Acet + 2Butyr − Propion[6] | 0 | 282 | 155 | 386 | 768 | 170 | 0.05 | 0.24 |

[1]Treatments were fermentation under vacuum pressure (0.07 atm), moderate vacuum pressure, or with $N_2$ and gases allowed to expand to a mylar balloon, or maintained under pressure in a Wheaton bottle.
[2]Initial measured concentration
[3]Standard error of the mean, n = 3 per treatment.
[4]Significance of the effect of time (0 vs. 24 h)
[5]Significance of treatment effect.
[6]Estimated production of $H_2$ equivalent from fermentation of sugar to VFA, 2 times acetate and butyrate production in minus propionate production.

TABLE 5

Volatile fatty acids (VFA) per flask after incubation of timothy hay (0.5 g) with ruminal microorganisms at different gas pressures for 24 h.

| | | Pressure (atm.)[1] | | | | | Time | Trt |
|---|---|---|---|---|---|---|---|---|
| | T = 0[2] | 0.07 | 0.25 | 1.0 | >1.0 | SE[3] | P<[4] | P<[5] |
| pH | 6.7 | 6.5 | 6.4 | 6.3 | 6.0 | 0.04 | 0.003 | 0.0001 |
| Eh | −135 | −230 | −258 | −197 | −153 | 12.6 | 0.03 | 0.002 |
| Total VFA, μmol | 785 | 1646 | 1881 | 2004 | 2068 | 30 | 0.0001 | 0.0001 |
| Acetate, μmol | 569 | 1129 | 1237 | 1289 | 1337 | 21.4 | 0.0001 | 0.002 |
| Propionate, μmol | 132 | 307 | 454 | 523 | 532 | 6.0 | 0.0002 | 0.0001 |
| Butyrate, μmol | 73 | 160 | 152 | 159 | 166 | 3.3 | 0.0001 | 0.17 |
| Isovalerate, μmol | 4.7 | 16.3 | 10.5 | 8.3 | 8.0 | 0.53 | 0.02 | 0.0001 |
| Valerate, μmol | 2.7 | 21.3 | 18.0 | 18.3 | 19.7 | 0.53 | 0.0001 | 0.02 |
| Isobutyrate, μmol | 3.0 | 12.3 | 9.0 | 6.3 | 4.7 | 0.43 | 0.03 | 0.0001 |
| Acetate:Propion, mole ratio | 4.3 | 3.7 | 2.7 | 2.5 | 2.5 | 0.028 | 0.0007 | 0.0001 |
| Acetate:Butyrate, mole ratio | 7.7 | 7.0 | 8.1 | 8.1 | 8.1 | 0.08 | 0.86 | 0.0001 |
| 2Acet + 2Butyr − Propion[6] | 0 | 1120 | 1174 | 1220 | 1321 | 44 | 0.0001 | 0.07 |
| NDF remaining (% of DM)[8] | 57.8 | 53.5 | 44.1 | 41.5 | 39.0 | 0.23 | 0.0001 | 0.0001 |

[1]Treatments were fermentation under vacuum pressure (0.07 atm), moderate vacuum pressure, or with $N_2$ and gases allowed to expand to a mylar balloon, or maintained under pressure in a Wheaton bottle.
[2]Initial measured concentration
[3]Standard error of the mean, n = 3 per treatment.
[4]Significance of the effect of time (0 vs. 24 h)
[5]Significance of treatment effect.
[6]Estimated production of $H_2$ equivalent from fermentation of sugar to VFA, 2 times acetate and butyrate production in μmol minus propionate production.
[7]$H_2$ equivalent measured from gas production ($H_2$ + 4 × $CH_4$) divided by $H_2$ expected from fermentation of glucose to VFA (2Acetate + 2Butyrate − Propionate).
[8]Neutral detergent fiber (cellulose, hemicellulose, lignin) analyzed as a percentage of initial dry matter.

TABLE 6

Alcohols[1] per flask after incubation with volatile fatty acids or timothy hay (0.5 g) with ruminal microorganisms at different gas pressures for 24 h.

| | Pressure (atm.)[2] | | | | | |
|---|---|---|---|---|---|---|
| | 0.07 | 0.25 | 1.0 | >1.0 | SE[3] | P<[4] |
| Incubation of volatile fatty acids | | | | | | |
| Ethanol, μmol | 31 | 32 | 19 | 18 | 5.0 | 0.17 |
| 1-propanol, μmol | 0 | 0 | 0 | 0 | — | — |
| Incubation of timothy hay | | | | | | |
| Ethanol, μmol | 58 | 34 | 36 | 30 | 6.1 | 0.05 |
| 1-propanol, μmol | 7 | 0 | 3 | 0 | 3.0 | 0.36 |

[1]Isopropyl-alcohol and 1-butanol were measured but not detected.
[2]Treatments were fermentation under vacuum pressure (0.07 atm), moderate vacuum pressure, or with $N_2$ and gases allowed to expand to a mylar balloon, or maintained under pressure in a Wheaton bottle.
[3]Standard error of the mean, n = 3 per treatment.
[4]Significance of treatment effect.

Example 3

Gas Composition and Pressure

Whereas previous experiments showed that hydrogen production was increased with gas perfusion to maintain a constant partial pressure of hydrogen, an experiment was conducted with greater perfusion rates to determine if greater $H_2$ production could be obtained, and what other shifts in metabolism would occur to support the greater $H_2$ production. Treatments included a control in which samples were maintained under moderate Vacuum (0.25 atm) starting with $N_2$ gas in the headspace but without gas perfusion, and a set of controls starting with $N_2$, $CO_2$, air, or $H_2$ in the headspace but without perfusion. In other treatments, gases were perfused through the headspace at regular time intervals (T=2, 4, 6, 8 12 h) either with moderate vacuum applied after the perfusion ($N_2$, $CO_2$, or air), or not ($N_2$, $CO_2$, air, or $H_2$). For perfusions at 1 atm pressure, 200 ml gas (88 ml at 1 atm) was removed from the 250-ml flask and forced into the collection balloon, after which perfusion gas was allowed to replace the removed gas to reestablish 1 atmosphere total pressure. For the vacuum perfusions, 200 ml of perfusion gas was allowed into the incubation flask and was then immediately removed by vacuum pump. These perfusion rates were considerably higher than for previous experiments, and the larger flasks increased the headspace for gases from the fermentation to equilibrate.

Gases were sampled from the balloons above the flasks as well as from the flasks themselves, and production of fermentation gases was calculated as the total gas volume in the balloon times the concentration of $H_2$, $CH_4$ or $CO_2$ plus the volume of gas in the flask at 1 atm equivalent pressure times the concentration in the flask. Concentrations reported are for the average concentration of all gases that were collected or left in the flask.

Perfusion of different gases with moderate vacuum (0.25 atm) decreased $H_2$ concentration (Table 7) of collected gases at atmospheric pressure. The flasks treated with vacuum perfusion were infused with gas periodically, and then gases were immediately collected under vacuum to wash out the fermentation gas. Thus, the concentration of collected gas was reduced by a factor of three from this dilution process. However, the application of vacuum pressure (0.25 atm) would have reduced the partial pressure by a factor of four from what would have been measured at atmospheric pressure. In this study, the vacuum treatment without perfusion also had low concentrations of $H_2$ or $CH_4$ because the initial $N_2$ gas that was removed from the sample at the start of the fermentation was included in the collected gas.

Perfusion of gases had little effect on $H_2$ concentration compared to the closed system. This suggests that $H_2$ was readily drawn from the fermentation to replace $H_2$ removed, which was greater for these treatments. The exception was $CO_2$ perfusion in which $H_2$ concentration increased with the perfusion treatment. $H_2$ production was greatest for this treatment as a result of the greater concentration compared to other gases times the similar volume of gas removed. This result was unexpected as the greater amount of $CO_2$ would have increased the feasibility for methane production from $CO_2$ and $H_2$, which should have used $H_2$. On the other hand, greater $CO_2$ may have decreased the degradation of organic matter to $H_2$ and $CO_2$. There was numerically more VFA-C and residual NDF for the $CO_2$ perfusion compared to the closed system (Table 8).

The degradation of VFA and substrate were certainly affected by the perfusions. Perfusion of air resulted in maintenance of $H_2$ concentrations despite the potential for $O_2$ to oxidize substrate including $H_2$. Nearly twice as much $CO_2$ was formed with air perfusion compared to closed air flasks. This suggests that there was a great potential to capture hydrogen equivalent. Total VFA-C was less than 20% as great with air perfusion as for $CO_2$ or $N_2$ perfusion. Degradation of VFA would have provided $H_2$ equivalent, and the demand for $H_2$ could have driven this process.

Capturing the $H_2$ from VFA degradation in a high-energy chemically-reduced product would be technologically useful. Perfusion with $N_2$ did not accomplish this objective in this experiment because VFA-C was not decreased due to the $N_2$ perfusion under atmospheric pressures, and when $N_2$ was perfused under vacuum, the $H_2$ was not captured in greater $H_2$ or $CH_4$ production although VFA-C decreased.

Perfusion with $H_2$ did decrease VFA-C and increase $CH_4$. Although, $H_2$ is not limiting for methane production in this treatment, $CO_2$ is limiting and may have driven the VFA degradation. The proportional changes in $H_2$ concentration with $H_2$ perfusion are greater than changes in $CO_2$ with $CO_2$ perfusion, thus resulting in greater shifts in thermodynamics. The greater energy captured came in part from organic matter degradation to $CO_2$, and although $H_2$ production was not measured, it may have increased in the process. Thus, $H_2$ perfusion could result in greater $CH_4$ production without actual consumption of $H_2$ in the process.

Perfusion of air decreased the degradation of NDF at 24 h but increased the loss of VFA. However, this increased rate of VFA degradation did not result in greater production of $CH_4$. Perfusion with $CO_2$ or $N_2$ increased methane and $H_2$ production sacrificing a small amount of energy captured from VFA degradation. This effect is indicated in the change in efficiency in Table 7. These results suggest that methane digesters can be optimized for rate vs. efficiency by manipulating the gas composition and perfusion rates.

TABLE 7

Concentration and production of molecular hydrogen ($H_2$), methane ($CH_4$) and carbon dioxide ($CO_2$) after incubating timothy hay with ruminal microorganisms at different gas pressures and perfusion rates for 24 h.

| | Vacuum[1] | Vacuum Perfusion[2] | | | Perfusion[3] (1 atm) | | | |
|---|---|---|---|---|---|---|---|---|
| | $N_2$ | $N_2$ | $CO_2$ | Air | $N_2$ | $CO_2$ | Air | $H_2$ |
| $H_2$ (% of all gases) | $0.01^{cd}$ | $0.01^{cd}$ | $0.01^{cd}$ | $0.01^{cd}$ | $0.05^{bcd}$ | $0.13^a$ | $0.09^{ab}$ | 70.5* |
| $H_2$ (% of fermentation gas)[6] | $0.35^{abc}$ | $0.18^{bcd}$ | $0.01^d$ | $0.43^{ab}$ | $0.65^a$ | $0.15^{bcd}$ | $0.61^a$ | 89.1* |
| $CH_4$ (% of all gases) | $0.3^f$ | $0.3^f$ | $0.3^f$ | $0.3^f$ | $1.3^e$ | $1.5^e$ | $0.5^f$ | $2.4^d$ |
| $CH_4$ (% of fermentation gas) | $10.0^d$ | $17.6^b$ | $0.4^i$ | $8.3^{de}$ | $6.8^{ef}$ | $1.6^{hi}$ | $3.1^{gh}$ | $3.0^{gh}$ |
| $CO_2$ (% of all gases) | $3.4^f$ | $3.6^f$ | 78.6* | $2.9^f$ | $6.1^{ef}$ | 89.1* | $13.7^d$ | $7.7^e$ |
| $CO_2$ (% of fermentation gas) | $88^{cd}$ | $93^{ab}$ | 99.6* | $91^{bc}$ | $82^e$ | 98.2* | $96^a$ | $11^h$ |
| $CH_4:H_2$ (molar ratio) | $23^{bcd}$ | $27^{bcd}$ | $40^{bcd}$ | $22^{cd}$ | $36^{bcd}$ | $11^d$ | $6^d$ | 0.04* |
| $CH_4:CO_2$ (molar ratio) | $0.14^e$ | $0.07^{fg}$ | $0.003^h$ | $0.09^f$ | $0.21^d$ | $0.016^g$ | $0.03^g$ | $0.38^b$ |
| $H_2$ production (μmol) | $5.0^c$ | $5.6^{bc}$ | $7.8^{bc}$ | $9.1^{bc}$ | $12.5^{bc}$ | $32.3^a$ | $15.5^b$ | — |
| $CH_4$ production (μmol) | $134^g$ | $218^{def}$ | $272^{cd}$ | $178^{ef}$ | $322^{bc}$ | $383^b$ | $82^g$ | $576^a$ |
| $CO_2$ production (μmol) | $1314^{cd}$ | $3001^a$ | — | $1981^{bc}$ | $1507^{bc}$ | — | $2453^{ab}$ | $1850^{bc}$ |
| $H_2$ equivalent ($H_2$ + 4 $CH_4$) | $603^{ef}$ | $894^{cde}$ | $1094^{bc}$ | $722^{de}$ | $1302^{ab}$ | $1567^a$ | $342^f$ | — |
| Efficiency ($H_2$ equiv/($CO_2$ + $CH_4$)) | $0.48^c$ | $0.28^d$ | — | $0.33^d$ | $0.71^b$ | — | $0.13^e$ | — |

| | Closed[4] (1 atm) | | | | |
|---|---|---|---|---|---|
| | $N_2$ | $CO_2$ | Air | $H_2$ | SE[5] |
| $H_2$ (% of all gases) | $0.06^{bc}$ | $0.05^{bcd}$ | $0.08^b$ | 52.8* | 0.016 |
| $H_2$ (% of fermentation gas)[6] | $0.27^{a-d}$ | $0.05^{cd}$ | $0.25^{bcd}$ | 60.2* | 0.111 |
| $CH_4$ (% of all gases) | $5.5^b$ | $4.8^{bc}$ | $4.4^c$ | $11.8^a$ | 0.23 |
| $CH_4$ (% of fermentation gas) | $22.3^a$ | $5.0^{fg}$ | $12.6^c$ | $13.4^c$ | 0.66 |

TABLE 7-continued

Concentration and production of molecular hydrogen ($H_2$), methane ($CH_4$) and carbon dioxide ($CO_2$) after incubating timothy hay with ruminal microorganisms at different gas pressures and perfusion rates for 24 h.

|  |  |  |  |  |
|---|---|---|---|---|
| $CO_2$ (% of all gases) | 19.0$^c$ | 92.4* | 30.2$^a$ | 23.2$^b$ | 1.34 |
| $CO_2$ (% of fermentation gas) | 77$^f$ | 94.9* | 87$^d$ | 26$^e$ | 1.38 |
| $CH_4:H_2$ (molar ratio) | 61$^{ab}$ | 95$^a$ | 65$^{ab}$ | 0.22* | 14.1 |
| $CH_4:CO_2$ (molar ratio) | 0.29$^c$ | 0.05* | 0.15$^e$ | 0.51$^a$ | 0.014 |
| $H_2$ production (μmol) | 3.0$^c$ | 3.0$^c$ | 3.9$^c$ | — | 3.09 |
| $CH_4$ production (μmol) | 254$^{cde}$ | 339$^{bc}$ | 193$^{def}$ | 392$^b$ | 28.1 |
| $CO_2$ production (μmol) | 879$^d$ | — | 1332$^{cd}$ | 773$^d$ | 273 |
| $H_2$ equivalent ($H_2$ + 4 $CH_4$) | 1024$^{bcd}$ | 1361$^{ab}$ | 777$^{cde}$ | — | 111 |
| Efficiency ($H_2$ equiv/($CO_2$ + $CH_4$)) | 0.90$^a$ | — | 0.51$^c$ | — | 0.045 |

$^{abc}$Means (n = 3) with different superscripts differ (Student T-test; $P < 0.05$)
*Not included in statistical comparison because gas ($H_2$ or $CO_2$) was added as treatment.
[1]Fermentation under moderate vacuum pressure (0.25 atm) starting with $N_2$ headspace.
[2]Moderate vacuum pressure with intermittent perfusion of gases ($N_2$, $CO_2$, air or $H_2$)
[3]Perfusion of gases without application of moderate vacuum
[4]Incubation at 1 atm without vacuum or perfusion of gases.
[5]Standard error of the mean, n = 3 per treatment.
[6]Molar percentage among fermentation gases, excluding $N_2$.

TABLE 8

Volatile fatty acids (VFA) per flask after incubation of timothy hay (0.5 g) with ruminal microorganisms at different gas pressures and perfusion rates for 24 h.

| | Vacuum[1] | Vacuum Perfusion[2] | | | Perfusion[3] (1 atm) | | | |
|---|---|---|---|---|---|---|---|---|
| | $N_2$ | $N_2$ | $CO_2$ | Air | $N_2$ | $CO_2$ | Air | $H_2$ |
| pH | 6.9$^{c-e}$ | 6.7$^{def}$ | 7.7$^a$ | 7.0$^{b-e}$ | 6.6$^{efg}$ | 7.3$^{ab}$ | 7.1$^{bcd}$ | 6.9$^{c-f}$ |
| Eh | −210$^{abc}$ | −201$^{ab}$ | −244$^c$ | −225$^{abc}$ | −190$^a$ | −241$^c$ | −200$^{ab}$ | −227$^{abc}$ |
| Total VFA, μmol | 1541$^{cde}$ | 1044$^{ef}$ | 1619$^{cde}$ | 906$^{fg}$ | 2566$^{ab}$ | 2707$^a$ | 392$^g$ | 1870$^{cd}$ |
| Acetate, μmol | 935$^{cd}$ | 501$^{ef}$ | 978$^{cd}$ | 355$^f$ | 1534$^{ab}$ | 1721$^a$ | 102$^f$ | 1025$^{cd}$ |
| Propionate, μmol | 385$^d$ | 334$^{de}$ | 425$^{bcd}$ | 365$^d$ | 670$^a$ | 658$^a$ | 187$^c$ | 549$^{abc}$ |
| Butyrate, μmol | 131$^b$ | 124$^b$ | 126$^b$ | 100$^b$ | 252$^a$ | 218$^a$ | 28$^c$ | 198$^a$ |
| Isovalerate, μmol | 16.6$^{de}$ | 15.1$^{ef}$ | 16.3$^{def}$ | 15.6$^{ef}$ | 20.2$^{abc}$ | 22.4$^{ab}$ | 10.3$^g$ | 19.4$^{bcd}$ |
| Valerate, μmol | 60.0$^{cde}$ | 59.0$^{de}$ | 61.0$^{cde}$ | 59.0$^{de}$ | 74.0$^a$ | 68.5$^{ab}$ | 56.4$^e$ | 64.1$^{bcd}$ |
| Isobutyrate, μmol | 12.5$^{cde}$ | 11.0$^e$ | 12.2$^{cde}$ | 11.7$^{de}$ | 15.2$^{abc}$ | 18.5$^a$ | 7.0$^f$ | 14.1$^{bcd}$ |
| Total VFA-C, μmol | 3985$^{bcd}$ | 2912$^d$ | 4170$^{bcd}$ | 2622$^{de}$ | 6620$^a$ | 6817$^a$ | 1242$^e$ | 4763$^{cde}$ |
| Acetate:Propion, mole ratio | 2.20$^{ab}$ | 1.51$^{bc}$ | 2.32$^{ab}$ | 0.98$^c$ | 2.29$^{ab}$ | 2.65$^a$ | 0.76$^c$ | 1.91$^{ab}$ |
| Acetate:Butyrate, mole ratio | 6.63$^{ab}$ | 3.96$^{ab}$ | 7.80$^{ab}$ | 3.66$^b$ | 6.08$^{ab}$ | 7.93$^{ab}$ | 9.20$^a$ | 5.34$^{ab}$ |
| 2Acct + 2Butyr − Propion[6] | 1749$^{cde}$ | 915$^{ef}$ | 1783$^{cde}$ | 544$^{fg}$ | 2902$^{ab}$ | 3220$^a$ | 74$^g$ | 1897$^{bc}$ |
| $H_2$ equiv/$H_2$ w/ VFA[7] | 0.90 | 1.57 | 0.54 | 1.35 | 0.45 | 0.49 | 0.5 | — |
| NDF remaining (% of DM)[8] | 40.3$^{ab}$ | 43.0$^a$ | 33.2$^{ef}$ | 43.3$^a$ | 38.5$^{bc}$ | 32.0$^{ef}$ | 43.3$^a$ | 35.4$^{cde}$ |

| | Closed[4] (1 atm) | | | | |
|---|---|---|---|---|---|
| | $N_2$ | $CO_2$ | Air | $H_2$ | SE[5] |
| pH | 6.4$^g$ | 7.2$^{abe}$ | 6.5$^{fg}$ | 6.5$^{fg}$ | 0.15 |
| Eh | −230$^{bc}$ | −213$^{abc}$ | −223$^{abc}$ | −216$^{abc}$ | 13.0 |
| Total VFA, μmol | 2080$^{bc}$ | 2575$^{ab}$ | 1386$^{def}$ | 2093$^{bc}$ | 197 |
| Acetate, μmol | 1224$^{bc}$ | 1567$^{ab}$ | 782$^{de}$ | 1257$^{bc}$ | 143 |
| Propionate, μmol | 561$^{ab}$ | 678$^a$ | 393$^{cd}$ | 544$^{abc}$ | 54.9 |
| Butyrate, μmol | 200$^a$ | 218a | 128$^b$ | 197$^a$ | 20.1 |
| Isovalerate, μmol | 16.9$^{cde}$ | 24.1$^a$ | 13.2$^{fg}$ | 17.0$^{cde}$ | 1.08 |
| Valerate, μmol | 65.9$^{bc}$ | 69.6$^{ab}$ | 60.1$^{cde}$ | 65.5$^{bc}$ | 2.19 |
| Isobutyrate, μmol | 11.9$^{cde}$ | 17.4$^{ab}$ | 10.3$^e$ | 12.3$^{cde}$ | 1.00 |
| Total VFA-C, μmol | 5393$^{ab}$ | 6579$^a$ | 3662$^{cd}$ | 5397$^{ab}$ | 486 |
| Acetate:Propion, mole ratio | 2.20$^{ab}$ | 2.37$^{ab}$ | 2.07$^{ab}$ | 2.30$^{ab}$ | 0.30 |
| Acetate:Butyrate, mole ratio | 6.09$^{ab}$ | 7.33$^{ab}$ | 6.46$^{ab}$ | 6.36$^{ab}$ | 1.82 |
| 2Acct + 2Butyr − Propion[6] | 2288$^{bc}$ | 2893$^{ab}$ | 1426$^{de}$ | 2365$^{bc}$ | 285 |
| $H_2$ equiv/$H_2$ w/ VFA[7] | 0.45 | 0.47 | 0.55 | −0.54 | 0.84 |
| NDF remaining (% of DM)[8] | 37.7$^{bcd}$ | 29.9$^f$ | 40.7$^{ab}$ | 34.3$^{de}$ | 1.25 |

$^{abc}$Means (n = 3) with different superscripts differ (Student t test; $P < 0.05$).
*Not included in statistical comparison because gas ($H_2$ or $CO_2$) was added as treatment.
[1]Fermentation under moderate vacuum pressure (0.25 atm) starting with $N_2$ headspace.
[2]Moderate vacuum pressure with intermittent perfusion of gases ($N_2$, $CO_2$, air or $H_2$).
[3]Perfusion of gases without application of moderate vacuum.
[4]Incubation at 1 atm without vacuum or perfusion of gases.
[5]Standard error of the mean, n = 3 per treatment.
[6]Expected $H^2$ equivalent (μmol) based on volatile fatt acid production (2 × acetate + 2 × butyrate − propionate).
[7]$H_2$ equivalent from gases ($H_2$ + 4$CH_4$) divided by expected $H_2$ equivalent from VFA production.
[8]Neutral detergent fiber remaining after 24 h incubation as a percentage of sample dry matter (T = 0 was 60%).

Example 4

Alcohol Production from Different Substrates

An experiment was conducted to test the concept of degrading different substrates with rumen microbes to alcohols, including ethanol. Treatments were arranged in a factorial design with five types of substrate by two initial pH values. Substrates included purified cellulose (0.324 g), corn starch (0.324 g), glucose (0.360 g), arabinose (0.180 g) and xylose (0.180 g), and acetate (4000 tµmol). The quantity of substrate incubated was altered to provide a similar concentration (40 mM or 80 mM for acetate) of carbohydrate substrate. Initial pH was 7.0 or 6.0. Samples were incubated in 125-ml flasks with 40 ml phosphate-buffered media and 10 ml rumen fluid. Low pH was hypothesized to be inhibitory for methanogenesis and propionate synthesis, thereby sparing substrates for ethanol synthesis. All flasks were perfused with $H_2$ gas before incubating them to provide additional $H_2$ to make ethanol accumulation thermodynamically favorable. There were 3 flasks for each pH treatment and substrate. Flasks were sampled after incubation for 0, 24, 48, or 120 h. After the sampling, flasks were re-perfused with $H_2$ gas and returned to the water bath. Because the variance across substrates was not uniform, results were analyzed for each substrate separately for pH effect nested within the random effect of flask, and for effect of time.

The results in Table 7 demonstrate the concept of using gut microbes to produce ethanol from a variety of different substrates including cellulose and five-carbon sugars (arabinose and xylose), which make up hemicellulose. Starch and glucose also gave rise to ethanol. There was also a small amount of 1-propanol produced (Table 0.8). Whereas so many different substrates can be converted to ethanol, and simultaneously converted to fuel gases, the potential exists to use a microbial culture system that can be adapted to multiple types of substrate and convert them to different products as the demand for them changes. Current methods to convert grain starch or sugar to ethanol may even be simplified using this type of mixed culture.

TABLE 9

Ethanol production (µmol/flask) for different substrates[1] incubated at 39° C. under $H_2$ with ruminal microbes.

| Substrate | 1 d | 2 d | 5 d | SE[2] | P<[3] |
|---|---|---|---|---|---|
| Glucose | 39 | 44 | 100 | 54.0 | 0.68 |
| Xylose & Arabinose | 24 | 32 | 9.5 | 5.7 | 0.05 |
| Starch | 140 | 138 | 82 | 29.7 | 0.86 |
| Cellulose | 2 | 2.7 | 3.3 | 0.83 | 0.28 |
| Acetate | 5 | 1.7 | 1.0 | 1.0 | 0.004 |

[1]Initial amount of substrate was 2000 µmol except for acetate, which was 4000 µmol, and initial rumen fluid did not have detectable alcohols.
[2]Standard error of the mean, n = 6.
[3]Effect of time (1, 2 or 5 d but not including T = 0). Whereas variance was not homogenous across substrates, each substrate was analyzed separately.

TABLE 10

1-Propanol production (µmol/flask) for different substrates[1] incubated at 39° C. under $H_2$ with ruminal microbes.

| Substrate | 1 d | 2 d | 5 d | SE[2] | P<[3] |
|---|---|---|---|---|---|
| Glucose | 2.4 | 1.9 | 1.8 | 1.83 | 0.84 |
| Xylose & Arabinose | 3.8 | 3.5 | 1.0 | 0.68 | 0.02 |
| Starch | 4.8 | 7.1 | 7.0 | 1.68 | 0.56 |
| Cellulose | 0.3 | 0.8 | 1.0 | 0.34 | 0.32 |
| Acetate | 0.15 | 0.0 | 0.0 | 0.052 | 0.11 |

[1]Initial amount of substrate was 2000 µmol except for acetate, which was 4000 µmol, and initial rumen fluid did not have detectable alcohols.
[2]Standard error of the mean, n = 6.
[3]Effect of time (1, 2 or 5 d but not including T = 0). Whereas variance was not homogenous across substrates, each substrate was analyzed separately.

Acetate was also included as a substrate but little ethanol was produced. In hindsight, including acetate by itself would have not provided the conditions to shift equilibrium toward ethanol. Being that other volatile fatty acids were lacking, the favored pathways would be for production of other fatty acids. The previous experiment already established the concept of producing ethanol from volatile fatty acids. There was no effect of pH on the production of ethanol.

Example 5

Conditions for Alcohol Production

Another experiment on alcohol accumulation was conducted to test the effects of including mixed volatile fatty acids, methane inhibitors, or ethanol in the fermentation. The hypothesis was that initially providing volatile fatty acids would shift the equilibrium against additional synthesis of volatile fatty acids, and methane inhibitors would inhibit methanogenesis. Closing these pathways would leave carbon and hydrogen available for ethanol production. In order to test whether ethanol could be degraded, an initial concentration of ethanol was included in a set of samples representing each treatment and substrate. Treatments were arranged in a 2×4×2 factorial design with repeated measures. Factors were substrate (0.34 g glucose or 0.5 g timothy hay), additions (control, 36 mM initial concentration of volatile fatty acids (VFA; 20 mM acetate, 10 mM propionate, 6 mM butyrate), VFA+ Bromoethanesulfonic acid (BES; 50 uM), VFA+Ethyl-2-butynoate (E2B; 8 mM), and ethanol addition (100 mM). Repeated measures were taken after incubation for 24 or 48 h. All samples were incubated at 39° C. in 125-ml flasks containing 40 ml phosphate buffered media and 10 ml rumen fluid after perfusing with $H_2$. Initial pH was 6.0 to inhibit propionate and methane synthesis. Samples were perfused with $H_2$ again after the 24 h sampling. Alcohols were analyzed by gas chromatography. Each treatment was replicated three times in one run. Because many interactions with ethanol inclusion were significant, the results were analyzed separately for samples with or without ethanol. The mixed model was: Y=mean+substrate+additions+substrate×additions+ flask (substrate, additions) random+time+interactions with time. Non-significant interactions were removed stepwise.

Results are shown Table 11 for the samples in which ethanol was not initially added. Ethanol was produced in higher concentrations than for the previous experiment probably because the conditions of high $H_2$, high volatile fatty acid concentrations and methane inhibitors would favor ethanol thermodynamics. Greater ethanol production was observed when glucose was the substrate compared to timothy hay, and when volatile fatty acids or methane inhibitors were included. The presence of volatile fatty acids at the start of the fermentation increased the ethanol accumulation. This treatment would have shifted the equilibrium away from volatile fatty acid production leaving ethanol as a feasible end product.

TABLE 11

Effect of volatile fatty acids (VFA), methane inhibitors (BES and E2B), substrate type (glucose or grass hay) and duration of incubation (24 or 48 h) on ethanol accumulation (μmol/flask) when incubating without an initial concentration of ethanol[1]

|  | Glucose | | Timothy | |
|---|---|---|---|---|
| Additive | 24 h | 48 h | 24 h | 48 h |
| Control | 55 | 125 | 0 | 0 |
| VFA | 70 | 160 | 20 | 10 |
| VFA + BES | 110 | 110 | 55 | 50 |
| VFA + E2B | 5 | 35 | 45 | 25 |
| SEM[2] | 25 | 25 | 5.5 | 5.5 |

[1]Initial concentration of ethanol from rumen fluid was not detectable and initial amount of substrate was 2000 μmol.
[2]Standard error of the mean. Each treatment replicated 3 times. Significant effects: substrate ($P < 0.0002$), additive ($P < 0.02$), time ($P < 0.08$), substrate × time ($P < 0.01$) and substrate × additive ($P < 0.02$). Three way interaction was not significant. Substrate and additive were nested within flask, which was a random effect.

For glucose, more ethanol was observed at 48 h than after 24 h of fermentation. Because glucose is very rapidly fermented, increases in ethanol that occur between 1 to 2 days must result from further metabolism of products of the initial degradation. This finding suggests we can provide conditions for optimal feed degradation to produce volatile fatty acids, and then those conditions can be changed to convert acids to ethanol or other alcohols over time.

The pH was lower ($P<0.01$) with the glucose substrate (5.2) than for the timothy hay (5.9). For the glucose substrate, pH decreased from 5.4 at 24 hours to 4.9 at 48 h. The pH did not change from 24 to 48 hours for timothy hay. The lower pH for glucose could have resulted from greater production of lactic acid, which has a lower pKa than other volatile acids. The lower pH may have inhibited methanogens and propionate producers, thus favoring ethanol.

Commercial production of ethanol with a mixed culture of microorganisms would require that ethanol be removed before it is further metabolized, or else the metabolism of ethanol be prevented. In the other half of the experiment, ethanol (100 mM) was added to the flasks before inoculation with rumen bacteria. Otherwise the treatments were the same as in the previous table. Surprisingly, substantially more ethanol was found in the control treatment as shown in Table 12. The presence of ethanol may inhibit competitors of the fermentation. Rumen microorganisms are capable of producing ethanol, but normally it is converted to volatile fatty acids. Only when the conditions of the fermentation are changed as described herein does ethanol accumulate.

TABLE 12

Effect of volatile fatty acids (VFA), methane inhibitors (BES and E2B), substrate type (glucose or grass hay) and duration of incubation (24 or 48 h) on ethanol accumulation (μmol) when incubating with an initial concentration of ethanol[1]

|  | Glucose | | Timothy | |
|---|---|---|---|---|
| Additive | 24 h | 48 h | 24 h | 48 h |
| Control | 6200 | 6350 | 6250 | 6450 |
| VFA | 4950 | 5900 | 5450 | 5250 |
| VFA + BES | 5300 | 5100 | 5300 | 5400 |
| VFA + E2B | 5100 | 5500 | 5600 | 6150 |
| SEM[2] | 375 | 375 | 375 | 375 |

[1]Initial concentration of added ethanol was 100 mM (5000 μmol/flask) and initial amount of substrate was 2000 μmol/flask. Alcohols were not detectable in the original rumen inocula.
[2]Standard error of the mean. Each treatment replicated 3 times. Significant effects: additive ($P < 0.03$), other effects and interactions were not significant.

When ethanol was added, there were no effects of substrate or time, but the control was higher in ethanol than when volatile fatty acids were added, with or without methane inhibitors. The added ethanol did not appear to be degraded for any treatments, and appeared to have increased the production of ethanol. Perhaps, ethanol is toxic to competing organisms, thus driving the fermentation toward greater ethanol. The pH followed similar trends for samples with ethanol compared to samples without ethanol, except 24-h pH was higher for glucose with ethanol (6.0) than without it (5.4).

In addition to ethanol, fermentations also produced 1-propanol and 1-butanol according to similar trends as for ethanol (Tables 13 to 16). Isopropanol was detected in some samples but could not be quantified accurately.

TABLE 13

Effect of volatile fatty acids (VFA), methane inhibitors (BES and E2B), substrate type (glucose or grass hay) and duration of incubation (24 or 48 h) on 1-propanol accumulation (μmol/flask) when incubating without an initial concentration of ethanol[1]

|  | Glucose | | Timothy | |
|---|---|---|---|---|
| Additive | 24 h | 48 h | 24 h | 48 h |
| Control | 3.5 | 4 | 1.5 | 0.5 |
| VFA | 7 | 7.5 | 8 | 8 |
| VFA + BES | 7.5 | 7.5 | 15 | 13 |
| VFA + E2B | 5 | 8 | 9 | 5 |
| SEM[2] | 1.1 | 1.1 | 1.1 | 1.1 |

[1]Initial concentration of alcohols from rumen fluid were not detectable and initial amount of substrate was 2000 μmol/flask.
[2]Standard error of the mean. Each treatment replicated 3 times. Significant effects: substrate ($P < 0.0001$), additive ($P < 0.01$), substrate × additive ($P < 0.001$); no effect of interactions or time.

TABLE 14

Effect of volatile fatty acids (VFA), methane inhibitors (BES and E2B), substrate type (glucose or grass hay) and duration of incubation (24 or 48 h) on 1-propanol accumulation (μmol/flask) when incubating with an initial concentration of ethanol[1]

|  | Glucose | | Timothy | |
|---|---|---|---|---|
| Additive | 24 h | 48 h | 24 h | 48 h |
| Control | 3.5 | 5.5 | 36.5 | 40 |
| VFA | 8.5 | 14 | 36.5 | 27.5 |
| VFA + BES | 13 | 12 | 22.5 | 28.5 |
| VFA + E2B | 13.5 | 7.5 | 14.5 | 12 |
| SEM[2] | 3.35 | 3.35 | 3.35 | 3.35 |

[1]Initial concentration of added ethanol was 100 mM (5000 μmol/flask) and initial amount of substrate was 2000 μmol/flask. Alcohols were not detectable in the original rumen inocula.
[2]Standard error of the mean. Each treatment replicated 3 times. Significant effects: substrate ($P < 0.05$), additive ($P < 0.0001$), substrate × additive ($P < 0.005$); no effect of interactions or time.

TABLE 15

Effect of volatile fatty acids (VFA), methane inhibitors (BES and E2B), substrate type (glucose or grass hay) and duration of incubation (24 or 48 h) on 1-butanol accumulation (μmol/flask) when incubating without an initial concentration of ethanol[1]

|  | Glucose | | Timothy | |
|---|---|---|---|---|
| Additive | 24 h | 48 h | 24 h | 48 h |
| Control | 0.5 | 0.5 | 0 | 0 |
| VFA | 0 | 1 | 1 | 0 |
| VFA + BES | 0 | 6.5 | 18 | 0.5 |

TABLE 15-continued

Effect of volatile fatty acids (VFA), methane inhibitors (BES and E2B), substrate type (glucose or grass hay) and duration of incubation (24 or 48 h) on 1-butanol accumulation (μmol/flask) when incubating without an initial concentration of ethanol[1]

|          | Glucose |      | Timothy |      |
|----------|---------|------|---------|------|
| Additive | 24 h    | 48 h | 24 h    | 48 h |
| VFA + E2B | 0      | 1.5  | 0.5     | 0    |
| SEM[2]   | 0.55    | 0.55 | 0.55    | 0.55 |

[1]Initial concentration of ethanol from rumen fluid not detectable and initial concentration of substrate was 2000 μmol. Alcohols were not detectable in the original rumen inocula.
[2]Standard error of the mean. Each treatment replicated 3 times. Significant effects: substrate × time (P < 0.02).

TABLE 16

Effect of volatile fatty acids (VFA), methane inhibitors (BES and E2B), substrate type (glucose or grass hay) and duration of incubation (24 or 48 h) on 1-butanol accumulation (μmol/flask) when incubating with an initial concentration of ethanol[1]

|           | Glucose |      | Timothy |      |
|-----------|---------|------|---------|------|
| Additive  | 24 h    | 48 h | 24 h    | 48 h |
| Control   | 0.5     | 2    | 5       | 7.5  |
| VFA       | 0       | 2.5  | 10      | 2    |
| VFA + BES | 0       | 0    | 3.5     | 2.5  |
| VFA + E2B | 3.5     | 0    | 20      | 0    |
| SEM[2]    | 1.5     | 1.5  | 1.5     | 1.5  |

[1]Initial concentration of added ethanol was 100 mM (5000 μmol/flask) and initial amount of substrate was 2000 μmol/flask. Alcohols were not detectable in the original rumen inocula.
[2]Standard error of the mean. Each treatment replicated 3 times. Significant effects: substrate (P < 0.005), substrate × additive × time (P < 0.05).

These results demonstrate that a mixed culture of rumen microorganisms may be used to produce ethanol as well as fuel gases. Such a mixed culture can be manipulated, as described herein, to change the form of products produced according to market demand. In addition, the feedstock can be altered in accordance with what is available.

Example 6

Electricity Generation in Microbial Fuel Cells

Four microbial fuel cells were constructed in which the fermentation proceeded in a 125-ml glass bottle acting as an anode (source of electrons) connected by a glass bridge to a 125-ml glass bottle acting as an cathode. Eight glass bottles were adapted by fusing a glass fitting in the side of each bottle so that they could be connected to each other in groups of two (anode and cathode). The bottles were clamped together at this fitting with a Ultrex proton-exchange membrane (CMI-7000, Membrane International, Glen Rock, N.J.) and a rubber gasket between them. Graphite plates (6 cm×2 cm×0.6 cm) were used as electrodes in each chamber. Holes were drilled in the top edge of each plate so that a solid insulated copper wire (14 G) could be inserted and affixed with silver epoxy, and covered with non-conductive epoxy.

The fermentation (anode) bottle was fitted with a rubber stopper and glass tubing to enable collection of gases in mylar balloons and with the wire from the electrode protruding through the stopper to enable transfer of electricity. The cathode chamber was uncovered. The cathode compartment contained 50 mM $K_3Fe(CN)_6$ to enhance oxygen reduction in 100 mM phosphate buffer (pH 7). The buffers and inocula in the anode chamber were similar to those described for fermentation experiments. The electrodes were connected across a-180 Ohm resister. Electrical output was determined by measuring voltage at selected time points and calculating amperage as voltage divided by resistance.

An experiment was conducted to demonstrate the effect of different perfusion gases ($N_2$ or $CO_2$) on electricity generation, and effect of electricity generation on digestion and fermentation. In the anode chamber, 1 g of timothy hay was digested in 80 ml phosphate-buffered media with $N_2$ gas or carbonate-buffered media with $CO_2$ and 20 ml of rumen fluid. Four 125-ml flasks were also incubated under identical conditions. Treatments were arranged in a 2×2 factorial design with 2 replicates of each treatment. The factors were perfusion gas ($N_2$ or $CO_2$) and generation of electricity or not. Initial electric current was determined after incubation for 10 minutes. Samples were temporarily removed from the bath after incubation for 0.17, 2, 6, 12, 24, 48, and 120 h. At each time point current was determined by measuring voltage across each cell. Accumulated gas was removed from the balloons, measured in volume, and sampled. The pH and Eh were determined, and samples were sampled (1 ml) for volatile fatty acids and alcohols. Flasks were perfused again with the corresponding gas before returning them to the bath. The equilibrium $H_2$ was calculated using the Nerst equation (Segel, 1976): $E_h$ (volts)=$E_0$+0.059×Log($[H^+]/[H_2]$). The statistical software could not solve the mixed model due to convergence errors so results were analyzed by time point for effects of perfusion gas type and whether or not electricity was generated.

Results

Electricity can also be produced from a mixed culture of gut microorganisms. A microbial fuel cell was constructed and tested in the following experiment and the fermentation compared to the same incubations without capturing electricity. Microbial fuel cells generate electricity by allowing electrons to flow through a conductor while protons flow through a proton permeable membrane. The energy generation is driven by a high concentration of $H_2$ on one side, with the availability of an oxidizing agent like oxygen (air) on the other to remove the $H_2$ by forming water. As has been shown, the removal of $H_2$ from ruminal incubations has important consequences to other energy products, it was decided to evaluate how harvesting electricity in a fuel cell affects fermentation, and how gas composition affects the fuel cell. In this experiment, the gas phase above the fuel cell was either $CO_2$ or $N_2$, and the fuel cells were compared to similar fermentations without generation of electricity.

Figure 16:
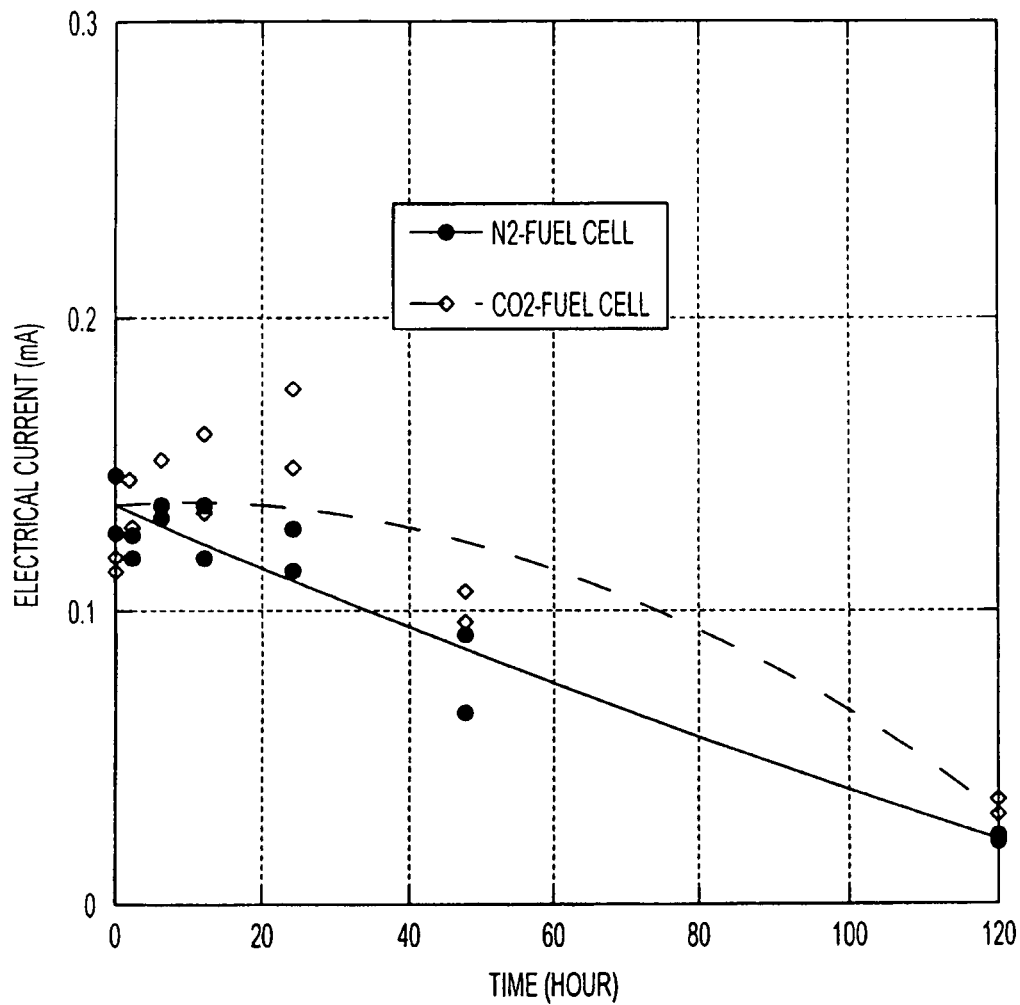
FIG. 16 illustrates electrical current generated from microbial fuel cells or flasks incubated with timothy hay under $N_2$ or under $CO_2$ perfusion. An effect of time is noted ($P<0.001$), but no effect of perfusion gas.
Figure 17:
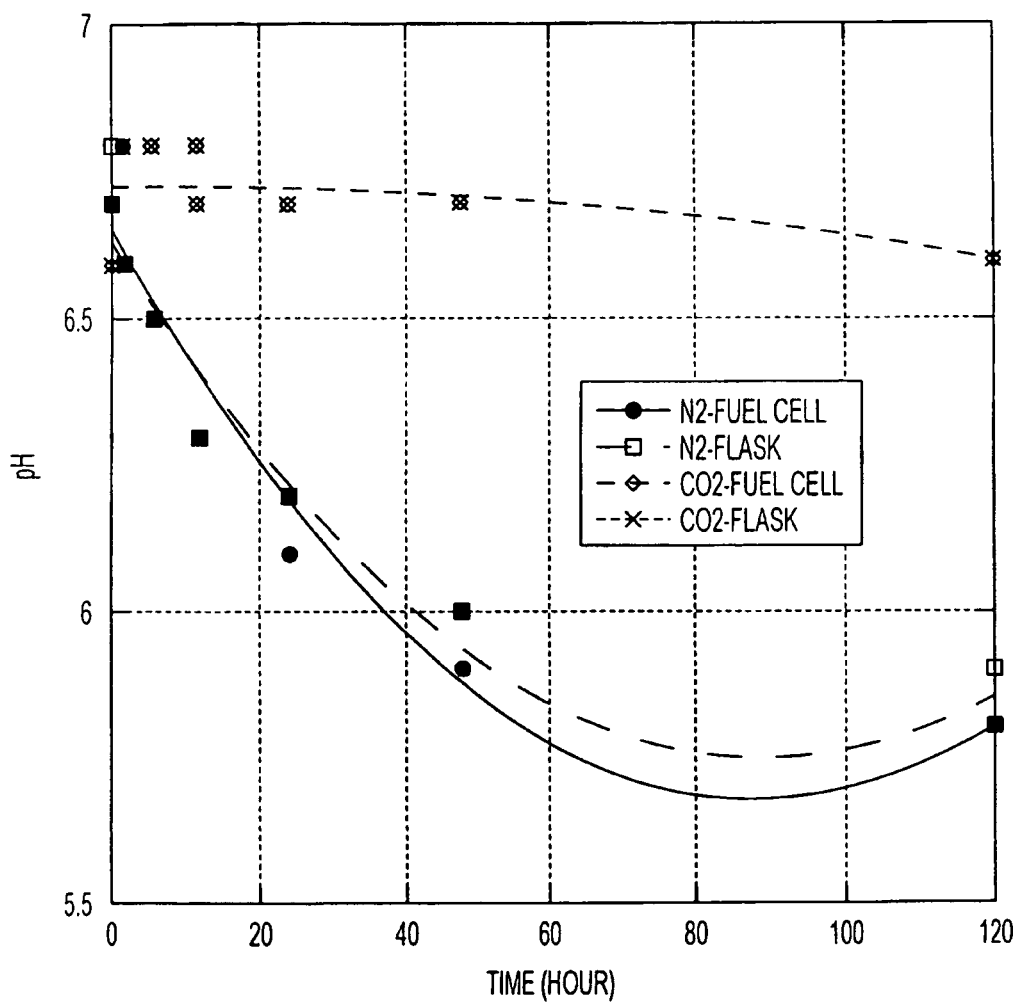
FIG. 17 illustrates the effect of changing pH for microbial fuel cells or flasks incubated with timothy hay under $N_2$ or $CO_2$ perfusion. Perfusion gas affected pH ($P<0.0001$) for every time point under 6 hours. No effect of flask versus fuel cell was noted.

FIG. 16 shows the current generated by the microbial fuel cells over the course of five days. There was a decrease in electrical current over time, but no effect of which perfusion gas ($CO_2$, or $N_2$) was used. The pH of the fuel cells and analogous flasks is shown in FIG. 17. Because the phosphate buffer is not as effective as carbonate buffer (which would supply $CO_2$), the $N_2$, perfusion resulted in more rapid decline in pH to about 5.7. There was no effect of the fuel cells compared to the flasks without electricity generation.

Figure 18:
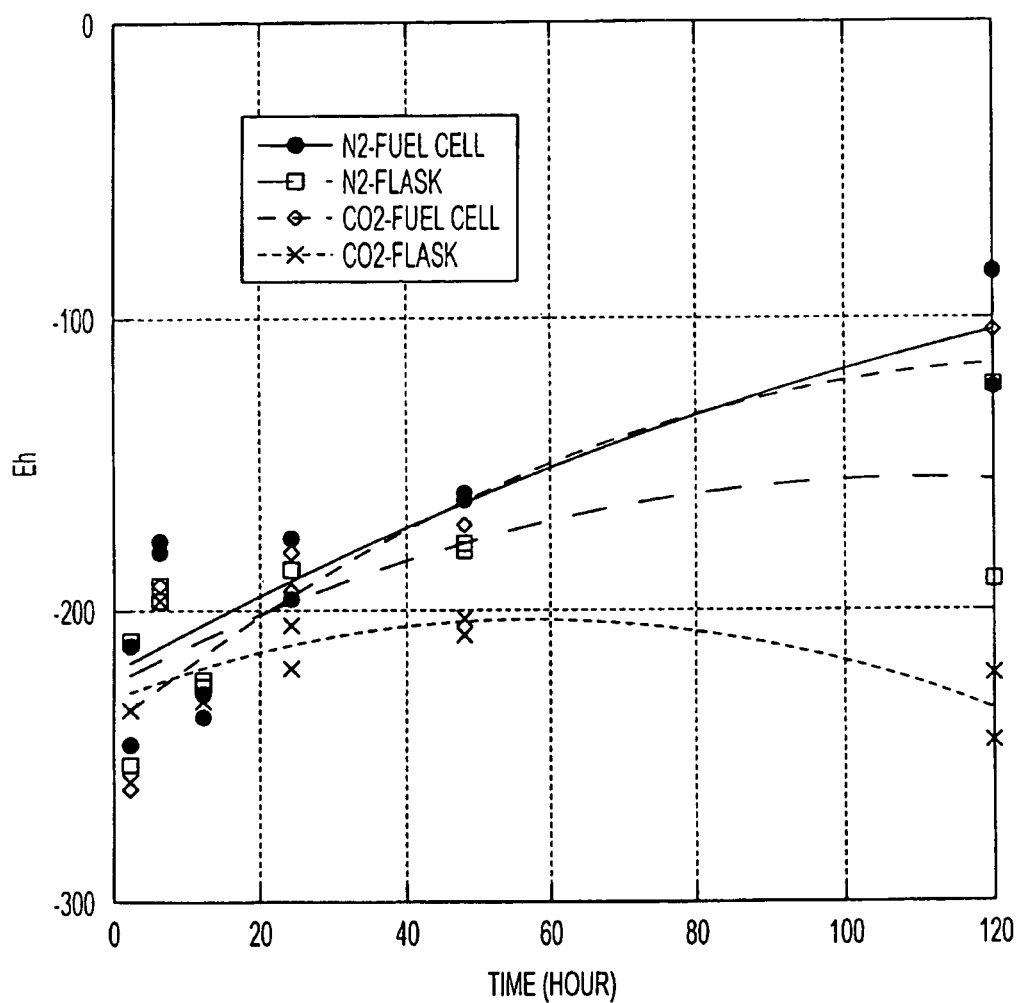
FIG. 18 illustrates changes in redox potential (Eh) for microbial fuel cells or flasks incubated with timothy hay under $N_2$ or $CO_2$ perfusion fuel cells exhibited less negative $E_h$ (P<0.05) for every time point under 6 hrs. No effect of perfusion was noted.

The effect of redox potential is shown in FIG. 18. The fuel cells had less negative $E_h$ (a lower propensity to contribute electrons) than the flasks where no electricity was harvested whether perfused with $CO_2$ or $N_2$. Concentration of hydrogen in collected gas was the same for corresponding fuel cells and flasks. After 6 hours of incubation, concentration of hydrogen was higher for carbon dioxide perfused samples than nitrogen perfused samples, but there was a tendency for the opposite at 24 hours. Otherwise there was no effect of either perfusion gas or whether fuel cell or flask on hydrogen concentration of collected gas, further demonstrating that hydrogen quickly comes into equilibrium.

Figure 19:
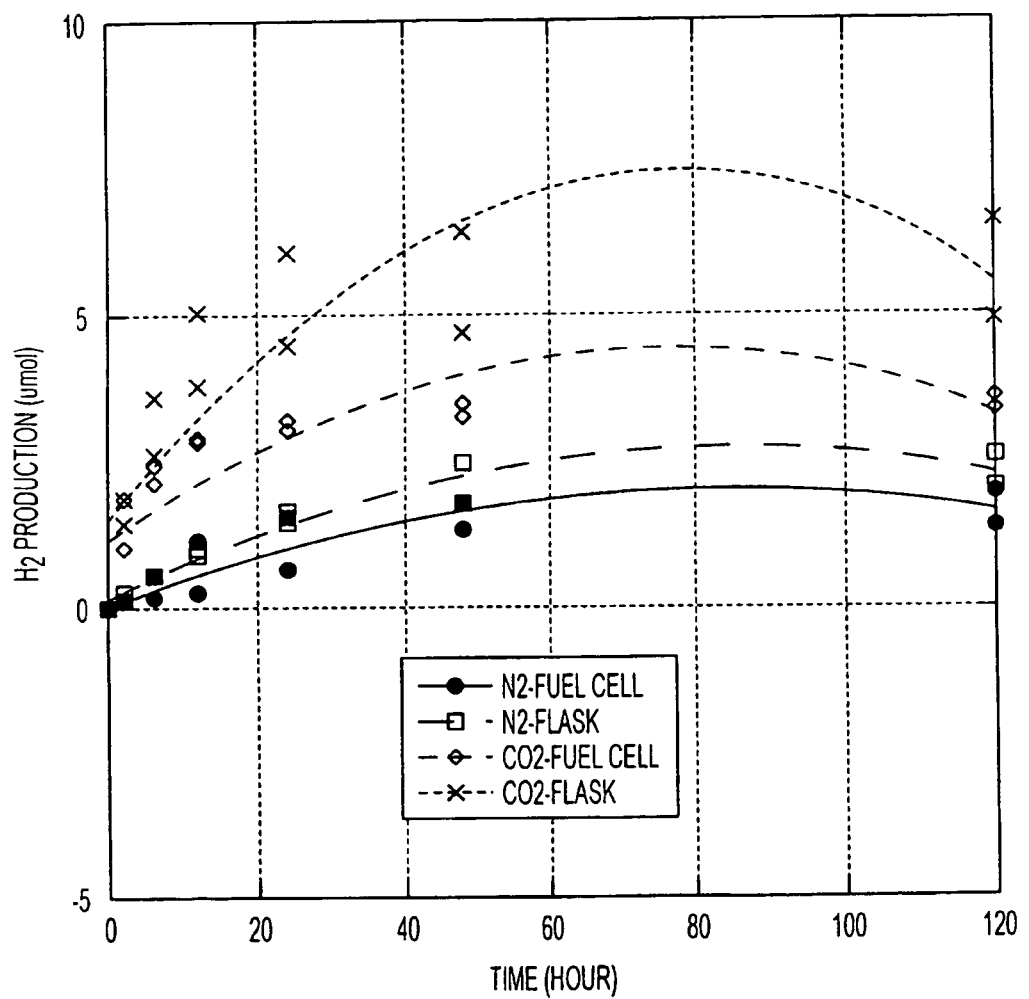
FIG. 19 illustrates change in hydrogen production for microbial fuel cells or flasks incubated with timothy hay under $N_2$ or $CO_2$ perfusion. $CO_2$ perfusion resulted in greater hydrogen production than $N_2$ perfusion and hydrogen in flasks was greater than in fuel cells at time≥6 h (P<0.05).
Figure 20:
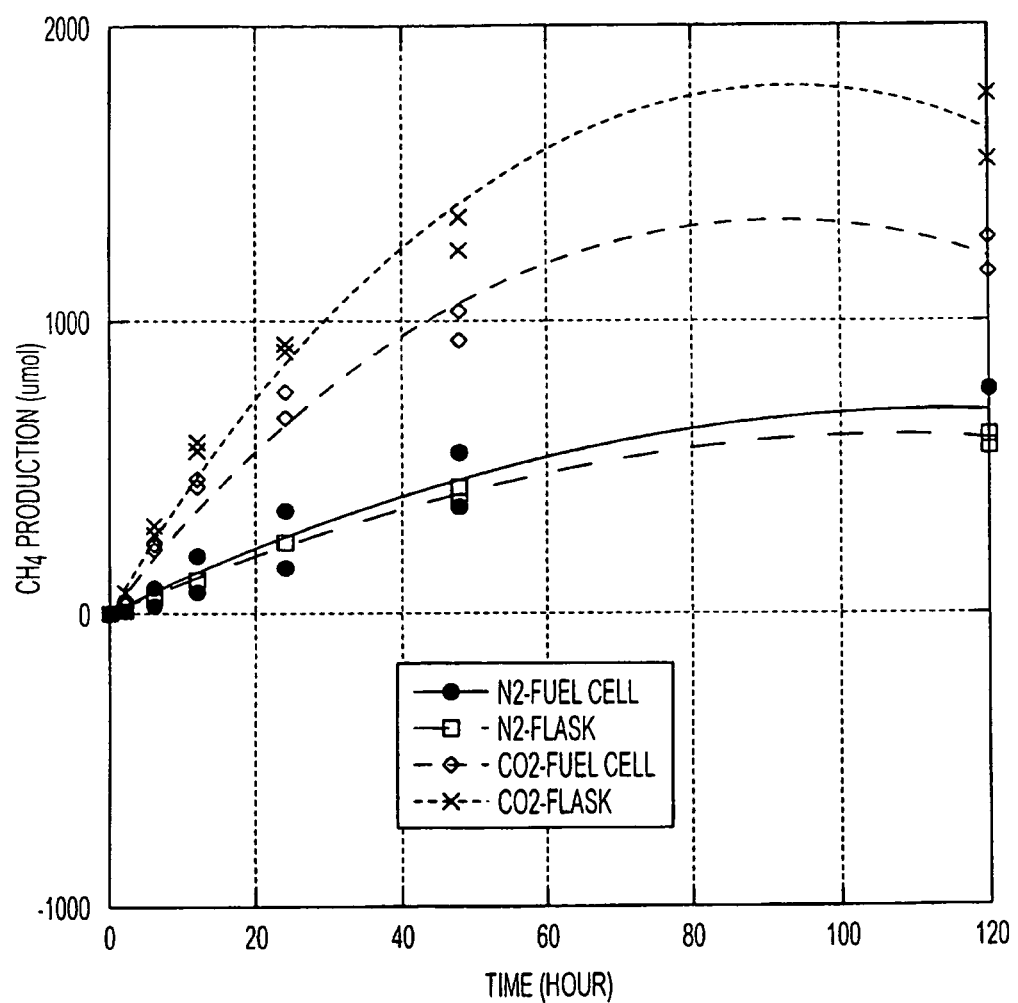
FIG. 20 illustrates change in methane production for microbial fuel cells or flasks incubated with timothy hay under nitrogen $N_2$ or $CO_2$ perfusion. $N_2$ perfusion resulted in lower (P<0.05) methane production than $CO_2$ perfusion at all time points equal to or greater than 2 h. With $CO_2$ perfusion, fuel cells had lower (P<0.05) methane than flasks equal to or greater than 12 or more hours.

There was greater hydrogen production with carbon dioxide than for nitrogen perfusion (FIG. 19). This effect would have resulted from greater gas production (carbon dioxide and methane) with similar concentrations of hydrogen. Fuel cells produced less hydrogen than flasks (FIG. 19) demonstrating the effect of diverting hydrogen to electricity production.

There was greater methane production with carbon dioxide perfusion than with nitrogen perfusion for both fuel cells and flasks. Carbon dioxide can be a substrate for methanogenesis so this result is expected. There was less methane produced with fuel cells than with flasks indicating that hydrogen was diverted from methanogenesis to electricity.

There was greater carbon dioxide produced for the treatments perfused with carbon dioxide. We did not subtract the carbon dioxide that would have been released from bicarbonate. There was no difference in carbon dioxide from fuel cells compared to flasks. There was also no significant difference between fuel cells and flasks in the sum of carbon dioxide and methane produced (representing degradation).

TABLE 17

Effect of perfusion gas ($CO_2$ or $N_2$) and whether or not electricity was generated in a fuel cell on neutral detergent fiber (NDF) remaining (% of initial dry matter) after 120 h incubation of timothy hay with ruminal microbes.

| $CO_2$ perfusion | | $N_2$ perfusion | | | Effects, P<[2] | |
|---|---|---|---|---|---|---|
| Flask | Fuel cell | Flask | Fuel cell | SE[1] | Perfusion | Fuel cell |
| 15.3 | 15.9 | 20.4 | 22.5 | 0.38 | 0.0001 | 0.03 |

[1]Standard error of the mean, n = 2 fuel cells or flasks for each perfusion gas.
[2]Main effect of perfusion gas or fuel cell. There was no interaction (P > 0.1).

The NDF digestion from fuel cells and analogous flasks are shown in Table 17. Most plant fiber was digested by the end of the 5 day (120 hrs) fermentation. Flasks and fuel cells perfused with $CO_2$ showed greater NDF digestion than those perfused with $N_2$. Fuel cells demonstrated slightly less NDF digestion than the analogous flasks.

These results demonstrate the production of electricity from fuel cells using rumen microorganisms, the effect of the different gas pressures on fuel cell function, and the effect of the fuel cells on the fermentation.

Example 7

Effect of Sulfur Reducing Agents on Alcohol and Gas Production

An experiment was conducted to determine the effect of adding sulfur reducing agents on production of gases, volatile fatty acids, and alcohols. Twenty treatments were arranged in a 2×2×5 factorial design with factors of initial headspace gas ($CO_2$ or $N_2$), addition of 25 ml $H_2$ gas to the initial headspace (+$H_2$, —$H_2$), or one of five sources of sulfur redox agents (0.32 mmol/flask): $Na_2SO_4$, $Na_2SO_3$, $S^0$, $Na_2S$, or none. Samples (0.5 g timothy hay) were incubated for 24 hours and products measured as previously. At the start of the incubation, each 125-ml flask was perfused with respective gas. For treatments receiving added $H_2$, 25 ml of perfused gas (at 1 atm pressure) was removed from the flask headspace and forced into the collection balloon. This removed gas was replaced with $H_2$.

As expected based on previous results, methane production was greater for samples starting with $CO_2$ compared to those starting with $N_2$, and for samples with added $H_2$ (Table 18). The combination of both $CO_2$ and $H_2$ resulted in the greatest methane production. Hydrogen was readily consumed in the flasks in which $H_2$ was initially added. This $H_2$ could be accounted for in the increase in $CH_4$, and increase in acetate to propionate ratio, although actual acetate and propionate production decreased with added $H_2$ (Table 19). Addition of $H_2$ decreased fiber degradation (Table 19), which demonstrates as a negative treatment the effect of $H_2$ on degradation of feed.

Treatments containing ($Na_2SO_3$) differed from all other agents for each gas composition (Table 20). Sulfite strongly inhibited methane production (Table 20) and valerate formation (Table 21), sparing $H_2$ to be released directly (Table 20). This treatment also resulted in ethanol and 1-propanol production (Table 21). There was greater alcohol production in sulfite treatments initially perfused with $N_2$ than those perfused with $CO_2$. Sulfite decreased neutral detergent fiber degradation (Table 21). Whereas sulfite appears to close some pathways for $H_2$ utilization, increasing $H_2$ and alcohol production.

Whereas there were several interactions with the sulfite treatment, this treatment was not shown in Tables 18 and 19, but is described here. Valerate production was decreased with sulfite treatment. Treatments that increase $H_2$ concentration often increase valerate as a means to use $H_2$. For the sulfite treatment, valerate decreased in samples starting with $CO_2$ whether $H_2$ was added (2.3 μmol) or not (3.0 μmol); but for samples starting with $N_2$, sulfite did not decrease valerate when $H_2$ was added (8.3 μmol) compared to when it was not (1.7 μmol). Sulfite may be a means to prevent transfer of reducing equivalents to forming valerate.

Although data are not shown, sulfite also decreased the utilization of $H_2$ that was initially introduced in the flasks. The hydrogen production was still negative (−179 μmol) but lower (P<0.0001) for the sulfite treatment compared the other redox agents (Table 1; −698 to −739 μmol) when $H_2$ was added. It appears that sulfite prevented $CH_4$ production even when $H_2$ was added. Methane production was limited to 5 μmol for sulfite treatment with $H_2$ added at the beginning compared with 404 to 505 μmol for treatments without sulfite. Sulfite addition prevented $H_2$ use in several pathways, thereby decreasing digestion but enabling ethanol and 1-propanol production. It is likely to be useful to increasing alkyl alcohol production in future treatments.

TABLE 18

Effect of initial composition of gas headspace ($CO_2$ or $N_2$) with or without initial added $H_2$ on gas production during 24 h incubation of timothy hay with ruminal microorganisms[1].

|  | $CO_2$ | | $N_2$ | | | |
| --- | --- | --- | --- | --- | --- | --- |
|  | $-H_2$ | $+H_2$ | $-H_2$ | $+H_2$ | $SE^2$ | Effects[3] |
| $H_2$ (% of all gases) | $0.06^c$ | $3.31^b$ | $0.09^c$ | $5.21^a$ | 0.333 | GHI |
| $H_2$ (% of fermentation gas)[4] | $0.06^b$ | $3.73^b$ | $0.41^b$ | 21.60a | 1.49 | GHI |
| $CH_4$ (% of all gases) | $4.55^b$ | $7.10^a$ | $5.28^b$ | $7.45^a$ | 0.34 | H |
| $CH_4$ (% of fermentation gas) | $5.08^d$ | $7.68^c$ | $22.93^b$ | $24.79^a$ | 0.39 | GH |
| $CO_2$ (% of all gases) | $85.0^a$ | $81.8^a$ | $17.6^b$ | $17.2^b$ | 2.52 | G |
| $CO_2$ (% of fermentation gas) | $94.9^a$ | $88.7^b$ | $76.7^c$ | $58.0^d$ | 1.03 | GHI |
| $CH_4:H_2$ (molar concentration ratio) | $103^a$ | $2^c$ | $63^b$ | $6^c$ | 8.15 | GHI |
| $CH_4:CO_2$ (molar concentration ratio) | $0.05^d$ | $0.87^c$ | $0.29^b$ | $0.43^a$ | 0.008 | GHI |
| $H_2$ production (μmol) | $5.0^a$ | $-739^b$ | $5.5^a$ | $-698^b$ | 18.9 | H |
| $CH_4$ production (μmol) | $390^b$ | $505^a$ | $313^c$ | $404^b$ | 20.4 | GH |
| $CO_2$ production (μmol) | $3332^a$ | $1778^b$ | $1046^{bc}$ | $937^c$ | 273 | GHI |
| $H_2$ equivalent ($H_2 + 4\ CH_4$) | $1567^a$ | $1282^b$ | $1257^b$ | $917^c$ | 86.6 | GH |

[1] Mean of four treatments excluding sulfite.
[2] Standard error of the mean, n = 12.
[3] Significant (P < 0.05) effects: G (initial gas; $CO_2$ vs. $N_2$), H (with or without added $H_2$), I (interaction of two effects).
[4] Molar percentage among gases, excluding $N_2$
[abc] Means with different superscripts differ (P < 0.05)

TABLE 19

Effect of initial composition of gas headspace ($CO_2$ or $N_2$) with or without initial added $H_2$ on volatile fatty acid and alcohol accumulation during 24 h incubation of timothy hay with ruminal microorganisms[1].

|  | $CO_2$ | | $N_2$ | | | |
| --- | --- | --- | --- | --- | --- | --- |
|  | $-H_2$ | $+H_2$ | $-H_2$ | $+H_2$ | $SE^2$ | Effects[3] |
| pH | $6.71^a$ | $6.70^a$ | $6.18^b$ | $6.19^b$ | 0.01 | GH |
| Eh | $-262^b$ | $-263^b$ | $-235^a$ | $-235^a$ | 6.06 | G |
| Total VFA, μmol | $2372^a$ | $2228^a$ | $2094^b$ | $2066^b$ | 53.0 | G |
| Acetate, μmol | $1552^a$ | $1421^b$ | $1344^b$ | $1318^b$ | 42.9 | GH |
| Propionate, μmol | $583^a$ | $577^a$ | $510^b$ | $528^b$ | 8.50 | G |
| Butyrate, μmol | 198 | 202 | 200 | 199 | 2.17 | — |
| Isovalerate, μmol | $15.5^a$ | $14.8^a$ | $11.4^b$ | $10.8^b$ | 0.53 | G |
| Valerate, μmol | $17.5^a$ | $19.0^a$ | $17.5^a$ | $13.3^b$ | 1.43 | GI |
| Isobutyrate, μmol | $14.2^a$ | $13.3^a$ | $10.8^b$ | $10.4^b$ | 0.44 | G |
| VFA-C, μmol | $5867^a$ | $5606^a$ | $5206^b$ | $5179^b$ | 116 | G |
| Acetate:Propion, mole ratio | $2.65^a$ | $2.46^c$ | $2.63^{ab}$ | $2.50^{bc}$ | 0.51 | H |
| Acetate:Butyrate, mole ratio | $7.8^a$ | $7.0^b$ | $6.72^b$ | $6.61^b$ | 0.18 | GH |
| 2Acet + 2Butyr − Propion[4] | $2917^a$ | $2670^b$ | $2578^b$ | $2506^b$ | 81.6 | GH |
| NDF remaining (% of DM)[5] | $31.5^c$ | $32.9^b$ | $40.4^a$ | $39.8^a$ | 0.36 | GI |

[1] Mean of four treatments excluding sulfite.
[2] Standard error of the mean, n = 12.
[3] Significant (P < 0.05) effects: G (initial gas; $CO_2$ vs. $N_2$), H (with or without added $H_2$), I (interaction of two effects).
[abc] Means with different superscripts differ (P < 0.05).
[4] Estimated production of $H_2$ equivalent from fermentation of sugar to VFA, 2 times acetate and butyrate production in μmol minus propionate production.
[5] Neutral detergent fiber (cellulose, hemicellulose, lignin analyzed as a percentage of initial dry matter.

TABLE 20

Effect of adding sulfur reducing agents on gas production during 24 h incubation of timothy hay with ruminal microorganisms[1].

|  | $SO_4$ | $SO_3$ | $S^0$ | $Na_2S$ | None | $SE^2$ | $P<^3$ |
| --- | --- | --- | --- | --- | --- | --- | --- |
| $H_2$ (% of all gases) | $0.073^b$ | $1.39^a$ | $0.080^b$ | $0.078^b$ | $0.072^b$ | 0.056 | 0.0001 |
| $H_2$ (% of fermentation gas)[4] | $0.24^b$ | $8.18^a$ | $0.22^b$ | $0.24^b$ | $0.24^b$ | 0.188 | 0.0001 |
| $CH_4$ (% of all gases) | $5.02^a$ | $0.12^b$ | $4.61^a$ | $5.04^a$ | $5.00^a$ | 0.433 | 0.0001 |
| $CH_4$ (% of fermentation gas) | $14.4^a$ | $0.82^b$ | $13.8^a$ | $14.3^a$ | $13.6^a$ | 0.502 | 0.0001 |
| $CO_2$ (% of all gases) | $52.1^a$ | $47.9^{ab}$ | $50.5^a$ | $42.9^b$ | $52.5^a$ | 2.07 | 0.05 |
| $CO_2$ (% of fermentation gas) | $85.4^b$ | $92.0^a$ | $86.0^b$ | $85.5^b$ | $86.2^b$ | 0.311 | 0.0001 |

TABLE 20-continued

Effect of adding sulfur reducing agents on gas production during 24 h incubation of timothy hay with ruminal microorganisms[1].

| | $SO_4$ | $SO_3$ | $S^0$ | $Na_2S$ | None | $SE^2$ | $P<^3$ |
|---|---|---|---|---|---|---|---|
| $CH_4:H_2$ (molar conc. ratio) | 85$^a$ | 0.1$^b$ | 79$^a$ | 69$^a$ | 100$^a$ | 15.3 | 0.002 |
| $CH_4:CO_2$ (molar ratio) | 0.182$^a$ | 0.010$^b$ | 0.171$^a$ | 0.183$^a$ | 0.171$^a$ | 0.005 | 0.0001 |
| $H_2$ production (µmol) | 5.0$^b$ | 76.6$^a$ | 5.9$^b$ | 5.2$^b$ | 5.0$^b$ | 3.28 | 0.0001 |
| $CH_4$ production (µmol) | 363$^a$ | 6.6$^b$ | 334$^a$ | 335$^a$ | 375$^a$ | 20.2 | 0.0001 |
| $CO_2$ production (µmol) | 2298$^{ab}$ | 1002$^b$ | 1795$^{ab}$ | 1773$^{ab}$ | 2890$^a$ | 450 | 0.08 |
| $H_2$ equivalent ($H_2$ + 4 $CH_4$) | 1459$^a$ | 103$^b$ | 1340$^a$ | 1344$^a$ | 1505$^a$ | 81.3 | 0.0001 |

$^{ab}$Means with different superscripts differ (P < 0.05).
[1]Mean of two treatments including initial gas of $CO_2$ or $N_2$ without added $H_2$.
[2]Standard error of the mean, n = 6.
[3]Significance of effect of added reducing agent.
[4]Molar percentage among gases, excluding $N_2$.

TABLE 21

Effect of adding sulfur reducing agents on volatile fatty acid and alcohol accumulation during 24 h incubation of timothy hay with ruminal microorganisms[1].

| | $SO_4$ | $SO_3$ | $S^0$ | $Na_2S$ | None | $SE^2$ | $P<^3$ |
|---|---|---|---|---|---|---|---|
| pH | 6.45$^b$ | 6.72$^a$ | 6.43$^b$ | 6.47$^b$ | 6.43$^b$ | 0.015 | 0.0001 |
| Eh | −247$^{ab}$ | −264$^{bc}$ | −249$^{abc}$ | −269$^c$ | −231$^a$ | 7.14 | 0.01 |
| Total VFA, µmol | 2162$^a$ | 1206$^b$ | 2287$^a$ | 2190$^a$ | 2309$^a$ | 66.2 | 0.0001 |
| Acetate, µmol | 538$^a$ | 293$^b$ | 550$^a$ | 541$^a$ | 558$^a$ | 8.63 | 0.0001 |
| Propionate, µmol | 538$^a$ | 293$^b$ | 550$^a$ | 541$^a$ | 558$^a$ | 8.63 | 0.0001 |
| Butyrate, µmol | 198$^a$ | 152$^b$ | 198$^a$ | 202$^a$ | 199$^a$ | 2.58 | 0.0001 |
| Isovalerate, µmol | 13.0$^{ab}$ | 12.3$^b$ | 13.3$^{ab}$ | 14.7$^a$ | 12.8$^b$ | 0.57 | 0.1 |
| Valerate, µmol | 16.7$^b$ | 2.33$^c$ | 17.1$^b$ | 19.5$^a$ | 16.7$^b$ | 0.77 | 0.0001 |
| Isobutyrate, µmol | 12.0$^a$ | 9.8$^b$ | 12.2$^a$ | 13.5$^a$ | 12.3$^a$ | 0.56 | 0.005 |
| VFA-C, µmol | 5370$^a$ | 3071$^b$ | 5634$^a$ | 5455$^a$ | 5687$^a$ | 144 | 0.0001 |
| Acetate:Propion, mole ratio | 2.57 | 2.52 | 2.72 | 2.59 | 2.70 | 0.073 | 0.3 |
| Acetate:Butyrate, mole ratio | 7.00$^a$ | 4.89$^b$ | 7.57$^a$ | 6.91$^a$ | 7.59$^a$ | 0.26 | 0.0001 |
| 2Acet + 2Butyr − Propionate[4] | 2628$^a$ | 1483$^b$ | 2840$^a$ | 2660$^a$ | 2860$^a$ | 108 | 0.0001 |
| Ethanol, µmol | 0 | 25.8$^5$ | 0 | 0 | 0 | 0.298 | 0.0001 |
| 1-propanol, µmol | 0 | 5.4$^6$ | 0 | 0 | 0 | 0.046 | 0.0001 |
| NDF remaining (% of DM)[7] | 36.0$^b$ | 57.2$^a$ | 36.5$^b$ | 35.7$^b$ | 35.7$^b$ | 0.42 | 0.0001 |

$^{ab}$Means with different superscripts differ (P < 0.05).
[1]Mean of two treatments including initial gas of $CO_2$ or $N_2$ without added $H_2$.
[2]Standard error of the mean, n = 6.
[3]Significance of effect of added reducing agent.
[4]Estimated production of $H_2$ equivalent from fermentation of sugar to VFA, 2 times acetate and butyrate production in µmol minus propionate production.
[5]Headspace gas affected (P < 0.001) ethanol production within sulfite treatment ($CO_2$ = 22.4, $N_2$ = 29.3; SE = 0.93, n = 3).
[6]Headspace gas affected (P < 0.02) ethanol production within sulfite treatment ($CO_2$ = 5.06, $N_2$ = 5.68; SE = 0.04, n = 3).

Production of fuels or polymers from biomass requires the degradation of the biomass to utilizable products. The present inventor describes herein that microorganisms may be taken out of the rumen gut for the degradation of biomass, that may subsequently be used to produce biofuels or biopolymers. For example, the digestion of feed by the organisms in the cow's rumen is one of the fastest known microbial degradations of biomass. It results primarily in acetate, a two-carbon acid, which is one of the repeating units of polyvinyl acetate and is similar to the two-carbon alcohol, ethanol.

Gut microorganisms appear to have been overlooked as a means to degrade biomass for fuel production largely because the end products of gut fermentation are short-chain fatty acids rather than glucose, which is currently used for yeast fermentation to ethanol. Rumen microorganisms are known to produce methane, and under certain conditions, small quantities of hydrogen gas or ethanol, but previous researchers have not considered that these organisms could be used to produce large amounts of fuels. Ethanol is known not to accumulate in the rumen and was made only on rare occasions and in low concentrations.

The present inventor believes that he is the first to disclose that methods can be developed using gut microorganisms to produce large quantities of fuels directly from biomass or indirectly via volatile fatty acids produced from biomass. In the examples described in this application, it is demonstrated that microorganisms from the cow's rumen can be used to produce hydrogen, methane, ethanol, propanol, butanol, and electricity, and that substrates for these fuels include: organic acids, glucose, five-carbon sugars (xylose and arabinose), starch, cellulose, or heterogeneous substrate of grass hay. Thus, gut microorganisms have been shown to make several useful biofuels using an assortment of substrates. Furthermore, the methods that were developed using these organisms have resulted in shifts in the fermentation to yield higher concentrations of the desired fuels at faster rates than generally observed for rumen fermentation.

The use of rumen microorganisms, found either in the rumen gut or in the soil, for biomass degradation or biofuel production may be accomplished in many different ways. First, microbial populations from the gut may be enriched to increase the number of certain types of organisms or to change their activities. Second, certain species of organisms may be prospected from the gut, isolated and used in specific cultures for biomass degradation. Third, these isolated species may be genetically engineered to enhance desired activity related to biomass degradation or fuel production, or genes taken from these organisms may be transferred to other microbial species used for biomass degradation or fuel production. Ultimately, the desired enzymes from these microorganisms may be harvested from organisms prospected from the gut.

Methane was thought to be produced only from carbon dioxide and hydrogen in the rumen, not from degradation of organic acids. The present invention now provides, indeed, that when treated according to our procedures, much of the digested biomass can be converted to methane using gut microorganisms. Incubation of feedstock with rumen microorganisms and low concentrations of methane and carbon dioxide using vacuum or perfusion of inert gas results in degradation of volatile fatty acids to methane. The procedures described herein could also be applied to methane digesters to accelerate methane production.

The present inventor's discoveries could also be used and applied in reverse to inhibit methane digestion where it is not wanted. Low carbon dioxide pressures, low hydrogen pressures or high methane concentrations can be used to inhibit methane synthesis from carbon dioxide and hydrogen. High carbon dioxide and methane pressures can inhibit methane production from degradation of fatty acids or other biomass.

Hydrogen was known to be produced by rumen microbes, but hydrogen gas does not accumulate in the rumen as it is readily used to produce other end products. The research disclosed herein has demonstrated the means to increase hydrogen production through use of vacuum, perfusion gases, sulfite, or electricity production in a microbial fuel cell. This hydrogen can be used directly as fuel or used to produce other fuels like ethanol or electricity.

Further, the procedures disclosed herein with rumen microorganisms have produced far greater accumulation of ethanol than observed in a normally functioning rumen. Maintaining low concentrations of carbon dioxide, high concentrations of hydrogen or reducing equivalents, sulfite, and high concentrations of volatile fatty acids or ethanol all were shown herein to increase ethanol accumulation. Removing carbon dioxide from fermentation gas also increases ethanol production rates and concentrations. Ethanol concentration could be further increased by vacuum distillation during the digestion process. These gut microorganisms could be isolated or enriched to produce alcohol for beverages, fuels, medicine, or other purposes.

Currently, yeast is used to convert glucose to ethanol, and methods are being developed to convert glucose from cellulose to ethanol by first degrading the cellulose to glucose. The present invention provides an advantageous alternative. Notably, the conversion of cellulose directly to ethanol using microorganisms is demonstrated herein the present inventor has demonstrated the use of rumen microorganisms to produce ethanol from five-carbon sugars, like xylose and arabinose, which comprise a major part of plant material. Use of five-carbon sugars is a major bottleneck for use of biomass for ethanol production, although a bacterium has been engineered to use the sugars but not the substrates (e.g. hemicellulose) that give rise to them. Rumen spirochetes have been shown to convert five—carbon sugars to ethanol, and a rumen fungus resembling Neocallimastix produced ethanol in pure culture with xylose. The present inventor has also demonstrated the use of microorganisms to readily interconvert volatile fatty acids to each other and to convert them to ethanol. Thus, our system is advantageous because of the heterogeneous substrates it can use and the few steps that are needed to both degrade and convert biomass to ethanol.

In addition to producing ethanol using rumen microbes, the methods disclosed herein may also be used to enrich for organisms to produce ethanol. Normally, enrichment for organisms that degrade a certain substrate can be achieved by growing the community over many generations in the presence of that substrate. Enrichment for production of ethanol would normally not be possible in this way because many different products can be produced from the substrates of interest. However, our studies showed ethanol does not degrade in the presence of rumen microbes under certain conditions because ethanol becomes thermodynamically stable. Production of other end products like organic acids or methane would not be as thermodynamically feasible under these conditions, so their production would not yield as much free energy. Thus, the methodologies described herein provide advantage to ethanol producers, which favors their enrichment.

Other end products of gut fermentation can be manipulated using methods described herein. Low carbon dioxide concentration increases acetate and butyrate and decreases propionate. The lower alkyl alcohols, such as butanol and propanol, are similarly affected.

Thus, the present invention entails numerous aspects, including, but not limited to:

A. A process for effecting anaerobic digestion of biomass, which entails the step of anaerobically digesting the biomass with at least one species of a rumen microorganism.

Preferably, this process is conducted under a partial vacuum of less than 1.0 atm, and move preferably under a partial vacuum of less than 0.5 atm, and even more preferably under a partial vacuum of from about 0.2 to 0.4 atm.

Further, this process further entails the step of removing hydrogen formed from the anaerobic digesting.

Preferably, the anaerobic digesting is conducted at a temperature of about 50° C. or less, and more preferably at a temperature of about 45° C. It is even more preferred if the anaerobic digesting is conducted at a temperature of from about 20 to 40° C.

In this process, the biomass may be whole plant material, woods, leaves, grain, residential plant waste. Preferably, the digesting biomass is diluted with inert gas. The inert gas may be any inert gas such as nitrogen or argon, for example. Moreover, the rumen microorganisms may be rumen archea, bacteria, protozoa or fungi or any combination thereof.

Additionally, this process may also entail maintaining carbon dioxide and hydrogen concentrations to prevent degradation of short-chain fatty acids, or removing carbon dioxide and hydrogen to accelerate degradation of short-chain fatty acids, if desired.

B. A process for producing lower alkyl alcohols, which entails the step of:

a) anaerobically degrading biomass with at least one species of rumen microorganisms.

Preferably, this process further entails the step of adding hydrogen gas during said anaerobic degrading.

Additionally, in this process, fermentation gas is preferably removed by vacuum.

In this process, the produced lower alkyl alcohols are isolated by distillation.

The lower alkyl alcohols may be any or all of ethanol, n-propanol, isopropanol, n-butyl, sec-butyl alcohol and/or tert-butyl alcohol.

Preferably, the lower alkyl alcohol is ethanol.

It is also preferred if the digesting biomass is diluted with inert gas. Any inert gas, such as nitrogen or argon, for example, may be used.

The rumen microorganisms may be rumen archea, bacteria, protozoa or fungi or a mixture thereof.

Further, it is preferred if step a) is conducted under conditions which favor production of the lower alkyl alcohols.

Also, it is preferred if this process further entails adding sulfite to increase hydrogen release.

C. A microbial fuel cell, containing an anode, a cathode and electrolyte therebetween, and a hydrogen source the hydrogen source containing at least rumen microorganisms and biomass digestible thereby, which source produces hydrogen and the hydrogen source being in fluid connection with said anode.

D. A method of producing electricity, which entails generating electricity from the microbial fuel cell described above.

This process preferably further comprises simultaneously producing methane, hydrogen or ethanol while producing said electricity.

Moreover, this process preferably entails perfusing carbon dioxide or nitrogen gas into the microbial fuel cell, thereby increasing the electricity produced.

This process preferably further entails inhibiting production of methane, or removing hydrogen gas, thereby increasing the electricity produced.

E. A process for producing methane from biomass, which entails the step of anaerobically digesting the biomass with at least one species of microorganism cultured from the rumen of a ruminant.

F. A process for producing methane from biomass using a microbial culture, in which any of the following is performed to accelerate the production of methane:
  a) introducing at least one species of microorganism cultured from the rumen of a ruminant,
  b) inoculating a fermenter with an individual species or a mixed culture of rumen microorganisms,
  c) applying a partial vacuum to the fermentation to remove gases,
  d) removing fermentation gases by perfusion of other gases like nitrogen, and
  e) removing methane gas by perfusion of gases not containing methane.

G. A process for producing hydrogen from biomass using a microbial culture, in which any of the following is performed:
  a) introducing at least one species of microorganism cultured from the rumen of a ruminant,
  b) inoculating a fermenter with a mixed culture of rumen microorganisms,
  c) applying a partial vacuum to the fermentation to remove gases,
  d) removing fermentation gases by perfusion of other gases like nitrogen, and
  e) removing hydrogen gas by perfusion of gases not containing hydrogen, and/or
  f) hydrogen is removed with a microbial fuel cell described in item C above, and/or
  g) removing hydrogen or methane with a compressor and membrane system.

H. A process for producing lower alkyl alcohols from plant fiber using a culture of microorganisms, which entails digesting said plant fiber with at least one species of a microorganism.

Preferably, the microorganisms include at least one species of rumen microorganisms.

The process also preferably further entails the step of including methane inhibitors, and may also preferably further entail the step of including short-chain fatty acids.

Further, the process also preferably maintains high enough concentrations of ethanol to select against organisms that would otherwise consume substrates.

The process also preferably further entails the step of removing gas by vacuum.

Moreover, in this process alkyl alcohols are preferably distilled at low pressure during the digestion process.

Advantageously, in this process, ethanol concentrations are maintained high enough to inhibit organisms competing for the same substrate as ethanol producers but low enough not to excessively inhibit ethanol producers.

Moreover, in this process, carbon dioxide is preferably removed by perfusion of other gases, such as methane, which further inhibits methane production.

However, the other gases may also include nitrogen.

However, the other gases may also include gases recycled from the fermentation after removing carbon dioxide.

Further, in this process, hydrogen and methane are preferably produced and collected during the degradation.

Moreover, in this process alkyl alcohols are preferably produced directly from fiber by microorganisms.

In this process, plant fiber may first be degraded to volatile fatty acids or other intermediates that are subsequently converted to ethanol.

Moreover, in this process, degradation to fatty acids is preferably accomplished in the same reactor as for ethanol production and at the same time.

Further, in this process, the degradation to fatty acids is preferably accomplished prior to changing the conditions for ethanol production in the same reactor.

Additionally, in this process, fiber degradation to short-chain fatty acids preferably occurs in a separate reactor prior to conversion of fiber to fatty acids.

I. The process of conversion of short-chain fatty acids to alkyl alcohols using a mixed culture of microorganisms which entails fermenting said short-chain fatty acids with at least one species of a microorganism, which is preferably at least one species of rumen microorganisms.

The process also preferably entails the step of adding hydrogen gas.

The process also further preferably comprises the step of including methane inhibitors.

Moreover, the process further preferably comprises the step of including short-chain fatty acids.

Further, the process advantageously maintains high enough concentrations of ethanol to select against organisms that would otherwise consume substrates.

Moreover, this process preferably further entails the step of removing gas by vacuum.

This process also preferably entails fractionally distilling alkyl alcohols at low pressure during the digestion process.

Further, ethanol concentrations are preferably maintained high enough to inhibit organisms competing for the same substrate as ethanol producers but low enough not to excessively inhibit ethanol producers.

Advantageously, carbon dioxide is removed by perfusion of other gases, which may include methane, which further inhibits methane production. The other gases may also include nitrogen.

Further, the other gases may preferably include gases recycled from the fermentation after removing carbon dioxide.

In this process, hydrogen and methane may be simultaneously produced and collected during the fermentation.

J. A process of converting plant starch to ethanol, which entails the step of digesting plant starch to ethanol in the presence of at least one species of rumen microorganisms.

This process also preferably further entails the step of adding hydrogen gas.

Additionally, this process preferably further entails the step of including methane inhibitors.

Further, this process preferably further entails the step of including short-chain fatty acids.

The process also maintains high enough concentrations of ethanol to select against organisms that would otherwise consume substrates.

Moreover, the process further entails the step of removing gas by vacuum.

Also, in this process, the alkyl alcohols are preferably distilled at low pressure during the digestion process.

Additionally, in this process, ethanol concentrations are maintained high enough to inhibit organisms competing for the same substrate as ethanol producers but low enough not to excessively inhibit ethanol producers.

Moreover, in this process, carbon dioxide is preferably removed by perfusion of other gases.

Also, in this process, the other gases include methane, which further inhibits methane production.

Further, the other gases may also include nitrogen.

Moreover, in this process, the other gases may include gases recycled from the fermentation after removing carbon dioxide.

Further, in this process, where hydrogen and methane may be simultaneously produced and collected during the degradation.

Additionally, in this process, the alkyl alcohols may be produced directly from starch by microorganisms.

Further, in this process, the plain starch is first degraded to volatile fatty acids or other intermediates that are subsequently converted to ethanol.

It is preferred that the degradation to fatty acids be accomplished in the same reactor as for ethanol production and at the same time.

It is also preferred that the degradation to fatty acids be accomplished prior to changing the conditions for ethanol production in the same reactor.

It is further preferred that the starch degradation to short-chain fatty acids occur in a separate reactor prior to conversion of fiber to fatty acids.

K. A process converting five-carbon or six-carbon sugars or both to lower alkyl alcohols, which comprises converting said five or six carbon sugars or both to lower alkyl alcohols in the presence of at least one species of rumen microorganisms.

This process also preferably further entails the step of adding hydrogen gas.

This process also preferably further entails the step of including methane inhibitors.

This process also preferably further entails the step of including short-chain fatty acids.

Further, this process also maintains high enough concentrations of ethanol to select against organisms that would otherwise consume substrates.

Also, it is preferred to further entail the step of removing gas by vacuum.

Additionally, in this process, alkyl alcohols are preferably fractionally distilled at low pressure during the digestion process.

Also, in this process, ethanol concentrations are maintained high enough to inhibit organisms competing for the same substrate as ethanol producers but low enough not to excessively inhibit ethanol producers.

Moreover, it is preferred that carbon dioxide be removed by perfusion of other gases.

Further, in this process, the other gases may include methane, which further inhibits methane production. The other gases may also include nitrogen.

Also, in this process, the other gases include gases recycled from the fermentation after removing carbon dioxide.

Additionally, in this process, hydrogen and methane are preferably simultaneously produced and collected.

L. A method of making ethanol from vinegar, which entails fermenting vinegar with a mixed culture of microorganisms, which cause the vinegar to be changed to ethanol.

Importantly, a significant aspect of the above experiments is that decreasing hydrogen shifted fermentation away from methane production. Additionally, removal of hydrogen (or decreasing reducing potential) greatly increased the rate of biomass, such as hay, digestion.

Further to emphasize the effect of $N_2$ treatment, the following example is provided.

Example 8

The nitrogen treatment was applied as follows. Every two hours, gas was measured and sampled by releasing the total pressure to a glass syringe and allowing it to equilibrate with the atmosphere. Once this excess gas was removed, an additional 20 ml of gas was removed with the gas syringe from the 75 ml headspace above the 50 ml liquid and feed sample. Pure nitrogen gas was then added using the gas syringe allowing it to equilibrate with atmospheric pressure.

The control treatment was a standard in vitro rumen fermentation with gas removed and sampled every 2 hours. The gas phase was allowed to maintain the composition of gases as produced, and approximately one atmosphere pressure. These conditions are similar to the rumen of animals in that constant pressure is maintained by eructation in living ruminants.

For all treatments, 800 mg ground alfalfa hay (Wiley Mill, 1 mm screen) was added to 125 ml digester flasks. Contents were collected from two rumen fistulated cows two hours after feeding; contents were mixed and strained through cheese cloth. Contents were maintained under anaerobic conditions by perfusion with nitrogen gas. Strained rumen fluid was mixed with buffer in a ratio of 40:6 (fluid:buffer) by volume. Buffer was as described by Goering and Van Soest (1970) for the control treatment. For the other two treatments, $NaHCO_3$ was replaced with an equimolar concentration of NaCl so as to decrease $CO_2$ gas in solution. Fifty ml of inoculated media was added to each flask. All flasks were incubated together in a shaking water bath at 38° C. Flasks were sampled for gases, and volatile fatty acids every 2 hours from 0 to 8 hours, and at 12 and 24 hours. Because of the time necessary for sampling, the 0-hour sample was at after 30 minutes incubation, and all other time points are delayed by 30 minutes from nominal time. For vacuum treatments, recovery of gases was incomplete during the 12 and 24-hour time points. Therefore, only ratios of gases (not total amounts) are reported at 12 and 24 hours. Gases and volatile fatty acids were analyzed by gas chromatography equipped with a packed column for each of gases and acids. Owing to the small sample size, and equipment difficulties, volatile fatty acid concentrations are not reported for this preliminary study. Each treatment was replicated four times in separate flasks.

Results

Figure 21:
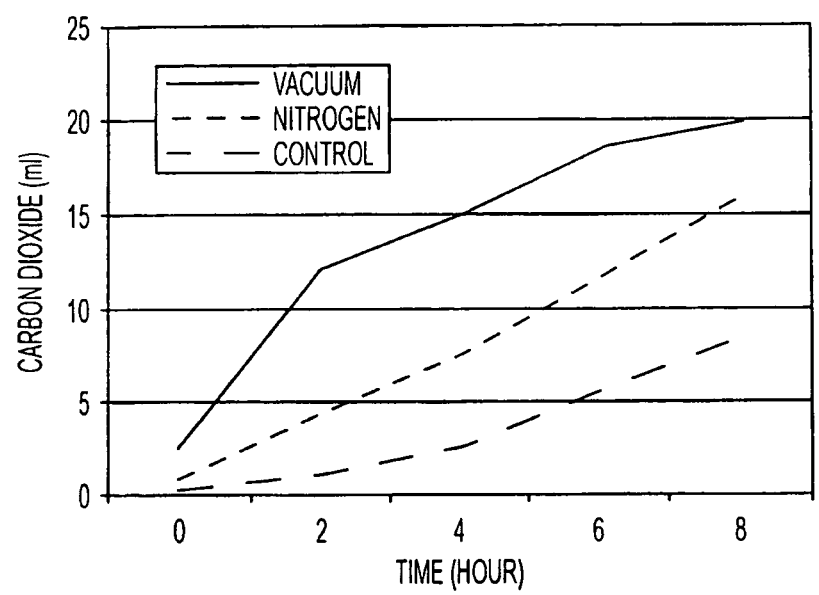
FIG. 21 illustrates rate of release of carbon dioxide from digestion and fermentation with rumen microbes under 0.25 atmospheres total pressure (Vacuum), removal of gas every two hours and replacement with dimolecular nitrogen (Nitrogen), and maintained under 1 atmosphere produced gases: carbon dioxide and methane (Control). Average of 4 replicates per treatment: ANOVA indicated differences among treatments (P<0.01) for all time points beyond initial (2, 4, 6, 8 h); SE ranged from 0.4 to 2.1 ml depending on time point.

Carbon dioxide production from three experimental treatments are shown in FIG. 21. Production of total gas volume or carbon dioxide has been shown to represent digestion rate of plant material, as one molecule of carbon dioxide is released per molecule of acetate produced. The control treatment is typical for rumen fermentation rate and is considered rapid among anaerobic digesters. The other treatments show greatly accelerated rates of carbon dioxide and methane production.

Figure 22:
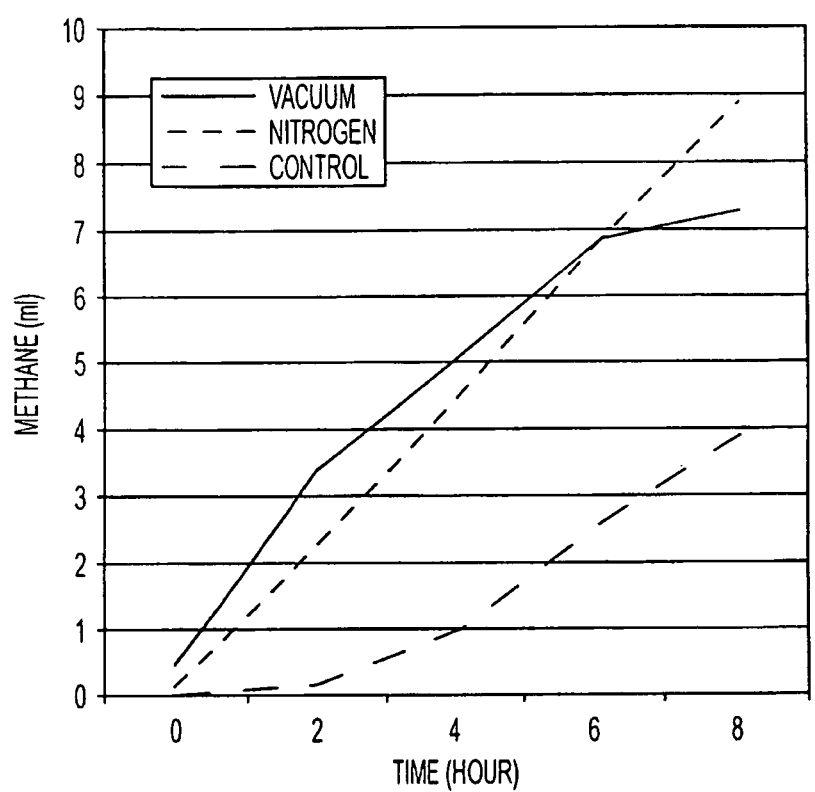
FIG. 22 illustrates rate of release of methane from digestion and fermentation with rumen microbes under 0.25 atmospheres total pressure (Vacuum), removal of gas every two hours and replacement with dimolecular nitrogen (Nitrogen), and maintained under 1 atmosphere produced gases: carbon dioxide and methane (Control). Average of 4 replicates per treatment: ANOVA indicated differences among treatments (P<0.01) for all time points beyond initial (2, 4, 6, 8 h); SE ranged from 0.1 to 0.4 ml depending on time point.

FIG. 22 shows the production of methane over time for three treatments:
1) vacuum, 2) nitrogen and 3) control.

Figure 23:
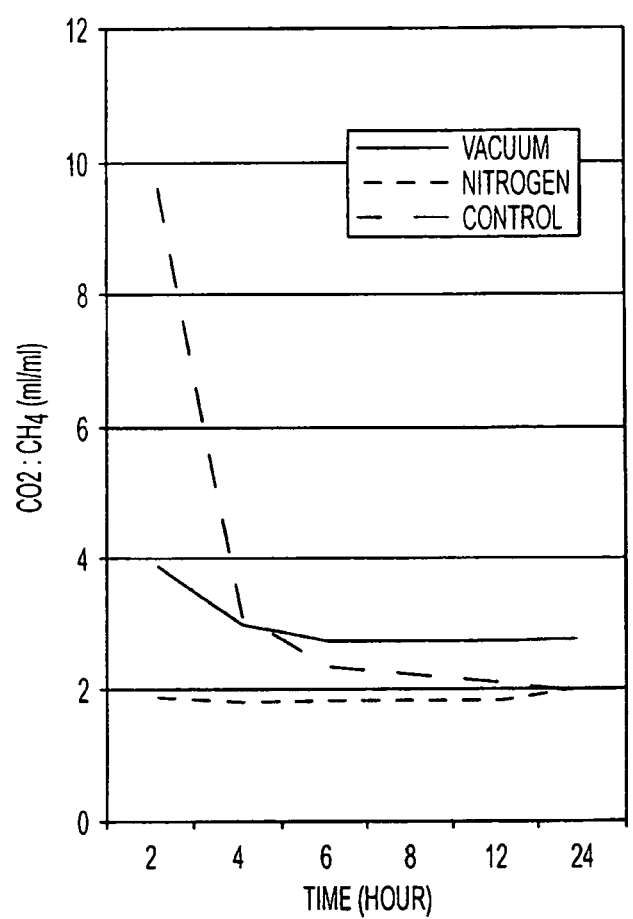

FIG. 23 shows the ratio of carbon dioxide to methane over time. The control treatment started out high due to low methane production, but eventually declined to the ratio of the nitrogen treatment. The vacuum had the highest ratio for 4 to 24 hours. This observation reflects the capture of hydrogen in the vacuum system. That hydrogen was no longer available to reduce carbon dioxide to methane. The results show the potential for releasing bio-gas from digestion with rumen microbes. The results also show the potential to manipulate the fermentation to change end products.

Figure 24:
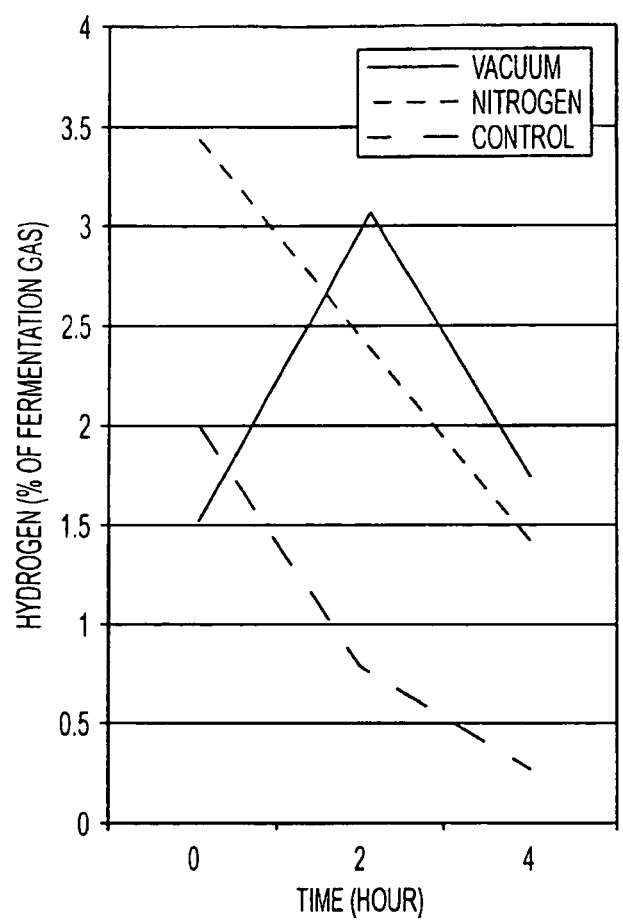
FIG. 24 illustrates hydrogen concentration (% of produced gases) for initial time points of digestion and fermentation with rumen microbes under 0.25 atmospheres total pressure (Vacuum), removal of gas every two hours and replacement with dimolecular nitrogen (Nitrogen), and maintained under 1 atmosphere produced gases: carbon dioxide and methane (Control). Average of 4 replicates per treatment: ANOVA indicated differences among treatments (P>0.05) at initial time point, and (P<0.0001) for later time points.

FIG. 24 shows the production of hydrogen gas from each treatment for initial time points. Additional time points may still be possible to be analyzed. Removing hydrogen gas resulted in greater production of hydrogen by the fermentation. The hydrogen gas concentration increased by four to seven-fold for the vacuum and nitrogen treatments compared to control. This hydrogen equivalent would be available for subsequent reactions.

Further, a combined device for generating hydrogen and storing hydrogen for subsequent use is contemplated. For example, the combined device may be one or more fermentation tanks or containers in fluid connection with a gas trap and compressor to store hydrogen for subsequent use.

Any conventional hydrogen trap may be used. See, for example, U.S. Pat. No. 6,068,683, which is incorporated herein in the entirety.

Finally, the present inventor explicitly discloses a methane digester which is more cost effective than conventional methane digesters. As exemplary conventional digesters, those disclosed in the U.S. Pat. Nos. 6,673,243 and 6,855,253, may be noted. Both U.S. patents are incorporated by reference herein in the entirety.

However, there are three features of the methane digester of the present invention, which offer significant advantages.

Any one of these features may be used alone or in combination with one or both of the others.

These features are:
1) use of, at least, rumen microorganisms; which provide faster rates of digestion, to provide in turn a faster flow through;
2) use of perfusion or removal of gases (methane and hydrogen) because these gases become limiting with faster digestion rates; and
3) especially removal of hydrogen as it is more valuable than methane and such removal has a greater impact on the fermentation.

The perfusion or removal of methane and hydrogen may be effected, for example, with a compressor and a membrane. Any conventional compresses and membranes for separating hydrogen and methane may be used. As exemplary membranes, those disclosed in U.S. Pat. Nos. 5,000,763, 5,507,856; 6,183,628 and 6,264,828 may be noted. All of these patents are incorporated herein by reference in the entirety.

In the present methane digester, i.e., generator, hydrogen produced may be compressed in order to create a concentration gradient to move it through the membrane. As gas compression requires energy, once the hydrogen is removed, the energy in the remaining compressed gas on the retentate side of the membrane may be recovered to run the pump to compress new gas. There are many examples of pumps powered by compressed gas. See, for example, U.S. Pat. Nos. 5,806,795 and 7,260,940, both of which are incorporated herein by reference in the entirety.

In accordance with the present invention, any type of anaerobic digester may be used for the digesting biomass. However, as noted above, the present methods all utilize moderate temperatures as described. Examples of digester types which may be used are: covered lagoon digesters, complete mix digesters and plug flow digesters. All of these types of digesters are well-known.

Further, it is explicitly contemplated herein that methane or hydrogen or both may be generated by digesting biomass, as defined herein, with conventional microorganisms, such as fecal bacteria, in coordination with perfusion or removal of hydrogen and/or methane. In this process, hydrogen and/or methane may be removed using a compressor and membrane as described above.

For example, one aspect of the present invention involves the use of conventional manure digesters, but with removal of hydrogen and/or methane. Thus, for example, a manure digester as disclosed in U.S. Pat. No. 5,096,579 may be used, but with removal of hydrogen and/or methane by a compressor and membrane as described above. U.S. Pat. No. 5,096,579 is incorporated herein by reference in the entirety. These gases may also be removed and used in a microbial fuel cell. For example, the off gases, hydrogen and methane, may be removed by a pump and then separated by a membrane as described above. The separated hydrogen may then be used in a microbial fuel cell. For example, the microbial fuel cell of U.S. Pat. No. 6,846,584 may be noted. U.S. Pat. No. 6,846,584 is incorporated herein by reference in the entirety.

Although any of the types of anaerobic digesters noted above may be used, a digester such as is disclosed in U.S. Pat. No. 6,855,253 may also be used. This patent is also incorporated herein by reference in the entirety.

Moreover, it is explicitly contemplated herein that electricity produced by the microbial fuel cell of the present invention may be sold directly to a power grid with recovering and purifying hydrogen methane after removal from the digesting biomass.

Alternatively, it is also explicitly contemplated that after removal of hydrogen and methane from the digesting biomass, the hydrogen and methane may be recovered and purified by a compressor and one or more membranes as described above. The purified methane and hydrogen may be sold separately either as compressed gases or in liquefied form.

It will now be apparent that many changes and modifications may be made to the above-described embodiments without departing from the spirit and scope of the present invention.

What is claimed:

1. A method for producing ethanol from biomass from digestion by microorganisms, which comprises steps of:
   a) adding exogenous hydrogen gas into a fermentation container containing biomass;
   b) adding ethanol to the fermentation container to stimulate production of ethanol from the digestion of the biomass;
   c) digesting the biomass in the fermentation container with at least one microorganism which produces ethanol from digestion of cellulose, hemi-cellulose, starch, lignin or lignocellulosic substrates or mixtures thereof contained in the biomass at a temperature of about 50° C. or less; and
   d) reducing partial pressures of carbon dioxide and hydrogen gases produced by the digesting, thereby causing a ratio of reactants and products to shift to a new thermodynamic equilibrium that yields a greater concentration of the ethanol from the digested biomass; and
   e) collecting the ethanol produced from the digested biomass.

2. The method of claim 1, wherein the amount of ethanol added in step b) is 100 mM.

3. The method of claim 1, wherein the digesting is effected for longer than 24 hours.

4. The method of claim 1, wherein the at least one microorganism is a rumen microorganism.

5. The method of claim 1, wherein the digesting is conducted in the presence of a methane inhibitor.

6. The method of claim 1, wherein the at least one microorganism is a bacterium, which is *Ruminococcus albus*.

7. The method of claim 1, wherein a mixture of microorganisms is used.

8. The method of claim 7, wherein the mixture is a mixture of bacteria and fungi.

9. The method of claim 7, wherein the mixture of microorganisms comprises rumen inocula.

10. The method of claim 1, wherein the digesting is conducted at about 45° C. or less.

11. The method of claim 1, wherein the digesting is conducted at a pH of from about 6 to 8.

12. The method of claim 1, wherein the biomass comprises grasses, leaves, paper or cardboard or a combination thereof.

13. The method of claim 1, wherein the biomass comprises grasses, which is timothy.

14. The method of claim 4, wherein the at least one microorganism is a pure culture of rumen microorganism isolated from rumen.

15. The method of claim 1, wherein the biomass further comprises five-carbon sugar, and the at least one microorganism produces ethanol from the five-carbon sugar.

16. The method of claim 1, wherein carbon dioxide produced by the digesting is removed by vacuum.

17. The method of claim 1, wherein partial pressures of gases of carbon dioxide and hydrogen gases produced by the digesting are reduced, thereby causing a ratio of reactants and products to shift to reestablish a state of new thermodynamic equilibrium, wherein said shift leads to a decreased production of digestion products other than ethanol.

18. The method of claim 1, wherein the reducing of partial pressures of carbon dioxide and hydrogen gases produced by the digesting causes a ratio of reactants and products to shift to establish a state of new thermodynamic equilibrium that enriches or selects for microorganisms that digest cellulosic biomass and produce ethanol.

19. The method of claim 18, wherein the reducing of the partial pressures of carbon dioxide and hydrogen gases produced by the digesting increases the concentration of dissolved carbon dioxide and hydrogen and leads to an increased production of organic acid by a pure culture of a rumen micro-organism and subsequently leads to an increased production of ethanol.

20. The method of claim 19, wherein the organic acid is acetic acid.

21. The method of claim 1, wherein the ethanol is collected by vacuum distillation during digestion.

* * * * *